US012725706B2

(12) United States Patent
Sandler et al.

(10) Patent No.: US 12,725,706 B2
(45) Date of Patent: Sep. 1, 2026

(54) METHODS, SYSTEMS, APPARATUSES, AND DEVICES FOR FACILITATING A DIAGNOSIS OF PATHOLOGIES USING A MACHINE LEARNING MODEL

(71) Applicant: iCardio.ai, Los Angeles, CA (US)

(72) Inventors: Roman A. Sandler, Valley Village, CA (US); Joseph Sokol, Los Angeles, CA (US); Daniel Sokol, Los Angeles, CA (US); Damjan Postolovski, Piscataway, NJ (US); Aleksandar Stojmenski, Skopje (MK); Markos Amsalu Muche, Addis Ababa (ET); Harris Lee Bergman, Marietta, GA (US); Jack Elie Gindi, New York, NY (US)

(73) Assignee: iCardio.ai, Los Angeles, CA (US)

( * ) Notice: Subject to any disclaimer, the term of this patent is extended or adjusted under 35 U.S.C. 154(b) by 246 days.

(21) Appl. No.: 18/422,311

(22) Filed: Jan. 25, 2024

(65) Prior Publication Data

US 2024/0257967 A1 Aug. 1, 2024

Related U.S. Application Data

(60) Provisional application No. 63/441,177, filed on Jan. 26, 2023.

(51) Int. Cl.
*G16H 50/20* (2018.01)
*G06V 10/82* (2022.01)
(Continued)

(52) U.S. Cl.
CPC ............. *G16H 50/20* (2018.01); *G06V 10/82* (2022.01); *G16H 30/20* (2018.01); *G16H 30/40* (2018.01);
(Continued)

(58) Field of Classification Search
CPC .. G06V 10/82; G06V 10/764; G06V 2201/03; G06V 10/77; G06V 10/454;
(Continued)

(56) References Cited

U.S. PATENT DOCUMENTS 7,244,230 B2 * 7/2007 Duggirala ................ A61B 8/56 600/443
12,380,554 B2 * 8/2025 Chung .................. G16H 30/40
(Continued)

OTHER PUBLICATIONS

Golovanevsky, Michal, Carsten Eickhoff, and Ritambhara Singh. "Multimodal attention-based deep learning for Alzheimer's disease diagnosis." Journal of the American Medical Informatics Association 29.12 (2022): 2014-2022. (Year: 2022).*

*Primary Examiner* — Courtney Joan Nelson
(74) *Attorney, Agent, or Firm* — Dhiraj Jindal; PATENT YOGI LLC

(57) ABSTRACT

A method for facilitating a diagnosis of pathologies using a machine learning model includes receiving a medical data from a device, analyzing the medical data using a machine learning model comprising an artificial neural network which comprises an input layer which takes medical data as inputs, a middle layer which outputs a lower dimensional abstract vector space representation for each inputs by encoding the medical data to a lower dimensional abstract vector space, and output layers which classifies the lower dimensional abstract vector space representation to outputs corresponding to assessment parameters considered in the diagnosis of the pathologies, obtaining outputs from the machine learning model for the diagnosis of pathologies based on the analyzing, generating a result based on the outputs, and storing the result and the machine learning model.

20 Claims, 85 Drawing Sheets

(51) Int. Cl.
*G16H 30/20* (2018.01)
*G16H 30/40* (2018.01)
*G16H 70/60* (2018.01)

(52) U.S. Cl.
CPC ....... *G16H 70/60* (2018.01); *G06V 2201/031* (2022.01)

(58) Field of Classification Search
CPC ............... G06V 10/811; G06V 40/193; G06V 30/1918; G06V 2201/031; G06N 3/0464; G06N 3/045; G06N 3/08; G06N 20/00; G06N 3/02; G16H 50/20; G16H 30/40; G16H 30/20; G16H 50/30; G16H 15/00; G16H 10/60; G16H 70/60; G06T 2207/20081; G06T 7/0012; G06T 2207/20084; G06T 2207/10132; G06T 2207/30048; G06T 5/60; G06F 18/25; G06F 18/253
See application file for complete search history.

(56) References Cited

U.S. PATENT DOCUMENTS

2019/0139641 A1* 5/2019 Itu ........................ G06N 3/0464
2020/0211694 A1* 7/2020 Nye .......................... G06T 7/11
2022/0405933 A1* 12/2022 Tajbakhsh .............. G06N 3/096

* cited by examiner

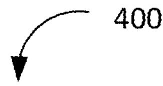

RECEIVING, USING THE COMMUNICATION DEVICE, AT LEAST ONE ADDITIONAL MEDICAL DATA ASSOCIATED WITH THE AT LEAST ONE USER FROM THE AT LEAST ONE DEVICE, WHEREIN THE AT LEAST ONE MEDICAL DATA IS ASSOCIATED WITH AT LEAST ONE MODALITY AND THE AT LEAST ONE ADDITIONAL MEDICAL DATA IS ASSOCIATED WITH AT LEAST ONE ADDITIONAL MODALITY

402

ANALYZING, USING THE PROCESSING DEVICE, THE AT LEAST ONE ADDITIONAL MEDICAL DATA USING THE AT LEAST ONE MACHINE LEARNING MODEL, WHEREIN THE AT LEAST ONE MACHINE LEARNING MODEL FURTHER COMPRISES AT LEAST ONE ADDITIONAL ARTIFICIAL NEURAL NETWORK, WHEREIN THE AT LEAST ONE ARTIFICIAL NEURAL NETWORK IS TRAINED USING A SET OF TRAINING MEDICAL DATA ASSOCIATED WITH THE AT LEAST ONE MODALITY AND THE AT LEAST ONE ADDITIONAL ARTIFICIAL NEURAL NETWORK IS TRAINED USING A SET OF ADDITIONAL TRAINING MEDICAL DATA ASSOCIATED WITH THE AT LEAST ONE ADDITIONAL MODALITY, WHEREIN THE SET OF ADDITIONAL TRAINING MEDICAL DATA CORRESPONDS TO THE SET OF TRAINING MEDICAL DATA, WHEREIN THE AT LEAST ONE ARTIFICIAL NEURAL NETWORK AND THE AT LEAST ONE ADDITIONAL ARTIFICIAL NEURAL NETWORK ARE JOINTLY TRAINED WITH A CROSS MODALITY ARTIFICIAL NEURAL NETWORK OF THE AT LEAST ONE MACHINE LEARNING MODEL USING A LOSS FUNCTION CREATED USING OUTPUTS FROM THE CROSS MODALITY ARTIFICIAL NEURAL NETWORK, THE AT LEAST ONE ARTIFICIAL NEURAL NETWORK, AND THE AT LEAST ONE ADDITIONAL ARTIFICIAL NEURAL NETWORK, WHEREIN THE OBTAINING OF THE ONE OR MORE OUTPUTS IS FURTHER BASED ON THE ANALYZING OF THE AT LEAST ONE ADDITIONAL MEDICAL DATA

Figure 6:
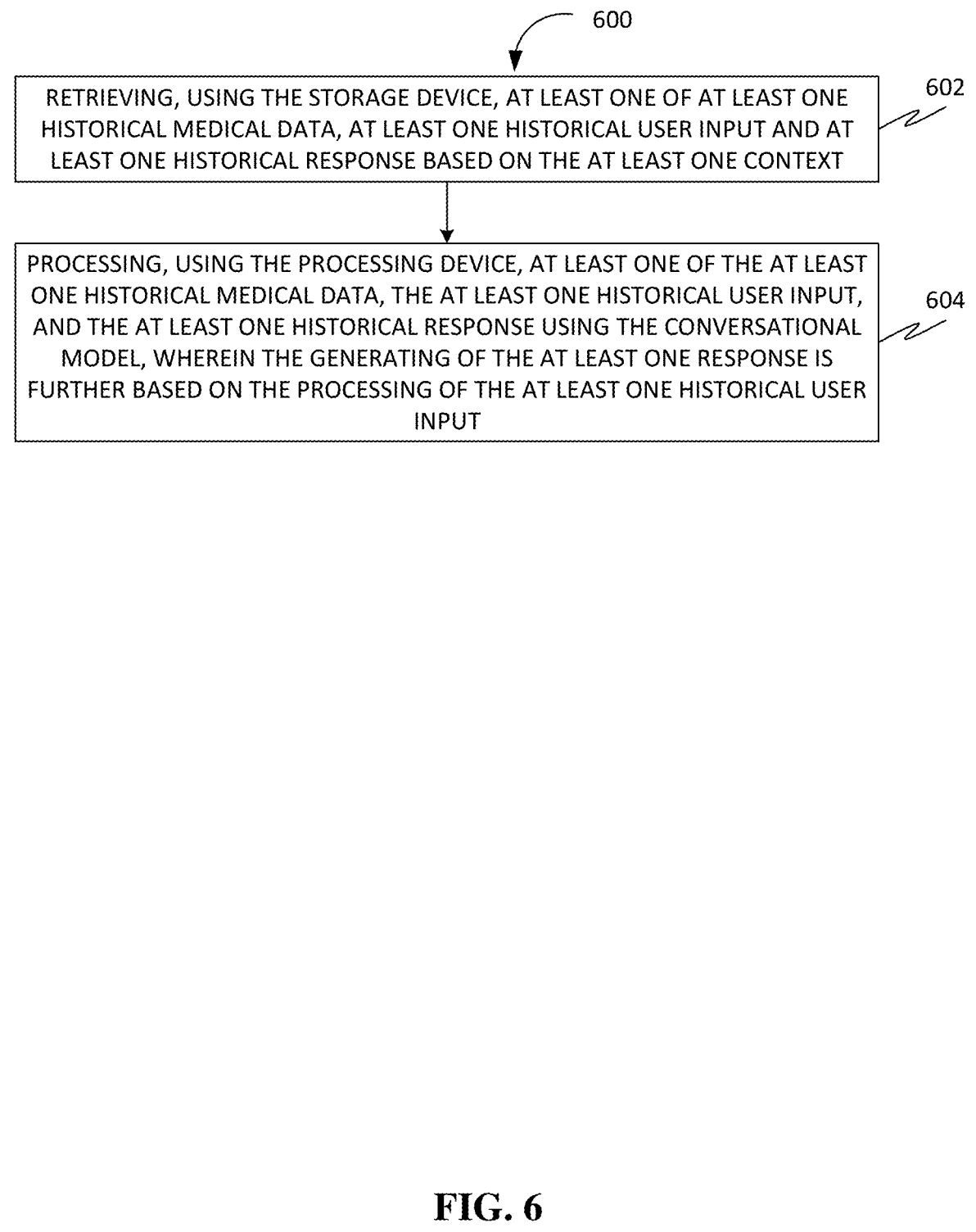

RETRIEVING, USING THE STORAGE DEVICE, AT LEAST ONE OF AT LEAST ONE HISTORICAL MEDICAL DATA, AT LEAST ONE HISTORICAL USER INPUT AND AT LEAST ONE HISTORICAL RESPONSE BASED ON THE AT LEAST ONE CONTEXT

602

PROCESSING, USING THE PROCESSING DEVICE, AT LEAST ONE OF THE AT LEAST ONE HISTORICAL MEDICAL DATA, THE AT LEAST ONE HISTORICAL USER INPUT, AND THE AT LEAST ONE HISTORICAL RESPONSE USING THE CONVERSATIONAL MODEL, WHEREIN THE GENERATING OF THE AT LEAST ONE RESPONSE IS FURTHER BASED ON THE PROCESSING OF THE AT LEAST ONE HISTORICAL USER INPUT

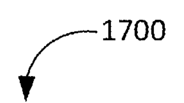

| Cardia indication | AUROC |
|---|---|
| Aortic – Stenosis | 0.98 |
| Left Ventricle – Atrial Fibrillation | 0.97 |
| Mitral Valve – Bioprosthetic | 0.96 |
| Mitral Valve Annular Calcification | 0.96 |
| Aortic Valve Calcification | 0.95 |
| Right Atrium Pacemaker | 0.94 |
| Mitral Valve Thickening | 0.94 |
| Myxomatous Mitral Valve | 0.94 |
| Left Ventricle Enlargement | 0.93 |
| Left Ventricle Hypokinesis | 0.93 |
| Aortic Valve Bioprosthetic | 0.93 |
| Right Atrium Enlargement | 0.92 |
| Right Ventricle Pacemaker | 0.92 |
| Aortic Sclerosis | 0.92 |
| Left Ventricle Basal Septal Hypertrophy | 0.91 |
| Aortic Root Dilation | 0.90 |
| Left Ventricle – Hypertrophy | 0.89 |
| Aortic Valve – Thickening | 0.88 |
| Pericardial Effusion | 0.88 |
| Left Atrium – Enlargement | 0.87 |
| Dilated Ascending Aorta | 0.84 |
| Right Ventricle Enlargement | 0.84 |
| Left Ventricle Diastolic Dysfunction | 0.83 |
| Aortic Valve Bicuspid | 0.82 |
| Aortic Valve Insufficiency | 0.81 |

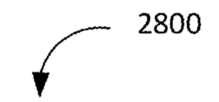
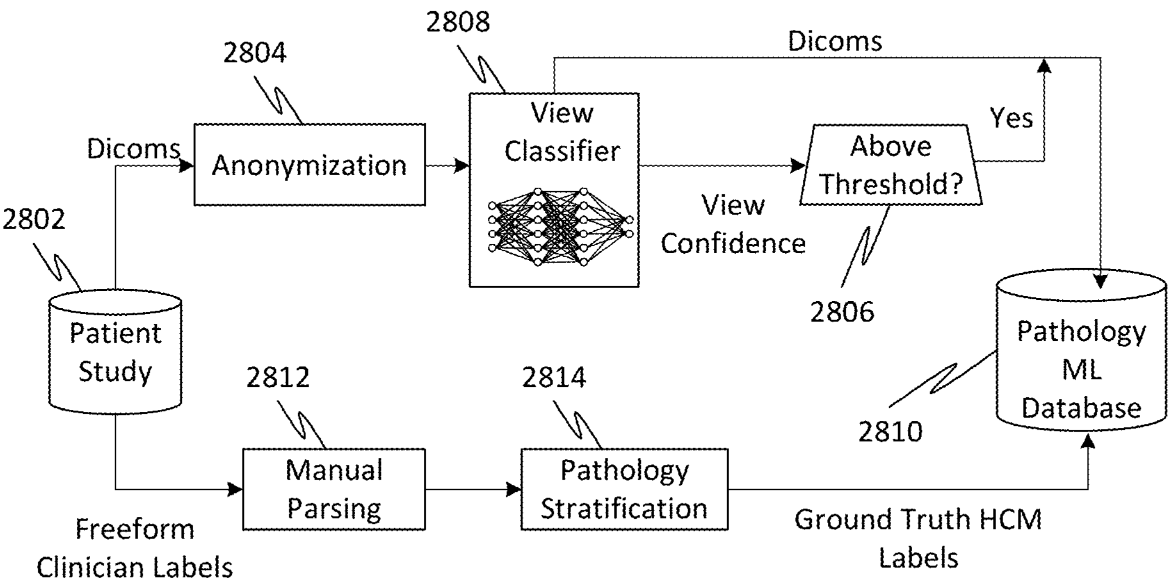
FIG. 28

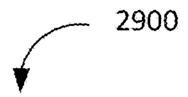
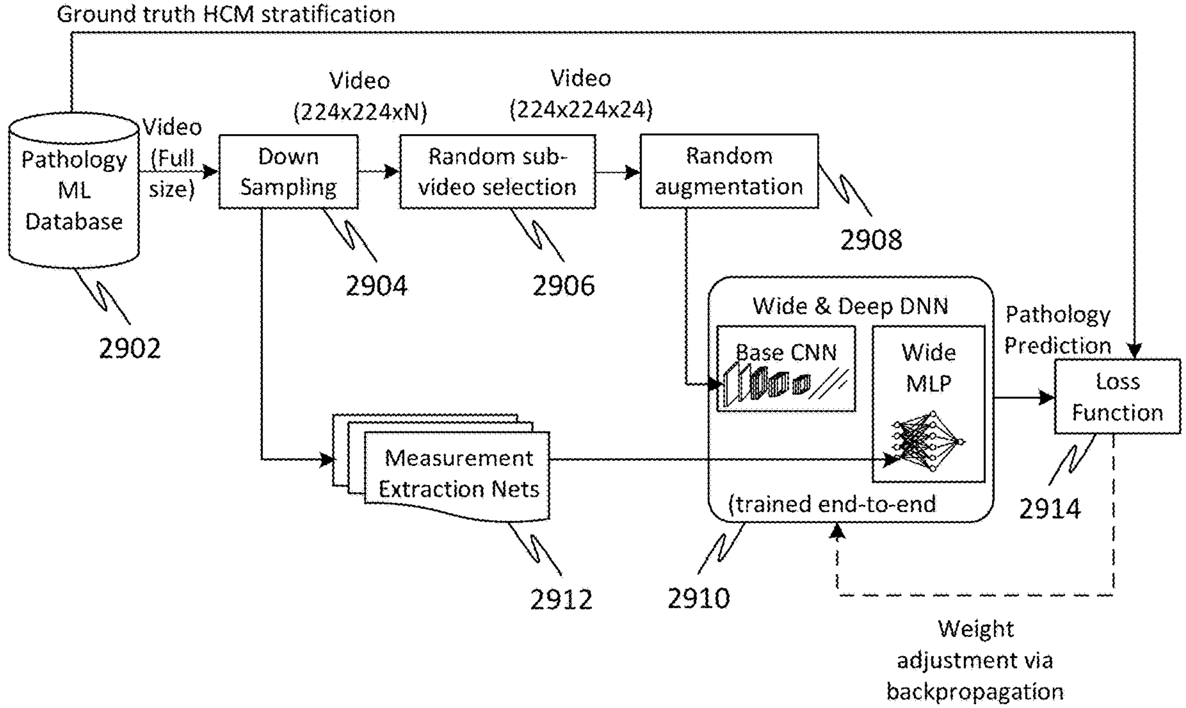
FIG. 29

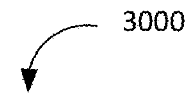
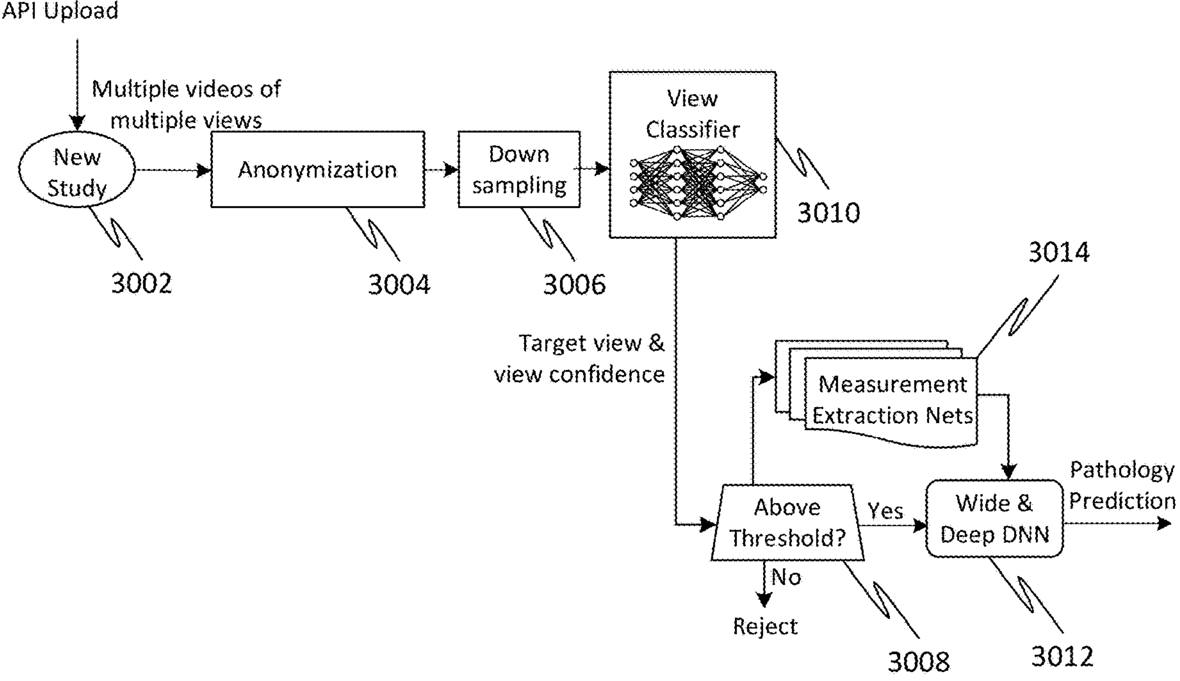
FIG. 30

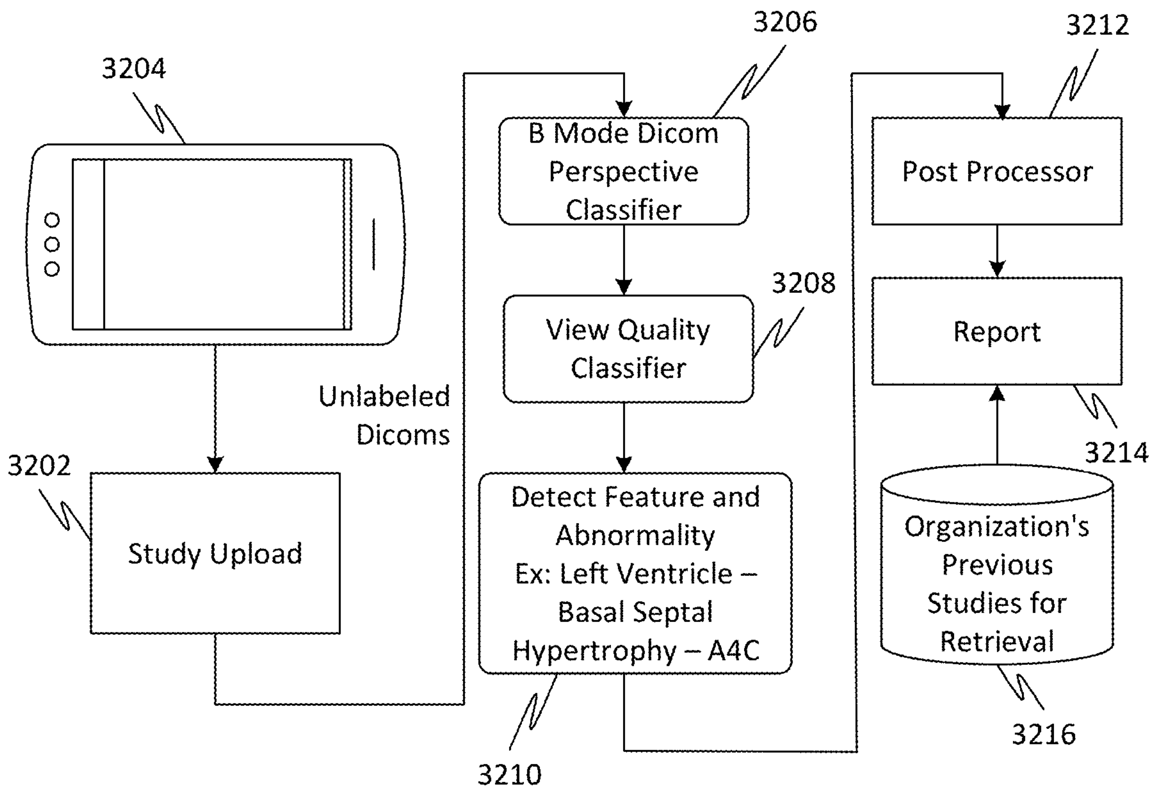
FIG. 32

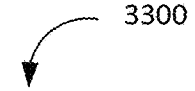
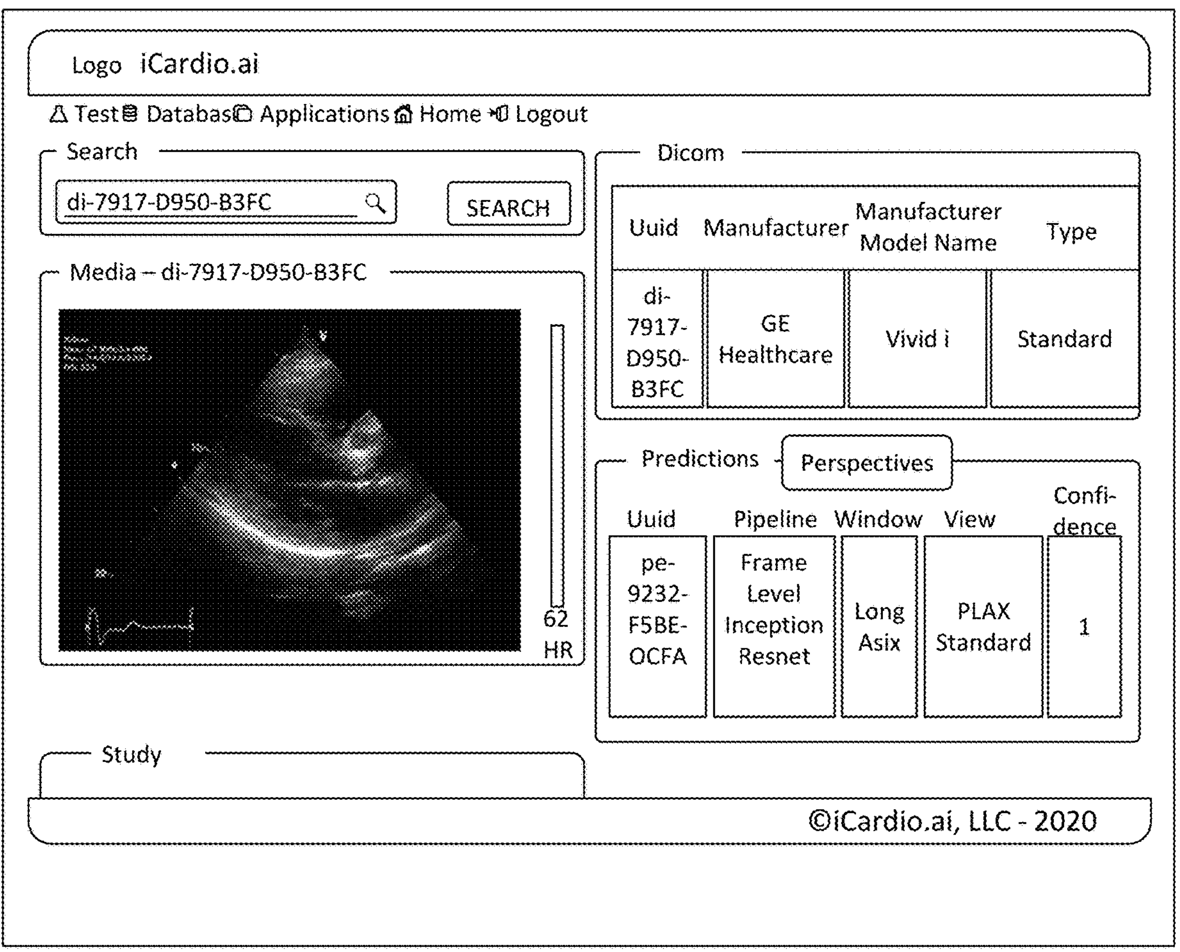
FIG. 33

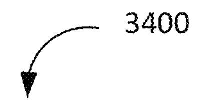
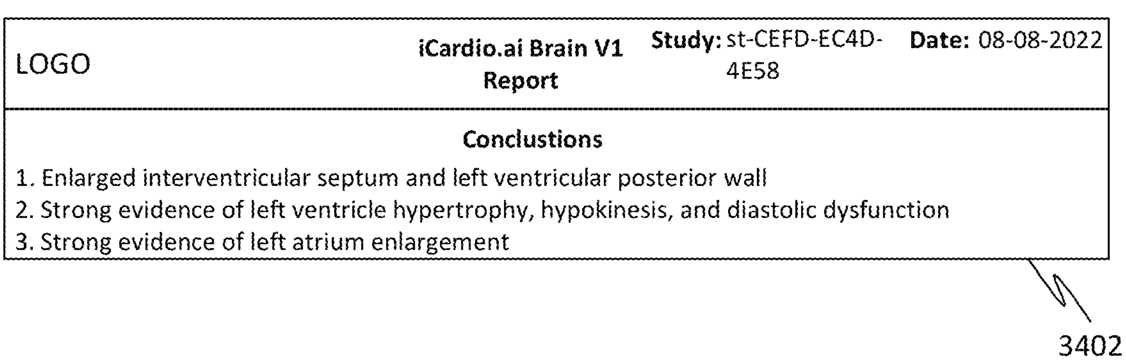
FIG. 34

3400

3502

| Findings | | |
|---|---|---|
| **Feature** | **Condition** | **Prediction** |
| **Left Ventricle** | Hypertrophy | 82% |
| | Hypokinesis | 61% |
| | Atrial Fibrilation | 7% |
| | Basal Septal Hypertrophy | 2% |
| | Enlargement | 0% |
| | Diastolic Dysfunction | % |
| **Right Ventricle** | Pacemaker | 1% |
| | Enlargement | 46% |
| **Left Atrium** | Enlargement | 66% |
| **Right Atrium** | Pacemaker | 19% |
| | Enlargement | 1% |
| **Mitral Valve** | Regurgitation | 46% |
| | Calcification | 8% |
| | Myxomatous | 7% |
| | Thickened | 1% |
| **Tricuspid Valve** | Regurgitation | 36% |
| **Aortic root** | Dilated Ascending Aorta | 4% |
| | Dilation | 49% |
| **Aortic Valve** | Bioprosthetic | 3% |
| | Stenosis | 1% |
| | Bicuspid | 1% |
| | Insufficiency | 26% |
| | Sclerosis | 2% |
| | Calcification | 5% |
| | Thickened | 1% |
| **Pericardium** | Effusion | 48% |

FIG. 35

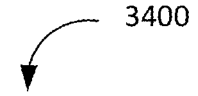

3602

| Measurements | | | |
|---|---|---|---|
| **PAP** | Pulmonary Pressure | 26.68mmHg | 0.0 – 40.0 mmHg |
| **IVSD** | Thickness of the Interventricular Septum | 1.58 cm | 0.6 – 1.0 cm |
| **LVPWD** | Thickness of the Left Ventricular Posterior Wall | 1.15 cm | 0.6 – 1.0 cm |
| **RVSD** | Right Ventricular Systolic Diameter | 1.94 cm | |
| **RVDD** | Right Ventricular Diastolic Diameter | 2.53 cm | 2.5 – 4.0 cm |
| **LVSD** | Left Ventricular Systolic Diameter | 2.86 cm | 2.5 – 4.0 cm |
| **LVDD** | Left Ventricular Diastolic Diameter | 4.23 cm | 4.2 – 5.8 cm |
| **SJ** | Sinotubular Junction | 3.02 cm | 2.6 – 3.2 cm |
| **SOV** | Sinus of Valsalva | 3.47 cm | 3.1 – 3.7 cm |
| **AA** | Aortic Anulus | 2.25 cm | 2.3 – 2.9 cm |
| **LVOT** | Left Ventricular Outflow Tract | 2.12 cm | 2.3 – 2.9 cm |
| **EF** | Ejection Fraction | 54.02% | 53.0 – 73.0% |

FIG. 36

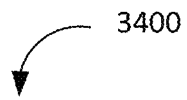
Left Ventricular Outflow Tract: 2.12cm
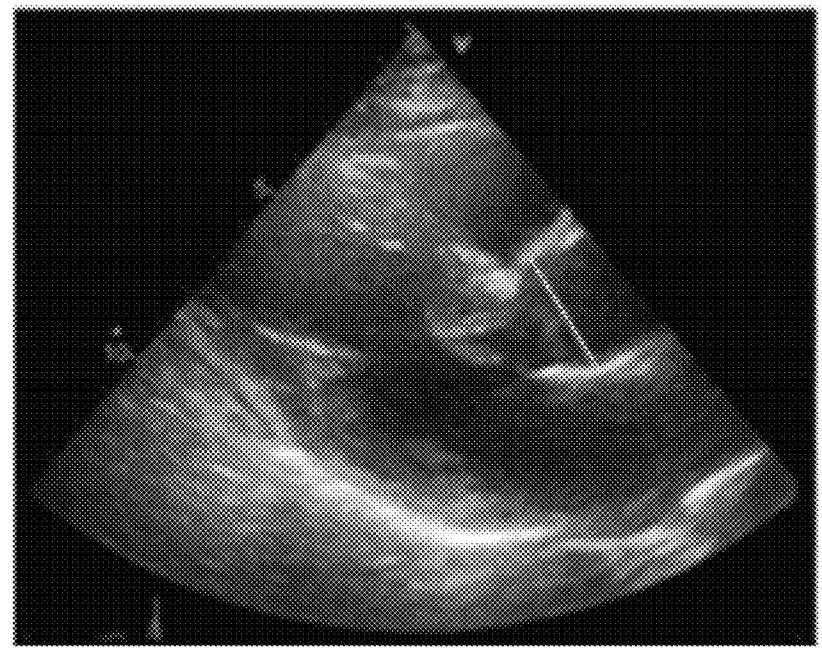
FIG. 37

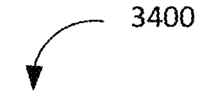
3802
Left Ventricular Volume (A4C)
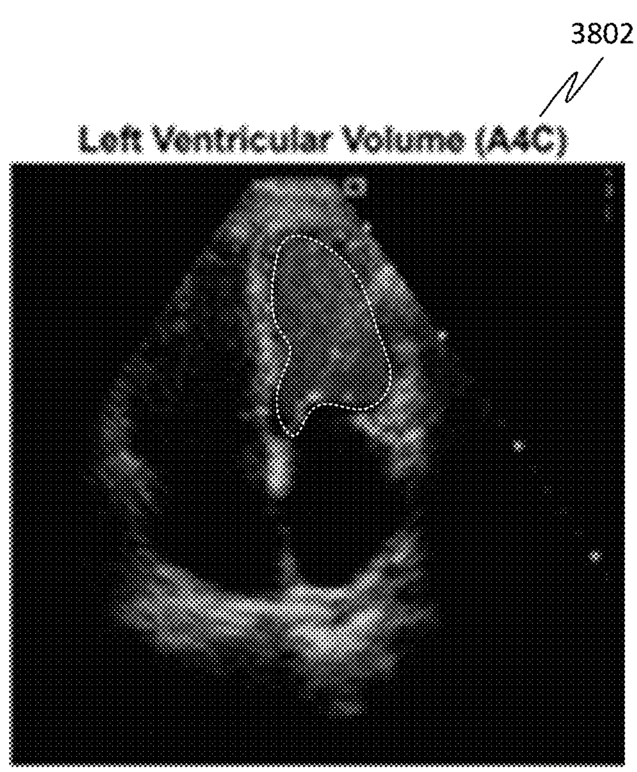
FIG. 38

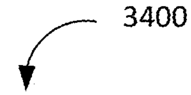
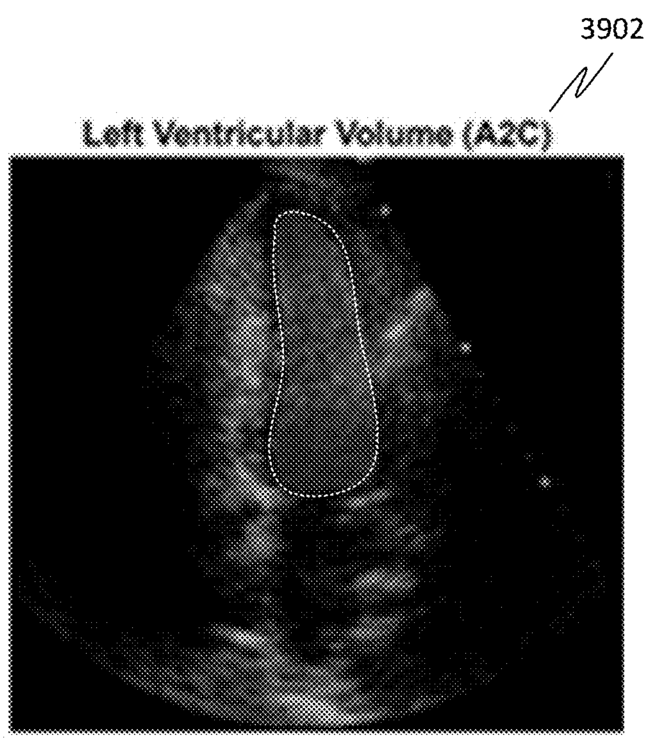
FIG. 39

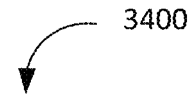
FIG. 40

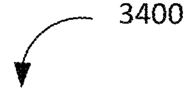
Left Ventricular Posterior Wall: 1.15cm
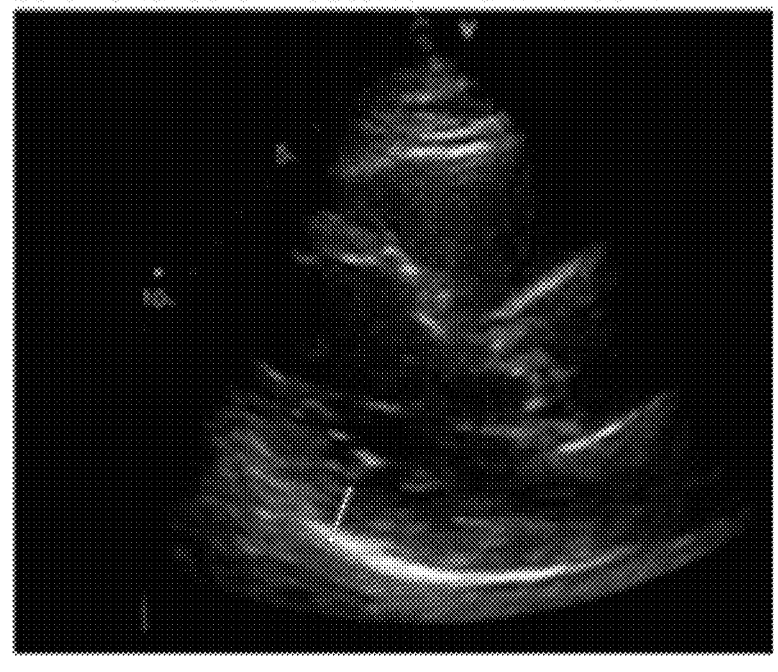
FIG. 41

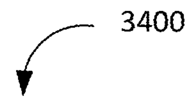
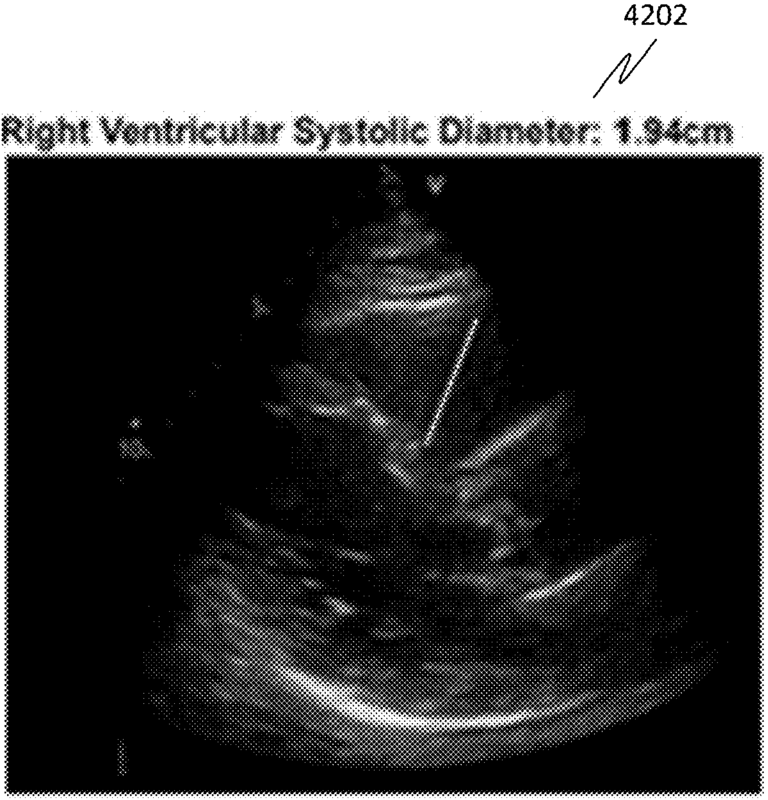
FIG. 42

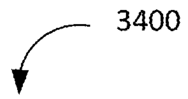
Right Ventricular Diastolic Diameter: 2.53cm
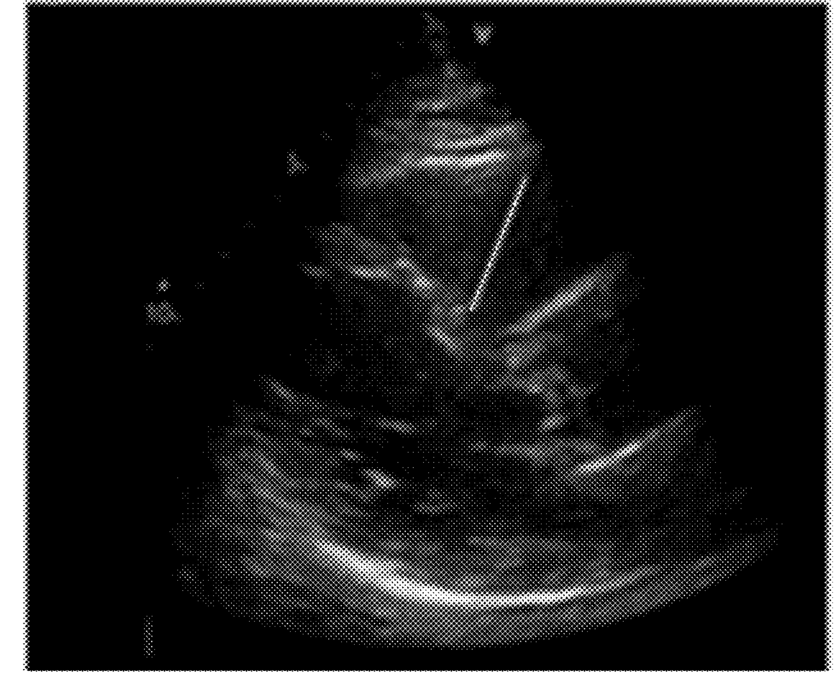
FIG. 43

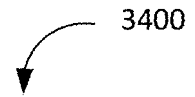
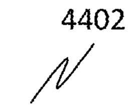
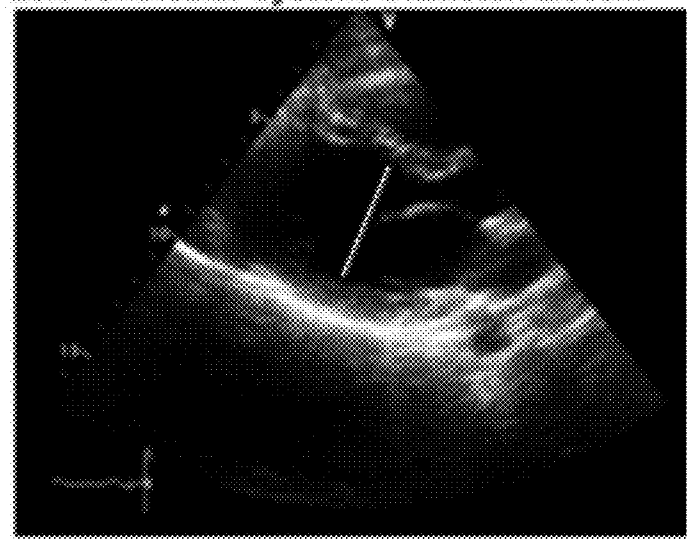
FIG. 44

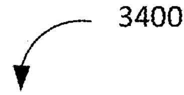
4502
Left Ventricular Diastolic Diameter: 4.23cm
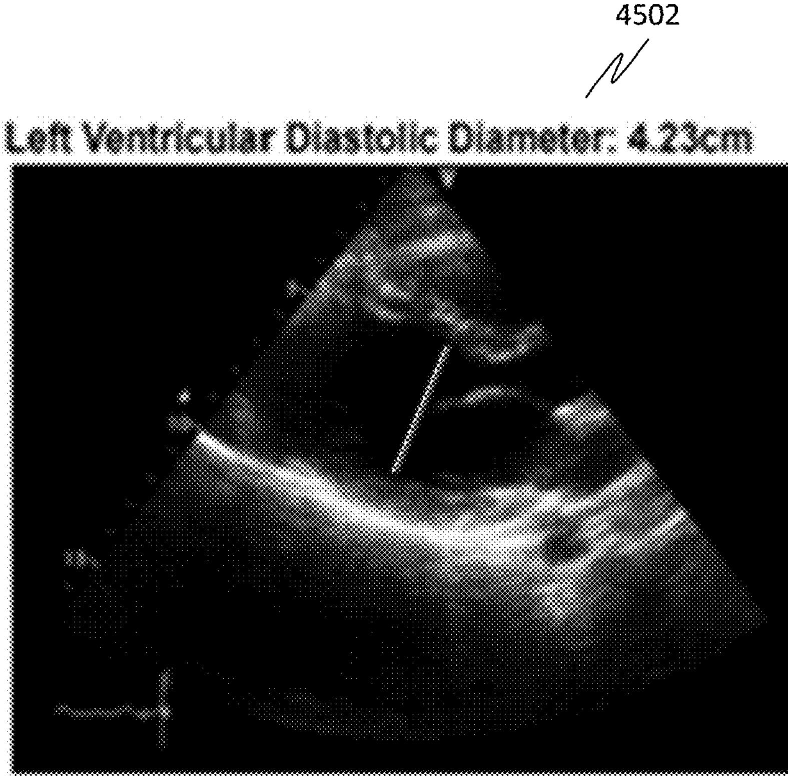
FIG. 45

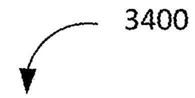
Sinotubular Junction: 3.02cm
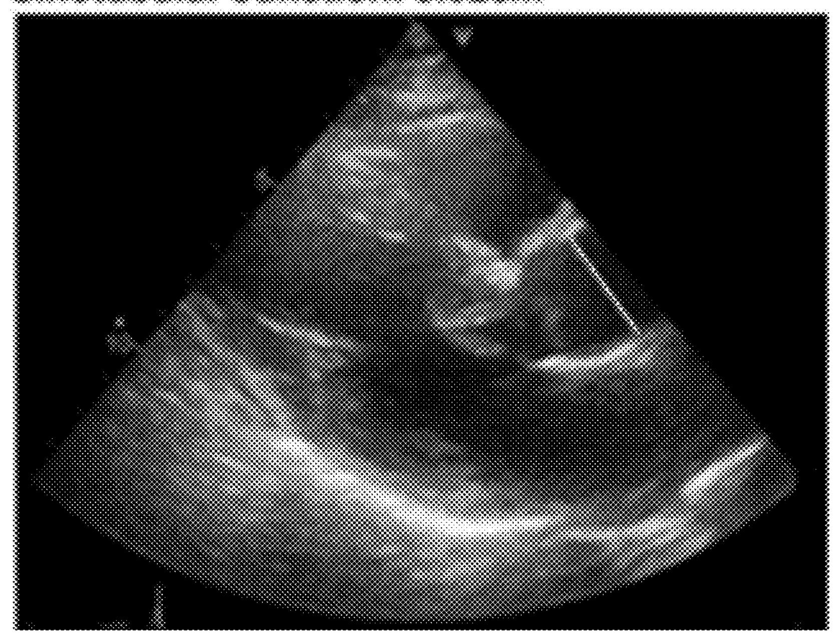
FIG. 46

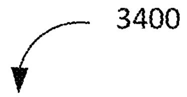
Sinus of Valsalva: 3.47cm
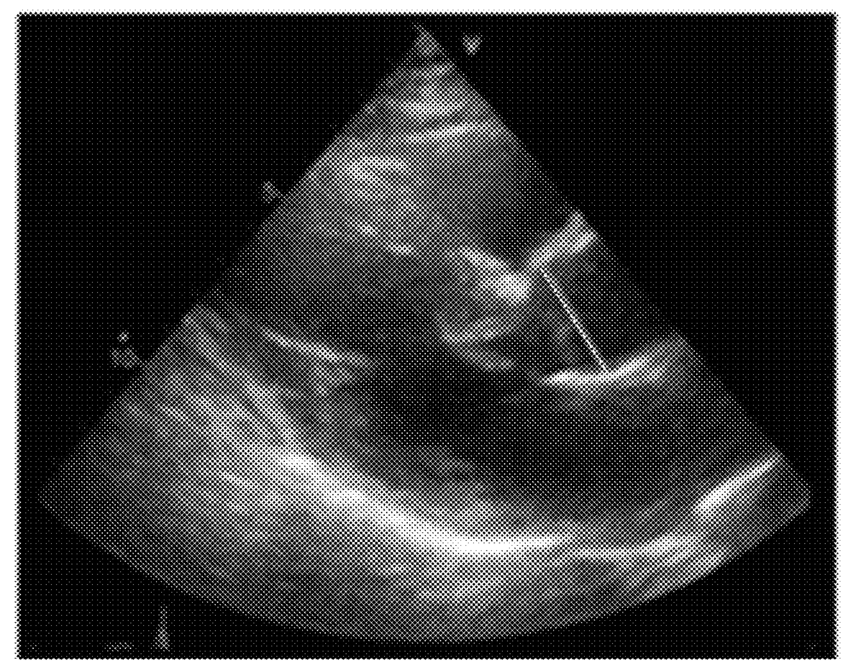
FIG. 47

3400

4802

| Pathology | Echos | Accuracy | ROC AUC |
|---|---|---|---|
| Aortic Stenosis | 820 | 98% | 0.98 |
| Aortic Sclerosis | 1785 | 93% | 0.92 |
| Mitral Valve Calcification | 3087 | 88% | 0.96 |
| Left Ventricle Enlargement | 1473 | 88% | 0.93 |
| Hypokinesis | 3996 | 87% | 0.93 |
| Aortic Root Dilation | 941 | 88% | 0.90 |
| Basal Septal Hypertrophy | 1002 | 96% | 0.91 |
| Atrial Fibrillation | 239 | 95% | 0.97 |
| Pericardia Effusion | 267 | 79% | 0.88 |
| Lung Pulmonary Edema | 351 | 90% | 0.98 |

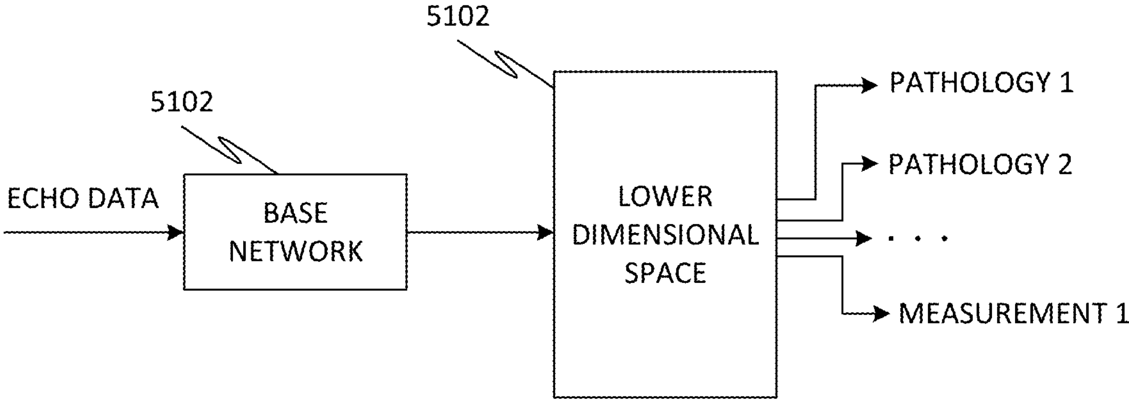
FIG. 51

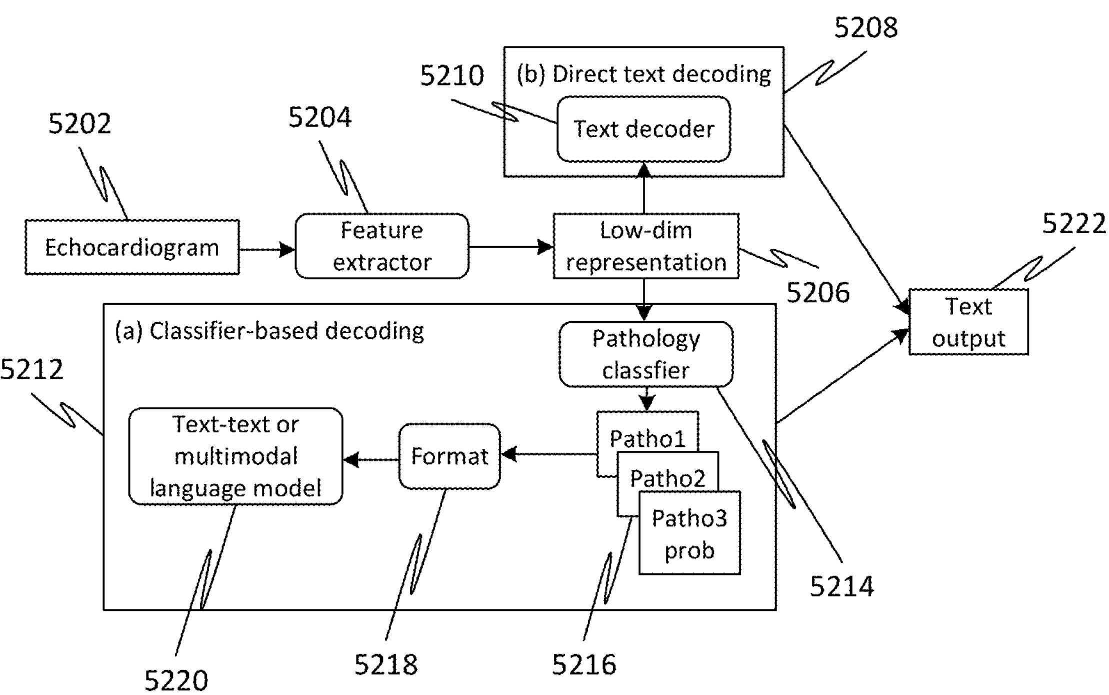
FIG. 52

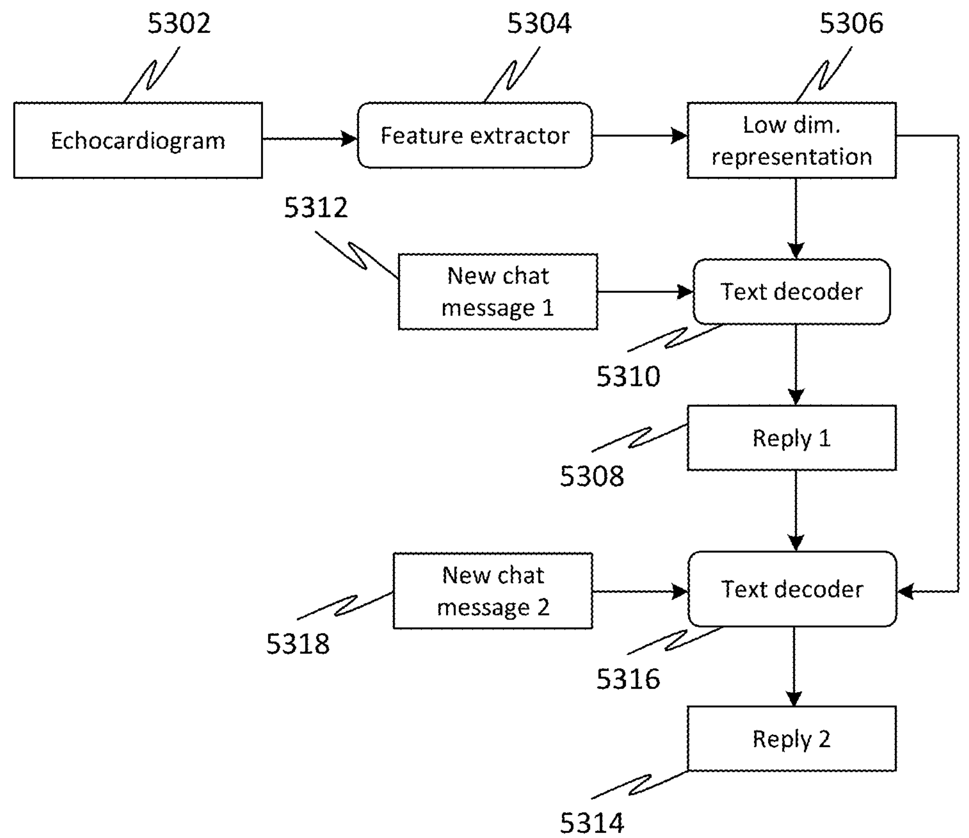
FIG. 53

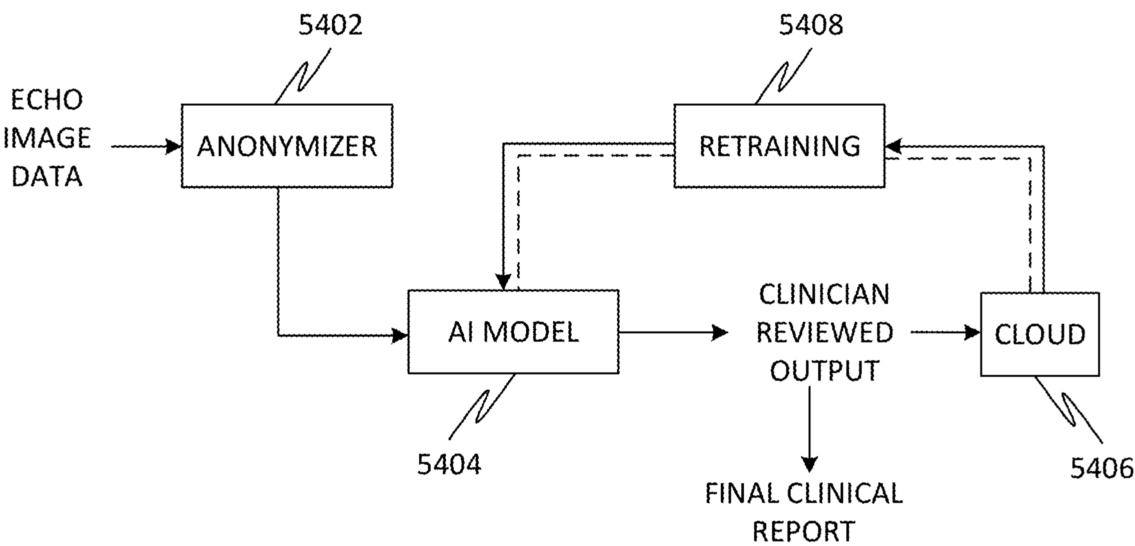
FIG. 54

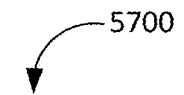
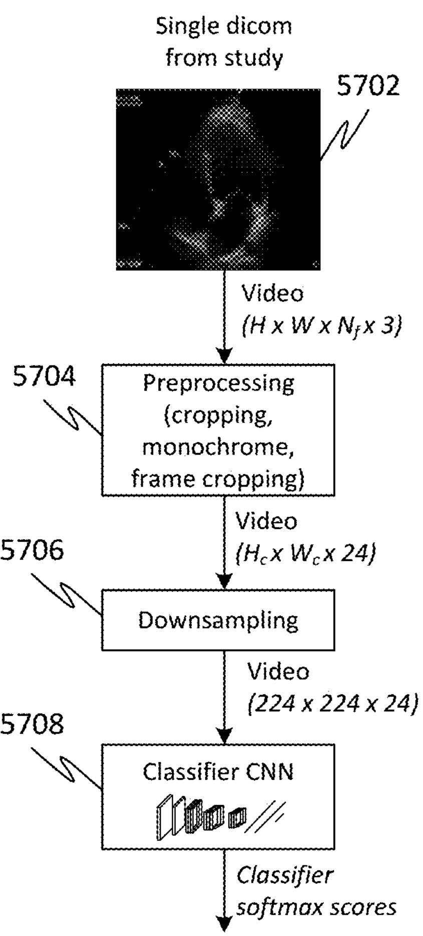
FIG. 57

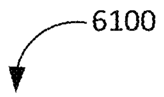
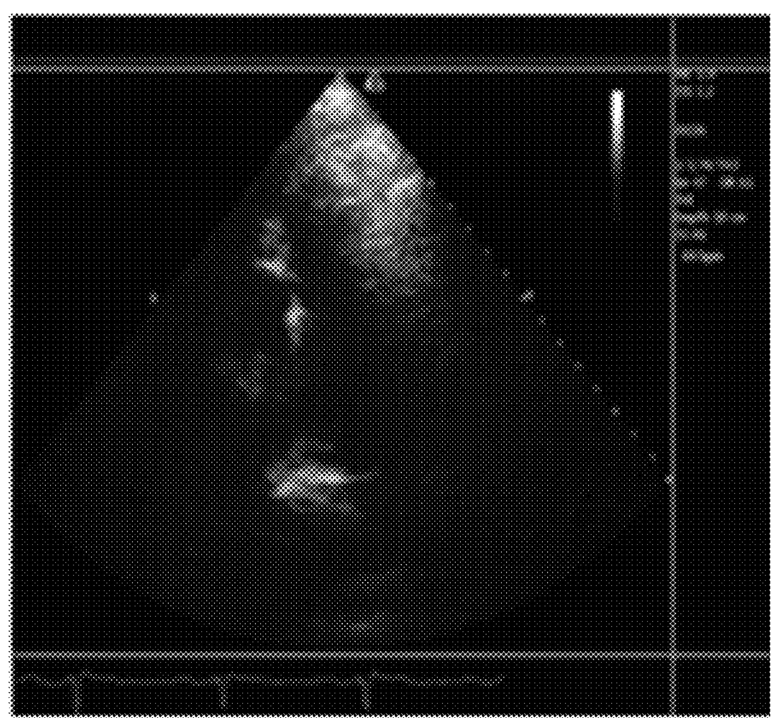
FIG. 61

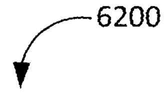
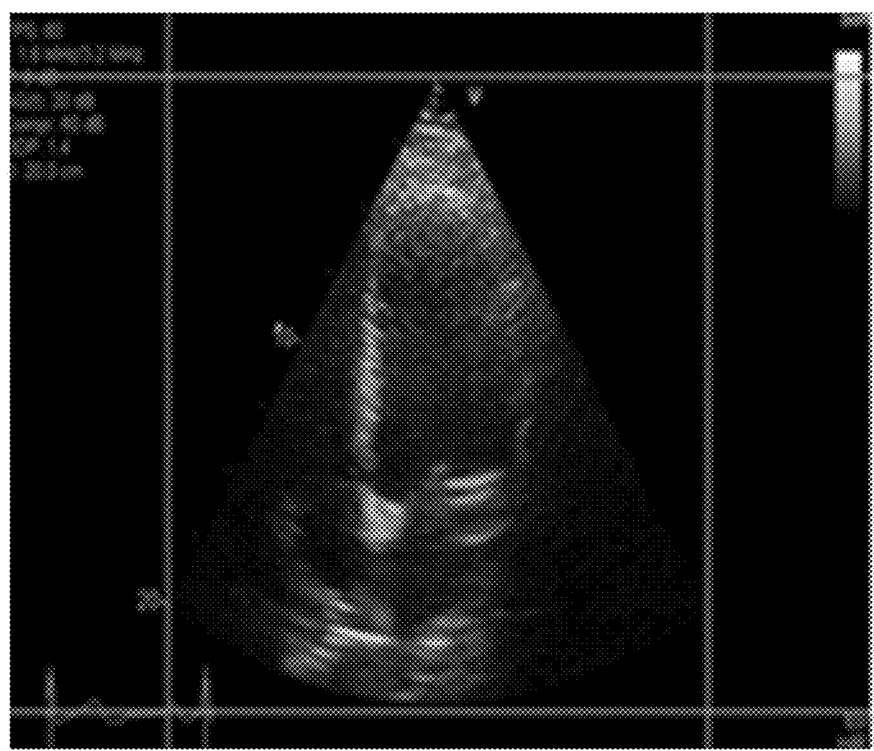
FIG. 62

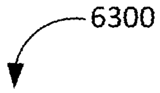
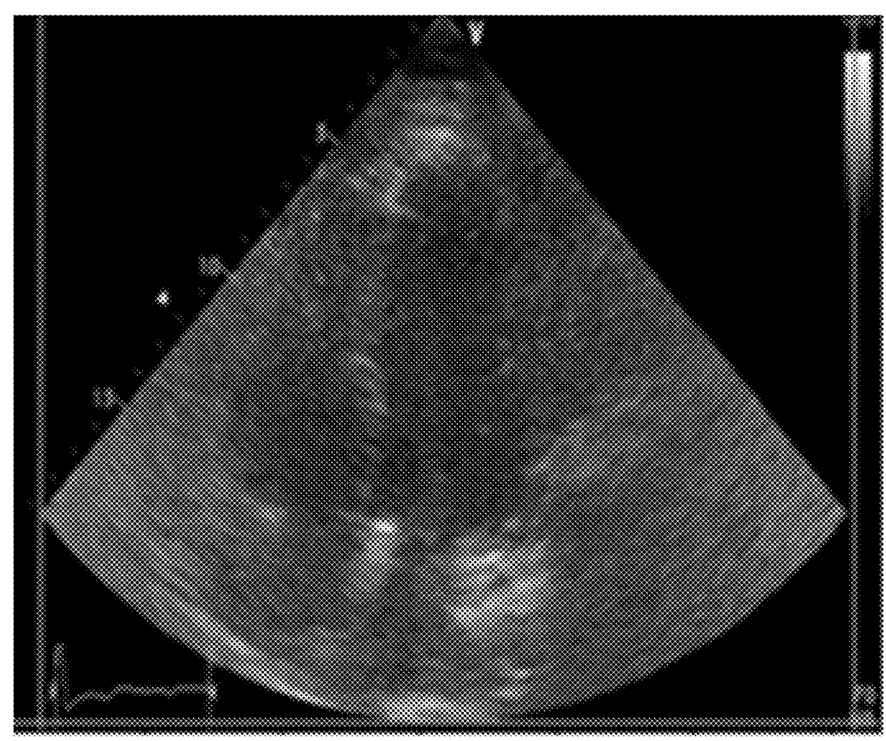
FIG. 63

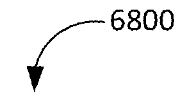
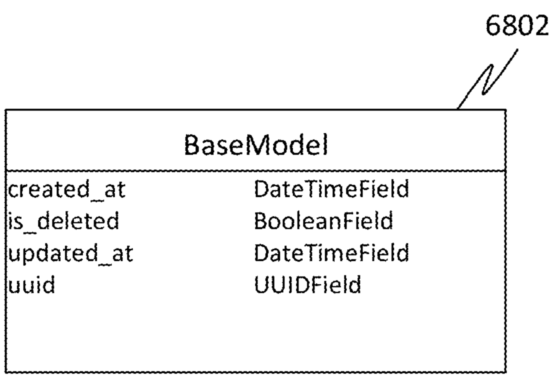
FIG. 68

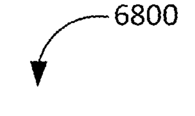
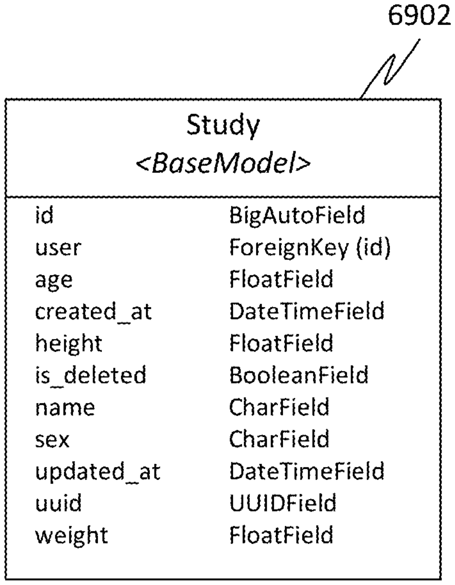
FIG. 69

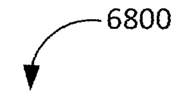
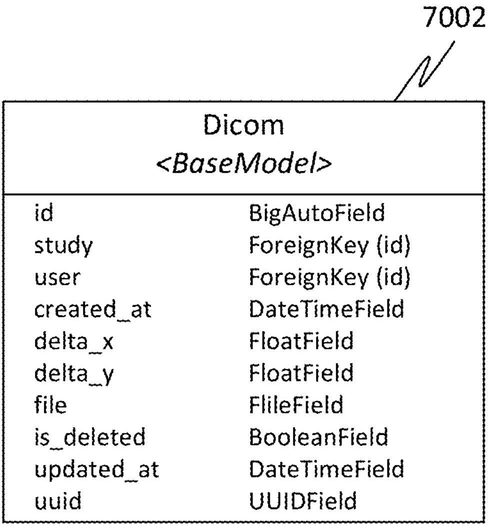
FIG. 70

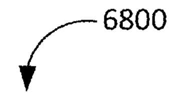
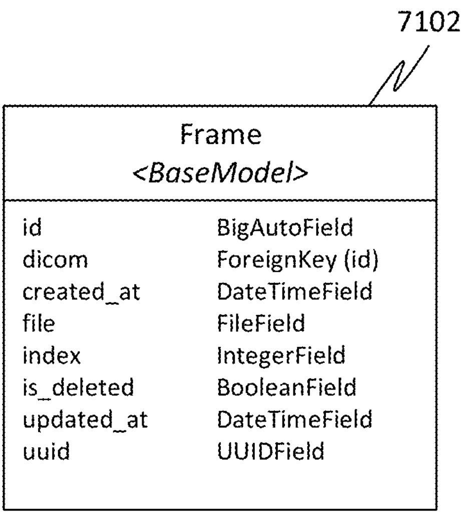
FIG. 71

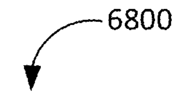
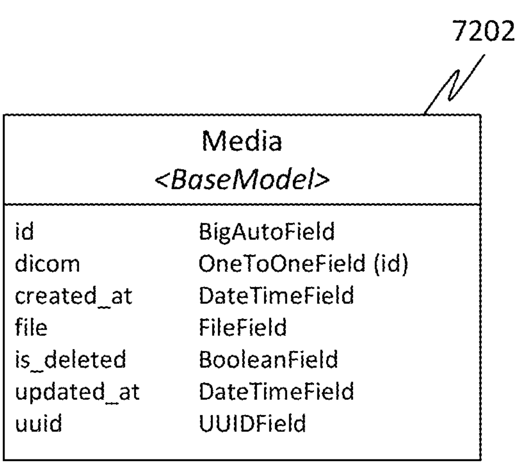
FIG. 72

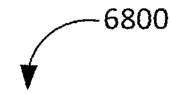
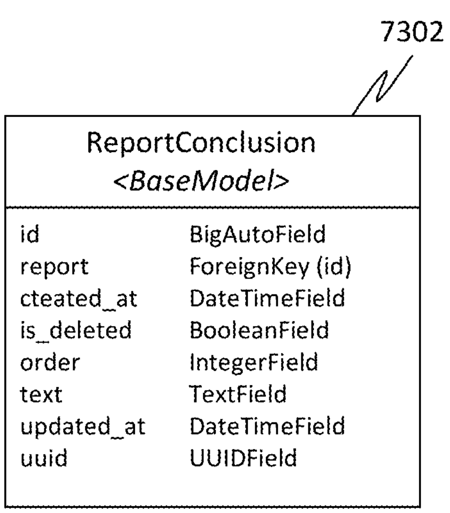
FIG. 73

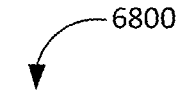
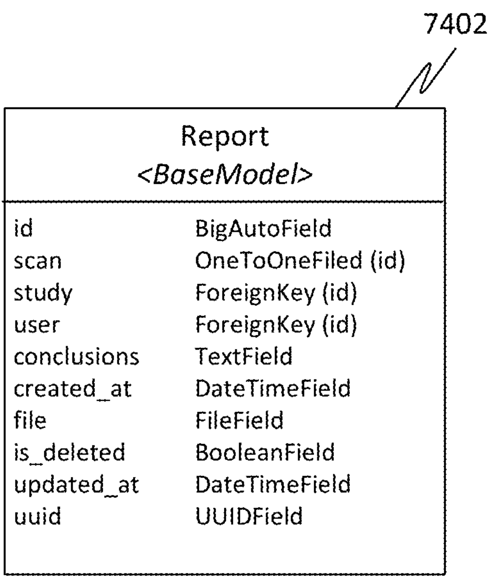
FIG. 74

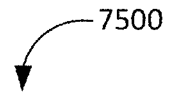
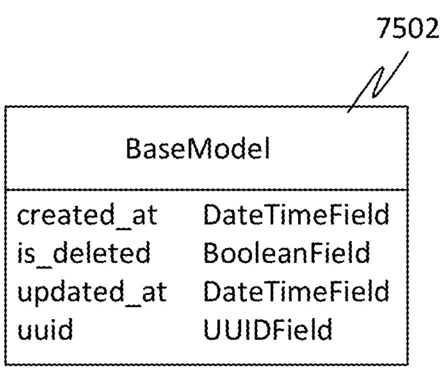
FIG. 75

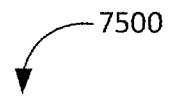
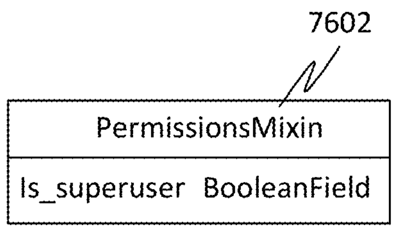
FIG. 76

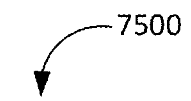
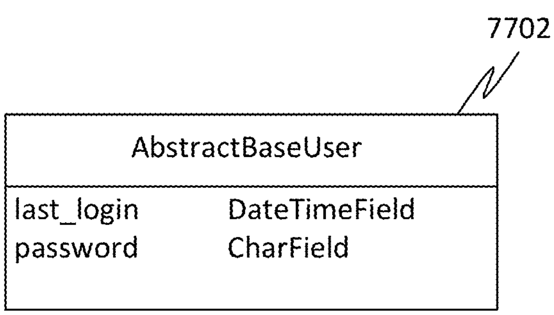
FIG. 77

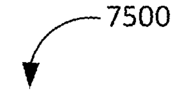
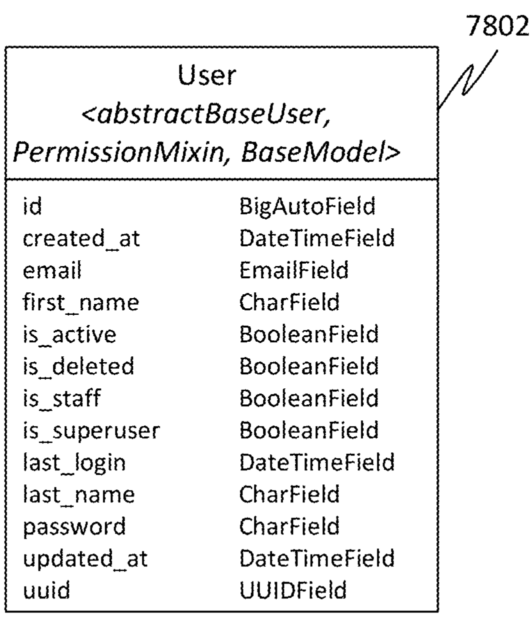
FIG. 78

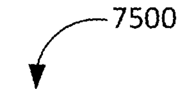
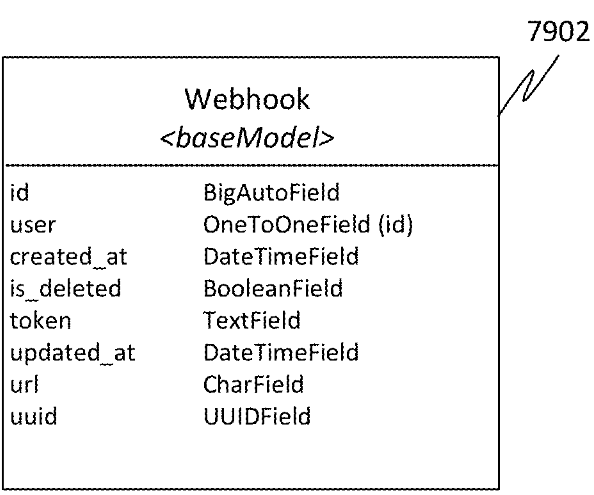
FIG. 79

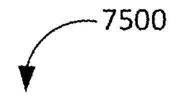
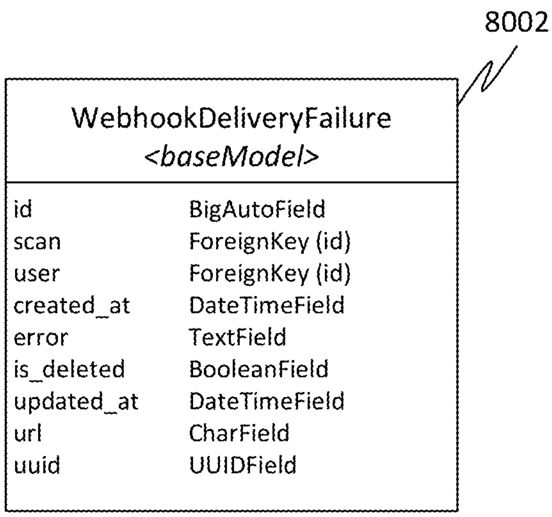
FIG. 80

METHODS, SYSTEMS, APPARATUSES, AND DEVICES FOR FACILITATING A DIAGNOSIS OF PATHOLOGIES USING A MACHINE LEARNING MODEL

CROSS-REFERENCE TO RELATED APPLICATION

This application claims the benefit of U.S. Provisional Patent Application No. 63/441,177, titled "MEDICAL IMAGING SYSTEMS AND METHODS FOR FACILITATING DIAGNOSIS BASED ON MEDICAL IMAGING DATA", filed 26 Jan. 2023, which is incorporated by reference herein in its entirety.

FIELD OF THE INVENTION

Generally, the present disclosure relates to the field of image analysis. More specifically, the present disclosure relates to methods, systems, apparatuses, and devices for facilitating a diagnosis of pathologies using a machine learning model.

BACKGROUND OF THE INVENTION

The field relating to image analysis is technologically important to several industries, business organizations, and/or individuals.

Ischemic heart disease and stroke are leading causes of death, accounting for a combined more than 20 million deaths annually, and have remained the leading causes of death globally in the last 15 years. By 2030, more than 40% of the US population is projected to have some form of Cardiovascular Disease (heart disease).

Currently, existing techniques for facilitating the diagnosis of Cardiovascular diseases (CVDs) are focused on using single deep-learning models for an echocardiogram (ECHO) analysis, pathology detectors, or measurement estimators. Academics have previously made models for many of these pieces individually (e.g. a model for ejection fraction or aortic stenosis), but they never combined them into an end-to-end product that puts together an entire report for the diagnosis of Cardiovascular diseases. Further, the existing techniques rely on Doppler readings to get pulmonary pressure, e/e' ratio, and certain diagnoses on conditions (eg. aortic stenosis, valve regurgitation). However, doppler is not available on certain ultrasound machines (eg POCUS devices). Furthermore, doppler measurements are highly dependent on the quality of obtained Doppler Digital Imaging and Communications in Medicine (DICOM) images. Further, quality DICOM images are difficult to obtain, have high intra-operator variance, and require very skilled sonographers. Furthermore, existing techniques have no quality checks or rely exclusively on the confidence of a viewpoint classifier. If there is no check on image quality, results may be highly erroneous for low-quality DICOM images. Moreover, the existing techniques train models for multiple pathologies in a bespoke manner where each model is trained independently. This is highly impractical when trying to make a comprehensive echo report since there are potentially hundreds of different conditions that may be present.

Therefore, there is a need for improved methods, systems, apparatuses, and devices for facilitating a diagnosis of pathologies using a machine learning model that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is a method for facilitating a diagnosis of pathologies using a machine learning model, in accordance with some embodiments. Accordingly, the method may include a step of receiving, using a communication device, at least one medical data associated with at least one user from at least one device. Further, the method may include a step of analyzing, using a processing device, the at least one medical data using at least one machine learning model. Further, the at least one machine learning model may include at least one artificial neural network comprising a plurality of layers. Further, the plurality of layers may include at least one input layer, a plurality of output layers, and at least one middle layer between the at least one input layer and the plurality of output layers. Further, the at least one input layer may be configured for taking a plurality of medical data as a plurality of inputs to the at least one input layer. Further, the at least one middle layer may be configured for outputting a lower dimensional abstract vector space representation for each of the plurality of inputs by encoding the plurality of medical data to a lower dimensional abstract vector space. Further, the plurality of output layers may be configured for classifying the lower dimensional abstract vector space representation to a plurality of outputs corresponding to a plurality of assessment parameters considered in the diagnosis of the pathologies. Further, each of the plurality of output layers may be configured for communicating each of the plurality of outputs with at least one of the plurality of output layers. Further, each of the plurality of output layers may be configured for adjusting each of the plurality of outputs based on the at least one of the plurality of outputs of at least one of the plurality of output layers. Further, the analyzing of the at least one medical data may include inputting the at least one medical data to the at least one machine learning model. Further, the method may include a step of obtaining, using the processing device, one or more outputs corresponding to one or more assessment parameters from the at least one machine learning model for the diagnosis of one or more pathologies based on the analyzing of the at least one medical data. Further, the method may include a step of generating, using the processing device, at least one result based on the one or more outputs. Further, the method may include a step of storing, using a storage device, the at least one result and the at least one machine learning model.

Further disclosed herein is a system for facilitating a diagnosis of pathologies using a machine learning model, in accordance with some embodiments. Accordingly, the system may include a communication device, a processing device, and a storage device. Further, the communication device may be configured for receiving at least one medical data associated with at least one user from at least one device. Further, the processing device may be communicatively coupled with the communication device. Further, the processing device may be configured for analyzing the at least one medical data using at least one machine learning model. Further, the at least one machine learning model may include at least one artificial neural network comprising a plurality of layers. Further, the plurality of layers may include at least one input layer, a plurality of output layers, and at least one middle layer between the at least one input layer and the plurality of output layers. Further, the at least one input layer may be configured for taking a plurality of medical data as a plurality of inputs to the at least one input layer. Further, the at least one middle layer may be configured for outputting a lower dimensional abstract vector space representation for each of the plurality of inputs by encoding the plurality of medical data to a lower dimensional abstract vector space. Further, the plurality of output layers may be configured for classifying the lower dimensional abstract vector space representation to a plurality of outputs corresponding to a plurality of assessment parameters considered in the diagnosis of the pathologies. Further, each of the plurality of output layers may be configured for communicating each of the plurality of outputs with at least one of the plurality of output layers. Further, each of the plurality of output layers may be configured for adjusting each of the plurality of outputs based on the at least one of the plurality of outputs of at least one of the plurality of output layers. Further, the analyzing of the at least one medical data may include inputting the at least one medical data to the at least one machine learning model. Further, the processing device may be configured for obtaining one or more outputs corresponding to one or more assessment parameters from the at least one machine learning model for the diagnosis of one or more pathologies based on the analyzing of the at least one medical data. Further, the processing device may be configured for generating at least one result based on the one or more outputs. Further, the storage device may be communicatively coupled with the processing device. Further, the storage device may be configured for storing the at least one result and the at least one machine learning model.

Further disclosed herein is a device for facilitating a diagnosis of pathologies using a machine learning model, in accordance with some embodiments. Accordingly, the device may include at least one medical imaging unit, a processing device, and a storage device. Further, the at least one medical imaging unit may be configured for generating at least one medical data associated with at least one user by imaging at least one portion of at least one body part of the at least one user. Further, the processing device may be communicatively coupled with the at least one medical imaging unit. Further, the processing device may be configured for analyzing the at least one medical data using at least one machine learning model. Further, the at least one machine learning model may include at least one artificial neural network comprising a plurality of layers. Further, the plurality of layers may include at least one input layer, a plurality of output layers, and at least one middle layer between the at least one input layer and the plurality of output layers. Further, the at least one input layer may be configured for taking a plurality of medical data as a plurality of inputs to the at least one input layer. Further, the at least one middle layer may be configured for outputting a lower dimensional abstract vector space representation for each of the plurality of inputs by encoding the plurality of medical data to a lower dimensional abstract vector space. Further, the plurality of output layers may be configured for classifying the lower dimensional abstract vector space representation to a plurality of outputs corresponding to a plurality of assessment parameters considered in the diagnosis of the pathologies. Further, each of the plurality of output layers may be configured for communicating each of the plurality of outputs with at least one of the plurality of output layers. Further, each of the plurality of output layers may be configured for adjusting each of the plurality of outputs based on the at least one of the plurality of outputs of at least one of the plurality of output layers. Further, the analyzing of the at least one medical data may include inputting the at least one medical data to the at least one machine learning model. Further, the processing device may be configured for obtaining one or more outputs corresponding to one or more assessment parameters from the at least one machine learning model for the diagnosis of one or more pathologies based on the analyzing of the at least one medical data. Further, the processing device may be configured for generating at least one result based on the one or more outputs. Further, the storage device may be communicatively coupled with the processing device. Further, the storage device may be configured for storing the at least one result and the at least one machine learning model.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

FIG. 4 is a flowchart of a method 400 for facilitating a diagnosis of pathologies using a machine learning model, in accordance with some embodiments.

FIG. 6 is a flowchart of a method 600 for facilitating a diagnosis of pathologies using a machine learning model, in accordance with some embodiments.

FIG. 17 is a table 1700 listing cardia indication and corresponding AUROC for a model, in accordance with some embodiments.

FIG. 28 is a flow diagram of a Training/Validation Data Preprocessing Pipeline 2800 for facilitating diagnosis based on medical imaging data, in accordance with some embodiments.

FIG. 29 is a flow diagram of a pathology (such as HCM) Training Pipeline 2900 for facilitating diagnosis based on medical imaging data, in accordance with some embodiments.

FIG. 30 is a flow diagram of an Inference Pipeline 3000 for facilitating diagnosis based on medical imaging data, in accordance with some embodiments.

FIG. 32 is a flow diagram of a method 3200 for processing a study for facilitating diagnosis based on medical imaging data, in accordance with some embodiments.

FIG. 33 is a screenshot of a user interface 3300 of a iCardio.ai platform for facilitating diagnosis based on medical imaging data, in accordance with some embodiments.

FIG. 34 shows a 'conclusions' 3402 of a iCardio.ai Brain v1 report 3400 produced by the iCardio.ai platform for facilitating diagnosis based on medical imaging data, in accordance with some embodiments.

FIG. 35 is a 'findings' table 3502 of the iCardio.ai Brain v1 report 3400 produced by the iCardio.ai platform for facilitating diagnosis based on medical imaging data, in accordance with some embodiments.

FIG. 36 is a 'measurements' table 3602 of the iCardio.ai Brain v1 report 3400 produced by the iCardio.ai platform for facilitating diagnosis based on medical imaging data, in accordance with some embodiments.

FIG. 37 shows a first image 3702 of 'visualizations' of the iCardio.ai Brain v1 report 3400 produced by the iCardio.ai platform for facilitating diagnosis based on medical imaging data, in accordance with some embodiments.

FIG. 38 shows a second image 3802 of 'visualizations' of the iCardio.ai Brain v1 report 3400 produced by the iCardio.ai platform for facilitating diagnosis based on medical imaging data, in accordance with some embodiments.

FIG. 39 shows a third image 3902 of 'visualizations' of the iCardio.ai Brain v1 report 3400 produced by the iCardio.ai platform for facilitating diagnosis based on medical imaging data, in accordance with some embodiments.

FIG. 40 shows a fourth image 4002 of 'visualizations' of the iCardio.ai Brain v1 report 3400 produced by the iCardio.ai platform for facilitating diagnosis based on medical imaging data, in accordance with some embodiments.

FIG. 41 shows a fifth image 4102 of 'visualizations' of the iCardio.ai Brain v1 report 3400 produced by the iCardio.ai platform for facilitating diagnosis based on medical imaging data, in accordance with some embodiments.

FIG. 42 shows a sixth image 4202 of 'visualizations' of the iCardio.ai Brain v1 report 3400 produced by the iCardio.ai platform for facilitating diagnosis based on medical imaging data, in accordance with some embodiments.

FIG. 43 shows a seventh image 4302 of 'visualizations' of the iCardio.ai Brain v1 report 3400 produced by the iCardio.ai platform for facilitating diagnosis based on medical imaging data, in accordance with some embodiments.

FIG. 44 shows an eighth image 4402 of 'visualizations' of the iCardio.ai Brain v1 report 3400 produced by the iCardio.ai platform for facilitating diagnosis based on medical imaging data, in accordance with some embodiments.

FIG. 45 shows a ninth image 4502 of 'visualizations' of the iCardio.ai Brain v1 report 3400 produced by the iCardio.ai platform for facilitating diagnosis based on medical imaging data, in accordance with some embodiments.

FIG. 46 shows a tenth image 4602 of 'visualizations' of the iCardio.ai Brain v1 report 3400 produced by the iCardio.ai platform for facilitating diagnosis based on medical imaging data, in accordance with some embodiments.

FIG. 47 shows an eleventh image 4702 of 'visualizations' of the iCardio.ai Brain v1 report 3400 produced by the iCardio.ai platform for facilitating diagnosis based on medical imaging data, in accordance with some embodiments.

FIG. 51 illustrates a multi-pathology model 5100 for facilitating diagnosis based on medical imaging data, in accordance with some embodiments.

FIG. 52 is a flow diagram of a method 5200 for facilitating diagnosis based on medical imaging data, in accordance with some embodiments.

FIG. 53 is a flow diagram of a method 5300 for facilitating diagnosis based on medical imaging data, in accordance with some embodiments.

FIG. 54 illustrates a system 5400 for producing clinically relevant measurements and findings, in accordance with some embodiments.

FIG. 57 is a flow diagram of a classification pipeline 5700 facilitating diagnosis based on medical imaging data, in accordance with some embodiments.

FIG. 61 shows a first DICOM image 6100 associated with a plurality of pipelines, in accordance with some embodiments.

FIG. 62 shows a second DICOM image 6200 associated with the plurality of pipelines, in accordance with some embodiments.

FIG. 63 shows a third DICOM image 6300 associated with the plurality of pipelines, in accordance with some embodiments.

FIG. 68 illustrates a 'base model' table 6802 of a clinic module database schema 6800, in accordance with some embodiments.

FIG. 69 illustrates a 'study <base model>' table 6902 of the clinic module database schema 6800, in accordance with some embodiments.

FIG. 70 illustrates a 'DICOM <base model>' table 7002 of the clinic module database schema 6800, in accordance with some embodiments.

FIG. 71 illustrates a 'Frame <base model>' table 7102 of the clinic module database schema 6800, in accordance with some embodiments.

FIG. 72 illustrates a 'Media <base model>' table 7202 of the clinic module database schema 6800, in accordance with some embodiments.

FIG. 73 illustrates a 'Reportconclusion <base model>' table 7302 of the clinic module database schema 6800, in accordance with some embodiments.

FIG. 74 illustrates a 'Report <base model>' table 7402 of the clinic module database schema 6800, in accordance with some embodiments.

FIG. 75 illustrates a 'base model' table 7502 of an authorization module database schema 7500, in accordance with some embodiments.

FIG. 76 illustrates a 'PermissionMixin' table 7602 of the authorization module database schema 7500, in accordance with some embodiments.

FIG. 77 illustrates an 'AbstractBaseUser' table 7702 of the authorization module database schema 7500, in accordance with some embodiments.

FIG. 78 illustrates a 'User<abstractBaseUser, PermissionMixin, BaseModel>' table 7802 of the authorization module database schema 7500, in accordance with some embodiments.

FIG. 79 illustrates a 'Webhook <baseModel>' table 7902 of the authorization module database schema 7500, in accordance with some embodiments.

FIG. 80 illustrates a 'WebhookDeliveryFailure<baseModel>' table 8002 of the authorization module database schema 7500, in accordance with some embodiments.

DETAIL DESCRIPTIONS OF THE INVENTION

Figure 1:
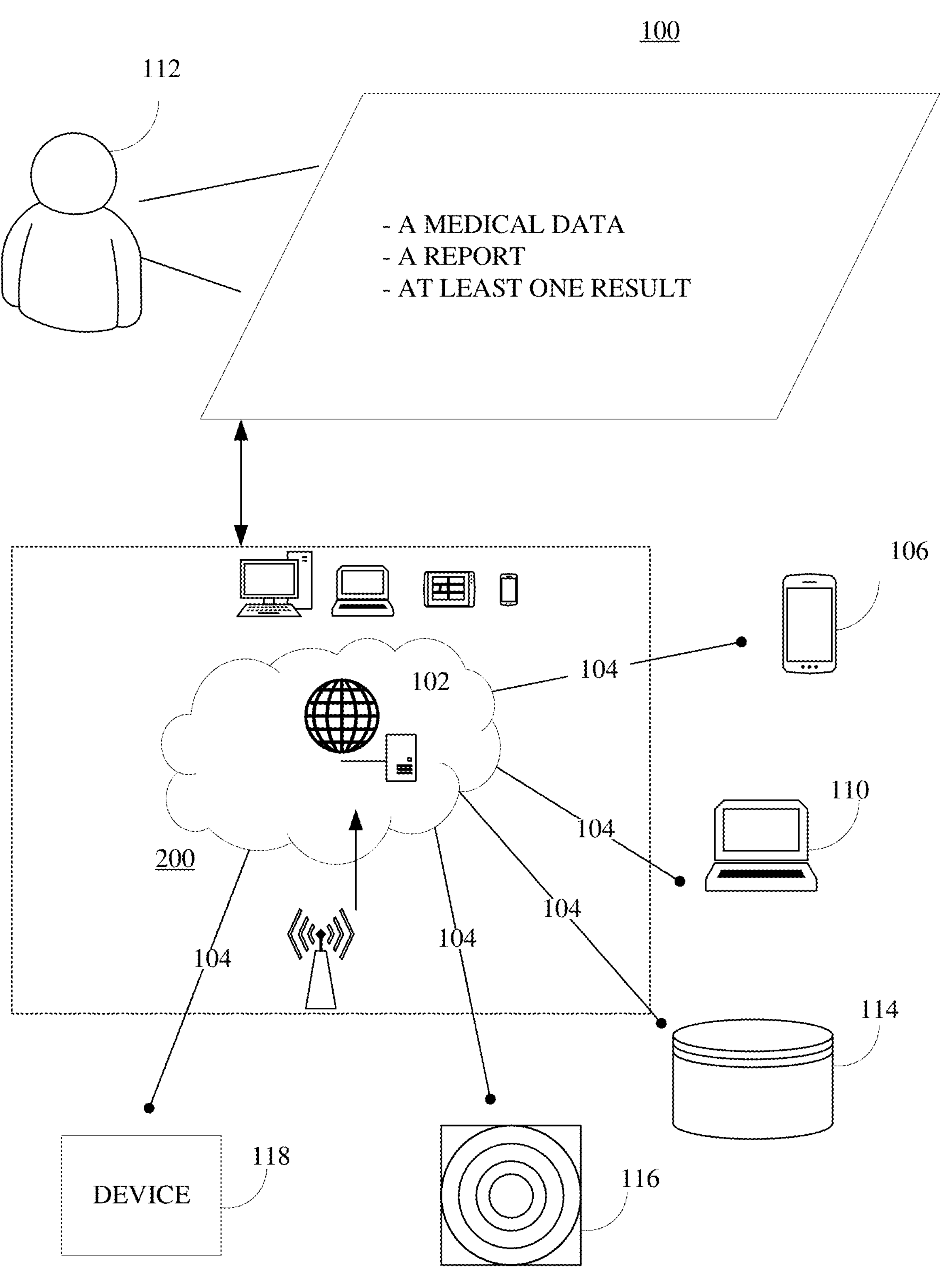
FIG. 1 is an illustration of an online platform 100 consistent with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, “a” and “an” each generally denotes “at least one,” but does not exclude a plurality unless the contextual use dictates otherwise. When used herein to join a list of items, “or” denotes “at least one of the items,” but does not exclude a plurality of items of the list. Finally, when used herein to join a list of items, “and” denotes “all of the items of the list.”

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of methods, systems, apparatuses, and devices for facilitating a diagnosis of pathologies using a machine learning model, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor, and at least one actuator. Examples of the one or more client devices and/or the server computer may include, a desktop computer, a laptop computer, a tablet computer, a personal digital assistant, a portable electronic device, a wearable computer, a smart phone, an Internet of Things (IoT) device, a smart electrical appliance, a video game console, a rack server, a super-computer, a mainframe computer, mini-computer, micro-computer, a storage server, an application server (e.g. a mail server, a web server, a real-time communication server, an FTP server, a virtual server, a proxy server, a DNS server, etc.), a quantum computer, and so on. Further, one or more client devices and/or the server computer may be configured for executing a software application such as, for example, but not limited to, an operating system (e.g. Windows, Mac OS, Unix, Linux, Android, etc.) in order to provide a user interface (e.g. GUI, touch-screen based interface, voice based interface, gesture based interface, etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. One or more external devices may include, for example, but are not limited to, a client device, a third party database, a public database, a private database, and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role based access control, and so on.

Further, one or more steps of the method disclosed herein may be initiated, maintained, controlled, and/or terminated based on a control input received from one or more devices operated by one or more users such as, for example, but not limited to, an end user, an admin, a service provider, a service consumer, an agent, a broker and a representative thereof. Further, the user as defined herein may refer to a human, an animal or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human readable secret data (e.g. username, password, passphrase, PIN, secret question, secret answer etc.) and/or possession of a machine readable secret data (e.g. encryption key, decryption key, bar codes, etc.) and/or possession of one or more embodied characteristics unique to the user (e.g. biometric variables such as, but not limited to, fingerprint, palm-print, voice characteristics, behavioral characteristics, facial features, iris pattern, heart rate variability, evoked potentials, brain waves, and so on) and/or possession of a unique device (e.g. a device with a unique physical and/or chemical and/or biological characteristic, a hardware device with a unique serial number, a network device with a unique IP/MAC address, a telephone with a unique phone number, a smartcard with an authentication token stored thereupon, etc.). Accordingly, the one or more steps of the method may include communicating (e.g. transmitting and/or receiving) with one or more sensor devices and/or one or more actuators in order to perform authentication. For example, the one or more steps may include receiving, using the communication device, the secret human readable data from an input device such as, for example, a keyboard, a keypad, a touch-screen, a microphone, a camera, and so on. Likewise, the one or more steps may include receiving, using the communication device, the one or more embodied characteristics from one or more biometric sensors.

Further, one or more steps of the method may be automatically initiated, maintained, and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g. the server computer, a client device, etc.) corresponding to the performance of the one or more steps, environmental variables (e.g. temperature, humidity, pressure, wind speed, lighting, sound, etc.) associated with a device corresponding to the performance of the one or more steps, physical state and/or physiological state and/or psychological state of the user, physical state (e.g. motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g. a real-time clock), a location sensor (e.g. a GPS receiver, a GLONASS receiver, an indoor location sensor etc.), a biometric sensor (e.g. a fingerprint sensor), an environmental variable sensor (e.g. temperature sensor, humidity sensor, pressure sensor, etc.) and a device state sensor (e.g. a power sensor, a voltage/current sensor, a switch-state sensor, a usage sensor, etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview

The present disclosure describes methods, systems, apparatuses, and devices for facilitating a diagnosis of pathologies using a machine learning model. Further, the systems may include medical imaging systems. Further, the diagnosis of the pathologies may be based on the medical imaging data.

Further, the present disclosure describes an artificial intelligence (AI)-based platform. Further, the artificial intelligence (AI)-based platform may be developed by iCardio.ai. Further, the AI based platform may include an inference platform and a training platform. Further, the inference platform is the iCardio.ai Brain and the training platform may be iCardio.ai. AI platform. Further, the iCardio.ai. AI platform may leverage a database of a large number of individual echocardiographic images for analysis of echocardiographs. Further, the AI based platform may implement echocardiography machine learning for performing echocardiography diagnosis. Further, the iCardio.ai. may provide automated echocardiography. Further, the artificial intelligence (AI)-based platform may require minimal human intervention and may ensure the prevention of misdiagnoses and underdiagnoses of cardiac disorders. Further, the artificial intelligence (AI)-based platform may validate a large number of different cardiac anomalies. Further, the artificial intelligence based platform may be integrated into existing handheld ultrasound devices. Further, the AI based platform may be accessible to novices in outpatient and non-clinical settings. Further, the AI based platform may be incorporated into a hardware device of a 3-d party hardware manufacturer which may be used for diagnosing multiple cardiac ailments with high accuracy and speed.

Further, iCardio.ai aims to develop and test algorithms. Further, the algorithms may enable the detection of multiple different pathologies (such as HCM). Further, the algorithms may assess its severity by scoring for underlying symptoms as "none", "mild", "moderate" and "severe". Further, iCardio.ai may develop an AI-based model for the interpretation of multiple different pathologies. Further, the AI-based model may be validated for the accuracy and precision of multiple different pathologies diagnoses from echocardiograms. Further, additional parameters such as speed and ease of diagnosis may be tested. Further, the AI-based model may be incorporated into emergency and ambulatory care, mass health screening, military recruitment, and also in remote areas where resources and manpower required for standard health inspections may be scarce or unavailable.

Further, iCardio.ai may be developing AI based diagnostic tools. Further, the AI based diagnostic tools may enable the detection of pathologies (such as HCM). Further, the AI based diagnostic tools may assess the pathologies' (such as HCM) severity. Further, the AI based diagnostic tools may facilitate fast and accurate interpretation of echocardiograms for the detection of pathologies (such as HCM) even by novice users.

Further, the present disclosure describes an artificial intelligence (AI)-based platform (iCardio.ai Brain) for the fast and accurate interpretation of echocardiograms thereby reducing the need for human intervention, which is developed by iCardio.ai. Further, the AI-based platform may be configured for diagnosing cardiac anomalies using echocardiograms. Further, the artificial intelligence (AI)-based platform may facilitate diagnosing both symptomatic and asymptomatic HCM. Further, the artificial intelligence (AI)-based platform may assess HCM's severity to support clinicians with a high-quality, automated interpretation of echocardiograms. Further, the AI based platform of iCardio.ai leverages a database of a large set of individual echocardiographic images. Further, the iCardio.ai.Brain may be designed with specific machine learning algorithms trained for automated interpretation of cardiac anomalies from echocardiograms and thus supporting the clinical diagnosis. Further, the iCardio.ai may develop and test algorithms that may enable the detection and severity grading of the HCM).

Further, the present disclosure describes the development of an AI-based model for the interpretation of pathologies (such as HCM). Further, the iCardio.ai may be using B-mode images from trans-thoracic echocardiography (TTE) records of patients across the United States. Further, the trans-thoracic echocardiography records may be de-identified and anonymized. Further, the trans-thoracic echocardiography (TTE) records may be obtained from a data provider. Further, the trans-thoracic echocardiography (TTE) records may get curated by annotators. Further, each trans-thoracic echocardiography (TTE) record may be stratified as "None", "Mild", "Moderate", and "Severe" depending on the physician's notes for pathologies (such as HCM) severity which gives the ground truth labels for pathologies (such as HCM). Further, the curated trans-thoracic echocardiography (TTE) records may be divided into two sets. Further, one set may be used for training and the other set for validation. Further, the iCardio.ai may develop algorithms for training models to detect and score pathologies (such as HCM). Further, the models may include an end-to-end HCM model which may be fused with iCardio.ai's proprietary anatomical measurement models of metrics traditionally indicative of pathologies (such as HCM), to further improve performance. Further, the criteria for success for the development of the AI based model for the interpretation of pathologies (such as HCM) may be an Area Under the Receiver Operating Characteristic curve (AUROC) of 0.88 with 80% sensitivity and specificity, and an F1 score>0.85.

Further, the present disclosure describes a validation of the AI-based model to assess the accuracy and precision of pathologies (such as HCM) diagnosis. First, the hold-out (testing) set (20% of images/patient records) will be used for retrospective validation to assess how well the model will perform on unseen data. Subsequently, three additional labels on retrospective data from echocardiographers of varying experience are obtained with and without AI assistance. This will be used to measure inter-clinician and intra-clinician variability and measure how much accessing the AI results improved clinician agreement. Further, the criteria for success for the validation of the AI based model may be AUROC of >0.88.

Further, the present disclosure describes an algorithm proposed by iCardio.ai that may enable rapid and accurate diagnosis of symptomatic and asymptomatic pathologies (such as HCM). Further, the algorithm may assess the severity of the pathologies (such as HCM). Further, the algorithm may reduce misdiagnosis and underdiagnosis of the disease. Further, the algorithm may be used for diagnosis. Further, the algorithm may have the ability to be integrated into the existing hand-held ultrasound devices. Further, the integration of the algorithm into the existing hand-held ultrasound devices may enable it to be used in emergency care, ambulances, and also in remote areas where resources and manpower required for standardized inspection may be scarce or unavailable. Further, the time and expenses involved in extensive training of echocardiographers may also be brought down drastically. Further, the algorithm may need a minimally trained ultrasound technician to assess the echocardiograms and prompt medical attention may be provided to critical patients. Further, the above mentioned features may reduce the cost of diagnosis of cardiac ailments.

Further, the present disclosure describes an artificial intelligence AI-based platform developed by iCardio.ai. Further, the artificial intelligence AI-based platform may be configured for the fast and accurate interpretation of echocardiograms. Further, the artificial intelligence AI-based platform may be capable of diagnosing both symptomatic and asymptomatic pathologies (such as HCM). Further, the AI-based platform may support clinicians with a high-quality, and automated interpretation of echocardiography scans including both diagnosis and scoring of disease severity.

Further, the present disclosure describes iCardio.ai's technology. Further, the iCardio.ai may have standardized data collection and image annotation requiring the usage of AI in echocardiography. Further, the data and image may be used for training models for the detection of various cardiac indications such as atrial fibrillation, aortic stenosis, etc. Further, the iCardio.ai may use a dataset of echocardiography studies for the training of one or more machine learning models. Further, the iCardio.ai may focus on training and validation of a comprehensive deep learning system for the automated detection and the scoring of the severity of pathologies (such as HCM) using echocardiographic data.

Further, the present disclosure describes iCardio.ai's AI-integrated platform (AI based platform) for echocardiography that may enable rapid and accurate diagnosis and scoring of the severity of symptomatic and asymptomatic pathologies (such as HCM). Furthermore, iCardio.ai's AI-integrated platform may reduce errors in terms of misdiagnoses and underdiagnoses of pathologies (such as HCM). Further, iCardio.ai's AI-integrated platform may increase accessibility since it may be applied in non-cardiac or emergency departments, where a swift diagnosis is often required in the absence of an expert echocardiographer. The ease of integration of this platform into existing hand-held ultrasound devices also enables it to be used in remote areas where the resources and manpower required for conducting routine medical check-ups may be scarce or unavailable. Furthermore, it can greatly reduce the cost of diagnosis, thus making echocardiography more easily available to the general population.

Further, iCardio.ai has a privately owned database of annotated echocardiography studies. Furthermore, iCardio.ai aims to reproduce the entire preliminary cardiologist report. This report includes multiple validated pathology models as well as multiple anatomical and physiological measurement models.

Further, the iCardio.ai's AI-based platform may have the ability to integrate into existing and new echocardiography hardware and picture archiving and communication systems (PACS). Further, iCardio.ai's software may be integrated into the echocardiography hardware and PACS, and end-user of this hardware and systems may be charged based on a subscription-based pricing model.

Further, the present disclosure describes an AI-integrated platform developed by iCardio.ai for accurate diagnosis and severity classification of pathologies (such as HCM). Further, the AI-integrated platform may include a Deep neural network (DNN) architecture. Further, the AI-integrated platform may be video based, therefore detecting even the mildest cardiac defects. Further, a Convolutional Neural Network (CNN) of the AI-integrated platform may merge cardiac measurements with end-to-end pathology models using a wide and deep CNN, which increases both accuracies as well as explainability. Further, iCardio.ai's model may stratify the severity of the disease as one of mild, moderate, and severe as opposed to an existing algorithm that can merely detect the presence or absence of the disease. Further, the stratifying of the severity of the disease as mild/moderate/severe may allow for the detection of hard to diagnose cases and enable appropriate and timely medical support. Further, the curated database of iCardio.ai consists of a large set of clinically annotated studies and may be heterogeneous with regard to device type, reviewing cardiologists, geographic location, age, and image quality. Further, the greater number of annotated studies may enable better training of the models and ensure higher generalizability in the real world. Further, the algorithm may be integrated into all existing standards and the handheld point-of-care ultrasound (POCUS) echocardiographic devices, thus avoiding additional expenditure for the users. The ease of use of this platform also ensures that it can be easily used in emergencies by minimally trained personnel like paramedic staff or general practitioners and can also be deployed in remote locations where specialty medical care facilities may be unavailable. The speed of detection (<1 s) aids its use for mass medical screening, for instance in medical check-ups for military settings where it can detect even asymptomatic cardiac conditions. The swift diagnosis, as well as the ability to assess the severity of the disease, also facilitates appropriate and timely medical treatment to be provided to the patient, thus preventing life-threatening conditions. Further, iCardio.ai's AI based platform increases the availability of echo interpretation and assists clinicians by providing insights into measurements, diseases, and conditions that may otherwise go missing. Most importantly, iCardio.ai's AI based platform has a greater array of models available for disease detection.

Further, the present disclosure describes iCardio.ai. Brain, which is an AI based platform developed by iCardio.ai. Further, the iCardio.ai. Brain automates the interpretation of cardiac anomalies from echocardiograms and supports the clinical diagnosis. Further, the iCardio.ai. Brain may comprise multiple artificial intelligence (AI) algorithms (deep learning models) for the estimation of anatomical measurements, physiological measurements, and pathologies. Further, the anatomical measurements may include a left ventricular volume, etc. Further, the physiological measurement may include an ejection fraction, etc. Further, the pathologies may include Aortic Stenosis, etc, as shown in FIG. 17. Further, iCardio.ai's technology may be used for the development of DNN models for the pathologies (such as HCM). Further, the DNN models may be validated using a retrospective non-interventional study, and a preliminary prospective study. Further, iCardio.ai may be able to collate a highly diverse and unique database of echocardiography studies. Further, the dataset has been used to train all the models. Further, the DNN models process raw DICOM videos using deep neural networks. Further, a preliminary search of iCardio.ai's database indicates over 1200 HCM cases. Further, iCardio.ai may not have developed an explicit tool for HCM, several of its previously developed models estimate measurements and pathologies correlated with HCM. Further, a sample output of iCardio.ai's measurement model for predicting LV wall thickness is shown in FIGS. 24-27. LV wall thickening is a key feature of Hypertrophic Cardiomyopathy. In addition to explicitly measuring wall thickness, iCardio.ai has developed models to predict Basal Septal Hypertrophy with an AUROC of 0.91. Furthermore, the iCardio.ai may have thirty pathology models. Further, twenty-one out of the thirty pathology models may be determined to be clinically viable as they have an AUROC of >0.88. Further, using transfer learning, one or more of these models may be trained successfully using under 300 positive cases based on the transfer learning.

Further, the iCardio.ai may achieve a robust model for pathology (such as HCM) based on the preliminary data for other cardiac anomalies.

Further, the iCardio.ai aims to develop newer algorithms for faster and more accurate detection of pathologies (such as HCM), along with scoring of disease severity. The AI based platform developed by iCardio.ai is envisioned to provide clinicians and less trained technicians, especially in medical emergencies, with a high-quality, automated, and rapid tool for the interpretation of echocardiograms of patients suffering from pathologies (such as HCM). The model will be trained for severity classification of pathologies (such as HCM) as “none”, “mild”, “moderate” or “severe”. The diagnostic performance of the platform will be assessed based on predictive performance on a hold-out (validation) set as measured by AUROC.

Further, iCardio.ai may have a heterogeneous dataset on which patient de-identification and anonymization have been carried out. Further, the AI based platform may run one or more automated protocols for training deep learning models. Further, the end-to-end models may be trained in two or more views. Further, the dataset may be randomly separated into a training set and a testing set. Further, the training set may comprise 80% of the data associated with the dataset. Further, the testing set may comprise 20% of the data associated with the dataset. Further, the training set may be used to train the algorithm for pathologies (such as HCM) detection. Further, the testing dataset may be used for hold-out validation of the trained algorithm.

Further, the present disclosure describes a curation of the data set. Further, the iCardio.ai may use B-mode images from trans-thoracic echocardiography (TTE) records of patients across the United States. Further, freeform physician notes are parsed into fixed stratification categories and collect linear measurement data. Further, the curating of the Data set may be based on a data curation workflow (as shown in FIG. 28). Further, the data curation may start with a study that includes a series of videos such as DICOMs, etc. from different angles of the heart. Further, each DICOM may include a physician's notes. Further, after anonymizing the DICOMs, the view of the heart may be automatically identified from among multiple different views. Further, a trained technician may review previously collected freeform notes from the original reviewing cardiologist and stratify each study as “None”, “Mild”, “Moderate”, and “Severe” with regards to the pathologies (such as HCM) severity. These labels will be used as the ground truth for follow-on model training. It should be noted that once a “study”, defined as a set of DICOMs collected in the same session, is labeled as indicating pathology, all DICOMs in that study, from multiple views, are also labeled as ‘indicating pathology. This enables the ability to easily train models for multiple views. Only medium to high-quality videos will be used. Video quality will be determined by iCardio.ai's previously developed DNN-based quality classifier. The collected data will be reviewed by the advisors to meet standards and then used in follow-on training and validation.

Further, the present disclosure describes the development of algorithms and training of the model for pathologies (such as HCM). Further, iCardio.ai develops algorithms to identify the pathologies (such as HCM) severity from raw DICOM data. The training set will be used by the algorithm for training the model for pathologies (such as HCM) detection. In each training iteration, the algorithm receives and evaluates data from the training set to provide a severity classification of “None”, “Mild”, “Moderate” and “Severe”. The predicted label is then compared to the ground truth label via the loss function. Finally, the backpropagation algorithm is used to adjust network weights so as to minimize the loss function. This process is repeated over multiple (potentially hundreds of thousands) iterations until performance no longer improves.

Once the training process is completed, the following models will be trained:

i. Video-based End-to-End pathology (such as HCM) Model: This model predicts pathology (such as HCM) propensity directly from DICOM video data. It takes as input a height×width×$N_{frames}$ tensor and outputs a scalar indicating pathology (such as HCM) severity. The model will be exclusively developed for diagnosing pathology (such as HCM) and scoring the severity. The videos from the database are down-sampled (size reduction), and views are randomly selected and subjected to random augmentations, like changes in brightness, contrast, etc. This data will be then used by the neural network for the machine learning and development of the model.

ii. Measurement models to estimate metrics traditionally indicative of pathology (such as HCM): These previously developed, proprietary models take a single frame as input and output a scalar indicating the relevant measurement length, in physical units (e.g., cm for Intraventricular Septum length, or $cm^3$ for left ventricle volume). Further, iCardio.ai will determine which anatomical and physiological measurements contribute the most to predicting pathology (such as HCM).

iii. Ensemble model which fuses models from (i) & (ii): This model is a fusion of the Video-Level End-to-End model and Measurement model. The pathology (such as HCM) propensity score and estimated measurements will be fused using a “wide” 2-layer multi-level perceptron (MLP). The pathology propensity model and the wide MLP will be trained jointly. The measurement extraction models, on the other hand, will have their weights fixed, as they have already been previously trained. Further, the pathology (such as HCM) training pipeline is shown in FIG. 29.

Further, to determine the rigor of the study Pearson's correlation will be used for key point models. The AUROC of the pathology (such as HCM) algorithm should be above 0.88 to match the FDA predicate. Further, a heterogeneous dataset is an expected outcome, which comprises curated high-quality echocardiograms of over 1000 patients. With this dataset, the pathology (such as HCM) algorithm will be trained to develop an end-to-end, wide-and-deep model for pathology (such as HCM) detection with an AUROC of 0.88 (metrics accepted by the FDA for a comparable classifier). Further, a pathology (such as HCM) algorithm successfully trained for pathology (such as HCM) image analysis and interpretation is attained. Criteria for the success of the pathology (such as HCM) algorithm may be AUROC of 0.88 with 80% sensitivity and specificity. If expected accuracy and sensitivity are not attained—iCardio.ai will (i) further clean and curate the existing datasets (ii) obtain more patient data from other data partners and (iii) intelligently combine predictions from models trained on multiple views of the heart. Once the pathology (such as HCM) model has been developed, it needs to be validated. This will be carried out in two steps. Primarily, the hold-out (testing) set (20% number of images/patient records) will be used for retrospective validation to assess how well the model will perform on unseen data. Subsequently, iCardio.ai will obtain three additional labels on retrospective data from echocardiographers of varying experience with and without AI assistance. This will be used to (1) measure inter-clinician and intra-clinician variability and (2) measure how much viewing the AI results improved clinician agreement. Further, the analysis and protocol here will closely follow FDA approved pathology diagnostic support system for echocardiography for coronary artery disease (CAD).

Further, the present disclosure describes a Retrospective Validation with hold-out datasets. The deep learning model for pathology (such as HCM) will be evaluated using specific metrics (AUROC and F1 score) which ensure accuracy (defined as the degree to which it conforms to the correct value or standard). For each data/image, the model predictions will be compared to the ground-truth data, or expert-labeled data, defined as the original annotations of the clinicians who inspected the echo study. The accuracy of the pathology (such as HCM) model would be defined as the percentage of the times the model predictions match the ground-truth label, according to a) ROC curve which will represent true positive rate (TPR) and false-positive rate (FPR). TPR is defined as follows: TPR=TP/(TP+FN), where TP is the count of true positives, FN is the count of false negatives, and False Positive Rate (FPR) is defined as follows: FP/(FP+TN), where FP is the count of false positives and TN is the count of true negatives. The AUROC is the area under the ROC curve b) F1 Score, which is the harmonic mean between precision and recall (i.e. 2*(precision*recall)/(precision+recall)). Precision is defined as TP/(TP+FP). The recall is defined as TP/(TP+FN). The recall is equivalent to the TPR. Further, the workflow is shown in FIG. 30.

Further, the present disclosure describes an Initial prospective validation of the model for pathology (such as HCM) with Level III echocardiographers. Further, iCardio.ai's pathology (such as HCM) dataset contains only a single label by a level III echocardiographer. For this task, a specific protocol is followed and three additional labels for each pathology (such as HCM) study are obtained from other echocardiographers of varying experience. During the data collection process, the clinician is presented with the echo images twice. The first time, 50% of images will be accompanied by a report containing information on whether the AI had classified the patient as having pathology (such as HCM). Clinicians will be informed that the AI-based classification is not 100% accurate and will be free to choose whether to use the AI result in their clinical interpretation. After a 1-month washout period, all clinicians will be shown the study images again, but this time with the AI report provided for the other 50% of studies. After each study, the readers will be also asked to provide a binary (confident or not confident) measure of their confidence in their clinical interpretation of the study. Further, ROC curves and AUROC for reads with and without AI assistance will be used to quantify improved performance from the AI, as the rigor of the study. Further, iCardio.ai expects to have the pathology (such as HCM) model to perform with an AUROC of >0.88 to enable its acceptance by the FDA based on the predicate device, as expected outcomes. Further, A general performance threshold of the model to perform with AUROC>0.88 is achieved. If the proposed model is unable to diagnose pathology (such as HCM) with 0.88 AUROC, more data on patients will be collected in collaboration with an external researcher to better train the model to get closer to the performance goal. Other models will be tried, such as video-based temporal models (as opposed to image-based models). Additionally, the studies with the biggest discrepancies between the model and clinician will be identified, and those will be reassessed by another clinician. If the second clinician's interpretation agrees with the first one's then it means the model is inaccurate. If it differs, the interpretation by a third clinician would be considered to break the tie. In cases where the first clinician was wrong, the corrected label will go into the updated dataset to retrain and revalidate the model. Parameters like speed and ease of diagnosis will be assessed.

For the development and implementation of AI based platform, iCardio.ai requires and is equipped with a full set of high-performance computing hardware (six high performance machines) and software libraries/frameworks for the rapid development of advanced analytics and machine learning algorithms. The computing hardware includes an AMD DigitalStorm Ryzen 7 5800X 8-Core Processor and NVIDIA RTX 3080 GPU and multiple other servers featuring NVIDIA RTX 2000 and 3000 series GPUs. iCardio.ai also actively uses AWS tools such as SageMaker, EC2, and S3 for model training and optimization. The software includes open-source, multi-platform (Windows/Linux) software libraries such as OpenCV for image/video processing, TensorFlow/PyTorch for deep learning, scikit-learn for machine learning, and ClearML for MLOps and batch model training. iCardio.ai maintains best practices of modern software engineering including version control (Git), unit testing (PyTest), issue tracking, and agile project management (Azure DevOps). Critically, iCardio maintains an internally developed ISO 13845 compliant Quality Management System (QMS) for document control, design control, verification, validation, testing (VV&T), and employee training.

Echo Report

Further, the present disclosure describes an automated method for generating a comprehensive echocardiography report.

Further, the present disclosure describes a single product that produces a comprehensive echo report by combining deep learning models for echo, pathology detectors, and measurement estimators. This is not just putting several models together, but also having the outputs of black-box DNN models be combined with the clinical guidance to produce "white-box" understandable results. Further, creating such a comprehensive report is non-trivial due to the sheer number of pathologies possible. Therefore, a method is developed to train multiple models at scale simultaneously for generating the comprehensive report.

Figure 31:
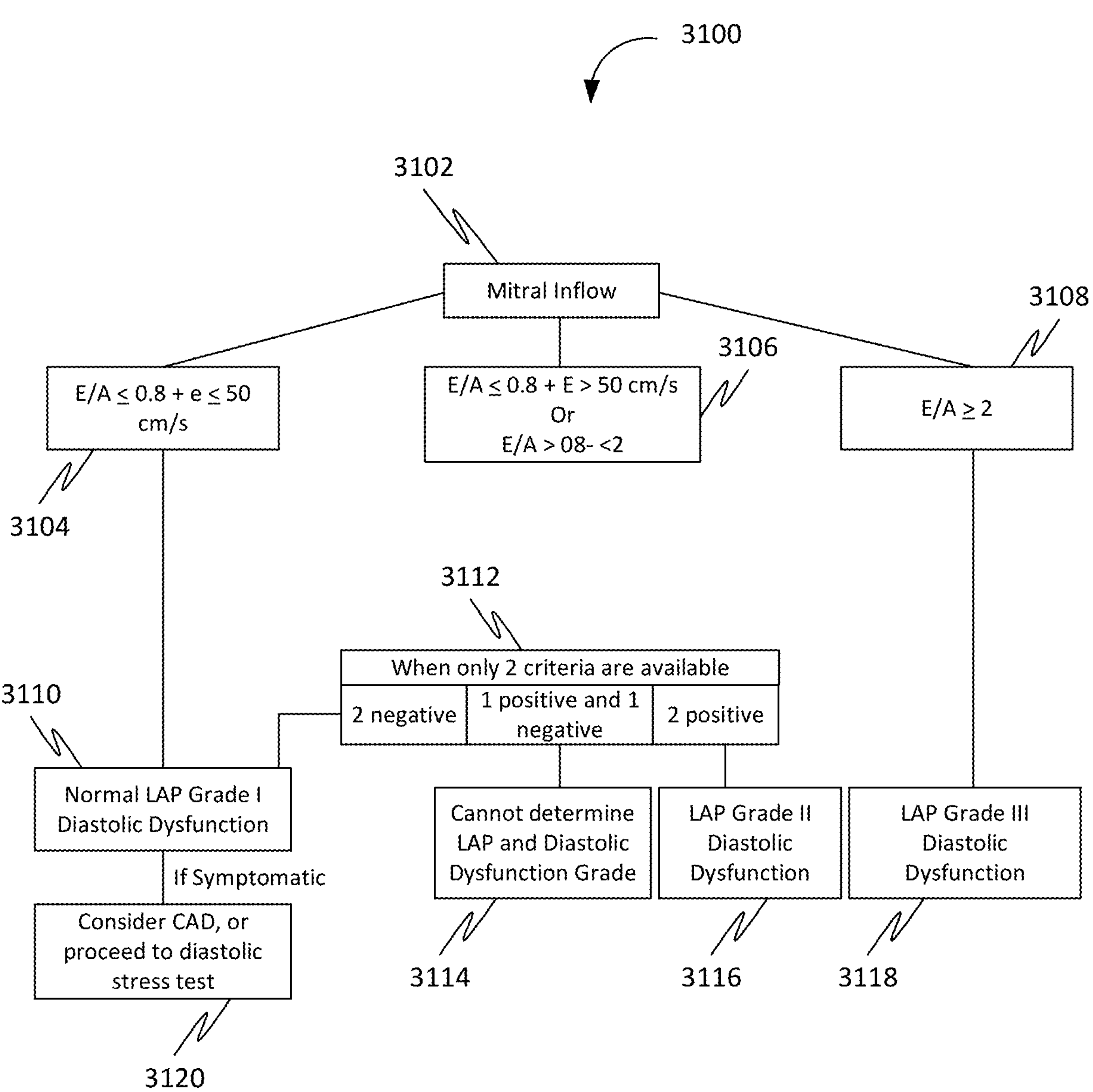
FIG. 31 is a flow chart of a diagnosis method 3100 for facilitating diagnosis based on medical imaging data, in accordance with some embodiments.

Further, the present disclosure describes a report workflow for generating a comprehensive echocardiography report. Further, the workflow includes a user submitting all ECHOs from an echocardiographic study and receiving a comprehensive echo report back complying with relevant certifying bodies (ie IAC guidances) and including all relevant clinical measurements (eg ejection fraction), pathologies (eg aortic stenosis), visualization of measurements (eg left ventricle overlay), and report conclusions. This will all be automatically generated. Further, a sample of the report is presented in FIG. 34-48. Further, the report workflow provides the full clinician report and combines multiple measurements and pathology predictions to provide more vetted and sanity-checked conclusions which according to clinical guidances require multiple measurements/findings as inputs. Further, the conclusions will combine measurements and diagnostics from the report with a rule based engine (based on current standard of care and ASE guidelines) to provide a complete conclusion. This is critical since with other products they only have a small subset of measurements and no diagnostics and thus cannot combine multiple predictions from within the report into the conclusion. For example, for diagnosis, a diagnosis flowchart (as shown in FIG. 31) is used, and the DNN estimated findings are directly plugged into the flowchart. The workflow for study processing is shown in FIG. 32. First every DICOM goes through a b-mode perspective classifier and then a view quality classifier.

B-Mode Doppler Readings

Further, the present disclosure describes the usage of B-Mode Pulmonary Pressure & Doppler Measurements. Further, items from b-mode images are estimated which typically require doppler readings. These include pulmonary pressure and e/e' ratio. Also conditions such as mitral regurgitation, tricuspid regurgitation, and aortic stenosis. This is done via a trained end-to-end neural network. Further, pulmonary pressure, e/e' ratio, and certain diagnoses on conditions (e.g. aortic stenosis, valve regurgitation) is obtained without relying on doppler readings or doppler measurements.

Further, the present disclosure describes a Dicom Quality Classifier. Further, the Dicom Quality Classifier is used to train a deep neural network (DNN) to directly estimate Dicom image quality. This is done by having trained clinicians label Dicom quality and then train the model to estimate their labels. This can also be expanded to other areas of quality including the type of imperfection in the image (eg off-axis, foreshortened, poor contrast/gain). Further, the Dicom Quality Classifier differs from a viewpoint quality classifier that does not directly measure image quality and often leads to poor quality DICOMs still defined as high quality.

Echo Training at Scale

Further, the present disclosure describes the usage of Echo training at Scale. Further, a platform is created that uses a database of clinician annotated echo reports and associated DICOMs to produce models for arbitrary conditions identified in the corpus of reports. This is accomplished in the following steps:

a. The user selects the condition they are going after (eg aortic stenosis) and the views where they believe the condition is present.
b. The software uses an NLP model to extract categories from freeform clinician notes which can be used to train ML algorithms. For example:

Original clinician notes: "Moderately enlarged with severe global hypokinesis. The estimated LV ejection fraction is 26%. Normal wall thickness." Output categories: ["Present—Any Hypokinesis", "Severe—Global Hypokinesis", "Moderate—Enlargement" ]

c. The software automatically identifies the relevant studies from a large database meeting the criteria for disease and views
d. The software spins up instances in the cloud to train the relevant models in parallel using predefined algorithms and architectures
e. The software automatically validates trained algorithms on a holdout set
f. The software automatically deploys to an internet endpoint accessible by API anywhere in the world, this step is optional.
g. A variation of the above where the user only selects the condition (eg aortic stenosis) and models are trained in every view in the database. The optimal model is then either directly selected by an end user or automatically via a preselected performance metric (eg. accuracy).

Further, the Echo training for multiple pathologies is not done in a bespoke manner where each model is trained independently. This eliminates impracticality when trying to make a comprehensive echo report since there are potentially hundreds of different conditions that may be present.

Retrospective Analysis

Further, the present disclosure describes a retrospective echo analysis. Further, for performing the retrospective echo analysis a system uses the full report workflow to analyze retrospective echo studies connected previously. This system will integrate with a hospital PACS/EMR system and filter studies from a specified date range. It will process those studies and produce a report for each of them. The end user will a priori select criteria to flag studies that produce certain results. For example, they may flag studies that the model indicates have moderate to severe aortic stenosis, but which have not been diagnosed as such in the EMR/PACS (ie a potentially missed diagnosis). These flagged studies will be presented to the end user in the form of an email warning or report. This system allows one to efficiently identify missed diagnoses in previously collected studies prior to engagement with the system.

Multi-Pathology Models and Generalized Echo Models

Current deep learning models used in echocardiography are trained to identify a single pathology (e.g. aortic stenosis), or set of measurements. However, a full comprehensive echocardiographic (echo) report contains multiple quantitative measurements and qualitative findings. Together, these parameters are considered in the diagnosis of pathologies. One approach to automatically generate the comprehensive echo report is to serially use separate models for each measurement and pathology. However, this is suboptimal because (1) this has high compute costs due to a large number of DNNs, which make processing inefficient (2) pathologies and other qualitative findings are not independent but rather highly correlated, for example, a patient exhibiting aortic stenosis is more likely to also display calcification of the aortic leaflets. Training and using in production separate models individually ignore these correlations, which are otherwise critical in forming a comprehensive echo report, and thus may lead to suboptimal results.

To address this, "generalized" echocardiography models are developed. The echocardiography models are trained on large echocardiography datasets using self-supervised learning techniques combined with multi-task learning. In the first stage, self-supervised learning is used to train a base network with an auxiliary task.

The choice of self-supervised learning (SSL) in this context is pivotal. Unlike traditional supervised learning, SSL does not require labeled data, which is a significant advantage in echocardiography where annotated datasets are often limited and expensive to produce. By leveraging SSL, the models learn to understand and represent echocardiographic data by finding patterns and structures within the data itself. This approach is particularly effective in capturing subtle, yet clinically significant features that might be overlooked in a fully supervised setting. For instance, SSL enables the model to recognize variations in cardiac structures that are indicative of early or mild pathologies, which are often underrepresented in labeled datasets. This leads to a more robust and generalizable model, capable of handling a wide range of echocardiographic presentations.

The auxiliary task may be to use an autoencoder to regenerate the input image from a lower-dimensional abstract space. It may also include a classification network that predicts whether two frames are from the same DICOM, or from the same patient. Regardless of the auxiliary task, the base network, as shown in FIG. 51, will produce an intermediate output that encodes the input to a lower dimensional abstract vector space. The input may be a single frame; two or more frames, each from a different DICOM; a cine-loop video composed of at least two frames; or multiple cine-loop videos of at least two frames, each video being from a different DICOM. This method ensures the model understands carry-over information that may be related to a condition present in the study, but relayed in separate frames or separate cine-loop DICOMs. In the second stage, a multi-output head is used to classify the lower dimensional abstract vector space representation of the inputs to multiple outputs. The outputs may be numbers indicating the probability the patient has a given pathology, indicators of the severity of that pathology (e.g., mild, moderate, or severe), or the probability that the two or more frames (or two or more videos) are from the same person or date. The outputs may also be clinically relevant metrics (e.g., pulmonary pressure).

In another embodiment of a multi-pathology model, a single classifier may be trained with a multi-output head in an end-to-end manner.

In the disclosed embodiment, the multi-output head is intricately engineered to process and interpret the lower-dimensional abstract vector space representations derived from echocardiographic inputs. This multi-output head is characterized by its unique modular architecture, comprising a plurality of distinct output layers, each specifically configured for dedicated analytical tasks pertinent to echocardiographic assessment.

Each output layer within the multi-output head is designed to execute a discrete function, encompassing, but not limited to, pathology classification, severity grading of identified pathologies, and quantitative echocardiographic measurements such as ventricular ejection fraction, chamber dimensions, and valvular function assessments. The configuration of these output layers is such that they operate in parallel, enabling simultaneous processing and analysis across multiple echocardiographic parameters.

A key feature of this multi-output head is its ability to integrate and cross-reference outputs from its various layers. This functionality is achieved through an inter-layer communication protocol, wherein the outputs of individual layers are shared and correlated, allowing for a comprehensive and integrated analysis. This protocol facilitates the synthesis of a holistic echocardiographic assessment, akin to the multifaceted analysis conducted in clinical practice.

Furthermore, the multi-output head is equipped with an advanced algorithmic framework that enables dynamic weighting of outputs based on their clinical relevance and interdependencies. This framework ensures that the final echocardiographic interpretation is not only a conglomeration of isolated findings but a coherent and clinically coherent analysis, enhancing the diagnostic utility of the model.

In summary, the multi-output head of the disclosed echocardiographic analysis model represents a significant advancement in the field, offering a sophisticated, integrated, and clinically nuanced approach to echocardiographic data interpretation.

To further refine and enhance the capabilities of the multi-pathology models and generalized echo models, an advanced process that intricately captures and interprets the qualitative nuances often found in physician textual notes, is developed. These notes, rich in clinical insights, are pivotal for a comprehensive understanding of echocardiographic studies.

This innovative process involves converting the textual data into a structured format that can be seamlessly integrated with the quantitative image analysis. By implementing an advanced encoder-decoder architecture, the system is adept at directly producing text tokens from the spatio-temporal features extracted from echocardiogram videos, as depicted in FIG. 52. This approach not only preserves the critical subtleties in the physician's interpretations but also bridges the gap between qualitative assessments and quantitative imaging data.

The extracted spatio-temporal features, obtained through sophisticated self-supervised learning techniques, are then fed into downstream applications designed for enhanced echocardiographic analysis. This encoder-decoder setup is versatile and can be employed in several groundbreaking applications related to echocardiography, including:

- Conversational Artificial Intelligence (AI): This application involves a dynamic system capable of discussing echocardiogram results in an interactive dialogue with healthcare providers or patients. The system first processes and computes a representation of the echo data. Utilizing an attention mechanism, it focuses on both the video representation and the historical text input from the user to generate contextually relevant responses, as illustrated in FIG. 53.
- Automated Clinical-Grade Reporting: The disclosed system can also transform the echocardiogram analysis into comprehensive clinical reports. This can be achieved through multiple methodologies:
  - Initially, the system utilizes the extracted features to calculate probabilities indicating the presence or absence of various pathologies. These probabilities are then input into a sophisticated text-generation API, which crafts detailed and accurate clinical reports.
  - Alternatively, the system is capable of predicting text tokens directly from the extracted features, streamlining the report generation process.

By integrating these advanced techniques, the system not only enhances the accuracy and efficiency of echocardiographic analysis but also significantly improves the interpretability and usability of the results for clinical decision-making.

Continuous Learning

A system, as shown in FIG. 54, takes in echocardiography data anonymizes it, and automatically produces clinically relevant measurements and findings to present to clinicians in the form of a GUI-based preliminary echo report. The clinicians can use the GUI to modify the reported elements (findings and measurements) in case they need corrections. Further, the GUI may be provided by a software application of iCardio.ai. Further, the GUI may be provided by a third party software application associated with a third party. Further, the third party software application may include picture archiving and communication systems (PACs) software applications, Electronic health record (EMR) software applications, etc. This corrected report is intended to be used in the upstream clinical workflow. The corrections are also sent to a cloud server where they are logged in a corrections database. Periodically, this logged correction data is used to fine-tune the relevant elements of the report-generating AI. This has the advantage of continuously improving the AI model results and increasing its accuracy.

Cross-Modality Training

Training an AI model to diagnose pathologies based on echocardiography images. However, the labels are derived from other imaging modalities including cardiac CT and MRI. These other imaging modalities may provide insights and accuracy which cannot be obtained from echocardiography. By training the echo AI models with outputs from these other modalities, the resultant AI models will learn features in the echocardiography input data which correlate with outcomes in other modalities. These features may or may not be known or detectable by human experts. These models may then provide information about the patient not typically detectable in echocardiography, or with higher accuracy than being typically obtained from echocardiography imagery alone.

In other embodiments, the other imaging modality may also be echocardiography, but in a different mode than used in a standard echo exam. This mode may include the use of contrast agents to improve echo image quality, as well as stress echo which puts the patient in a different physiological state than that seen in a standard (resting) echo exam.

Generic

Further, the present disclosure describes medical imaging systems and methods for facilitating diagnosis based on medical imaging data.

Further, the present disclosure relates generally to the field of image analysis. More specifically, the present disclosure relates to medical imaging systems and methods for facilitating diagnosis based on medical imaging data.

Further, the present disclosure relates generally to the field of data processing. More specifically, the present disclosure relates to methods and systems for facilitating feature engineering for machine learning models.

Further, the present disclosure describes AI-based Echo Interpretation. Further, the AI-based Echo Interpretation provides:

a. Increased Efficiency: Increases physician productivity and revenue by Increasing the speed of echo read.
b. Patient Identification: Identifies patient candidates for procedures and therapies (e.g. aortic valve replacement) which are otherwise missed.
c. Increased Quality: Automated case triage and a "second set of eyes" to improve patient outcomes and decrease hospital length of stay.
d. Echo Accessibility: Along with POCUS, opens the door for echo use in new markets such as post-acute care facilities and developing countries.

Further, the present disclosure describes an iCardio.ai Brain v1, which is a comprehensive AI system designed to mimic the thinking of a cardiologist. Further, the iCardio.ai Brain v1 is comprised of multiple neural networks. Further, the iCardio.ai Brain v1 can intake a free image and relay a comprehensive output. Further, the iCardio.ai Brain v1 automatically generates diameters, lengths, areas, and volumes of key features in the heart based on the image. Further, the iCardio.ai Brain v1 may ascertain ejection fraction and estimate pulmonary pressures even from limited views of the image. Further, the iCardio.ai Brain v1 reports a propensity score for the presence of multiple conditions, abnormalities, or diseases. Further, the iCardio.ai Brain v1 provides feedback on the resemblance of the image to the closest cardiac perspective. Further, the feedback includes instructions to adjust and correct the image. Further, the iCardio.ai Brain v1 provides feedback on view quality, assessing clarity, gain, zoom level, the inclusion of features, and usability of the image for downstream processing. Further, the iCardio.ai Brain v1 identifies the frames of key points within the cardiac cycle, i.e, end-diastole, mid-systole, etc.

Figures

FIG. 1 is an illustration of an online platform 100 consistent with various embodiments of the present disclosure. By way of non-limiting example, the online platform 100 to facilitate a diagnosis of pathologies using a machine learning model may be hosted on a centralized server 102, such as, for example, a cloud computing service. The centralized server 102 may communicate with other network entities, such as, for example, a mobile device 106 (such as a smartphone, a laptop, a tablet computer, etc.), other electronic devices 110 (such as desktop computers, server computers, etc.), databases 114, sensors 116, and a device 118 (such as a device 1000) over a communication network 104, such as, but not limited to, the Internet. Further, users of the online platform 100 may include relevant parties such as, but not limited to, end-users, administrators, service providers, service consumers, and so on. Accordingly, in some instances, electronic devices operated by the one or more relevant parties may be in communication with the platform.

A user 112, such as the one or more relevant parties, may access online platform 100 through a web based software application or browser. The web based software application may be embodied as, for example, but not be limited to, a website, a web application, a desktop application, and a mobile application compatible with a computing device 200.

Figure 2:
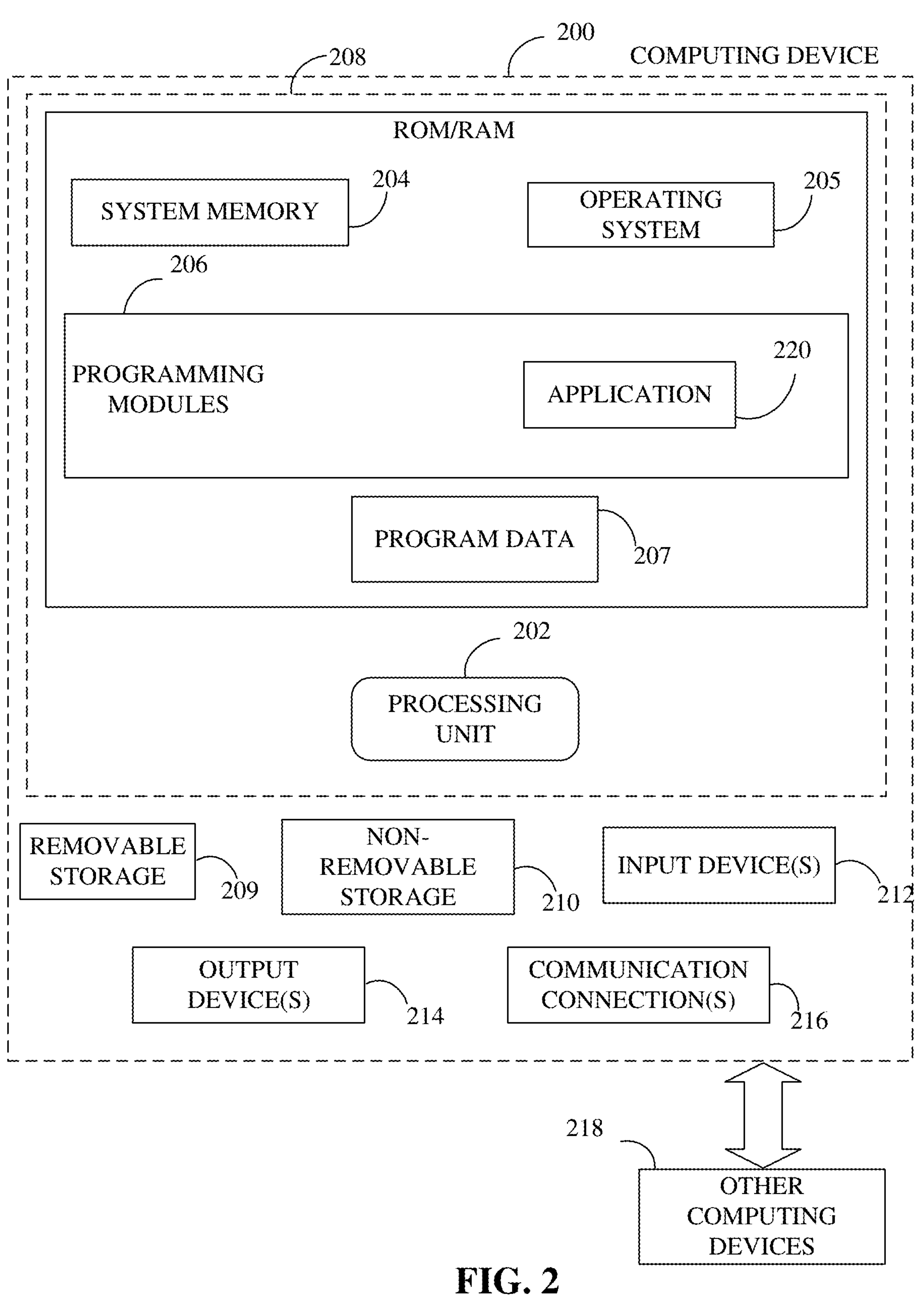
FIG. 2 is a block diagram of a computing device 200 for implementing the methods disclosed herein, in accordance with some embodiments.

With reference to FIG. 2, a system consistent with an embodiment of the disclosure may include a computing device or cloud service, such as computing device 200. In a basic configuration, computing device 200 may include at least one processing unit 202 and a system memory 204. Depending on the configuration and type of computing device, system memory 204 may comprise, but is not limited to, volatile (e.g. random-access memory (RAM)), non-volatile (e.g. read-only memory (ROM)), flash memory, or any combination. System memory 204 may include operating system 205, one or more programming modules 206, and may include a program data 207. Operating system 205, for example, may be suitable for controlling computing device 200's operation. In one embodiment, programming modules 206 may include an image-processing module and a machine learning module. Furthermore, embodiments of the disclosure may be practiced in conjunction with a graphics library, other operating systems, or any other application program and is not limited to any particular application or system. This basic configuration is illustrated in FIG. 2 by those components within a dashed line 208.

Computing device 200 may have additional features or functionality. For example, computing device 200 may also include additional data storage devices (removable and/or non-removable) such as, for example, magnetic disks, optical disks, or tape. Such additional storage is illustrated in FIG. 2 by a removable storage 209 and a non-removable storage 210. Computer storage media may include volatile and non-volatile, removable, and non-removable media implemented in any method or technology for storage of information, such as computer-readable instructions, data structures, program modules, or other data. System memory 204, removable storage 209, and non-removable storage 210 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 200. Any such computer storage media may be part of device 200. Computing device 200 may also have input device(s) 212 such as a keyboard, a mouse, a pen, a sound input device, a touch input device, a location sensor, a camera, a biometric sensor, etc. Output device(s) 214 such as a display, speakers, a printer, etc. may also be included. The aforementioned devices are examples and others may be used.

Computing device 200 may also contain a communication connection 216 that may allow device 200 to communicate with other computing devices 218, such as over a network in a distributed computing environment, for example, an intranet or the Internet. Communication connection 216 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 204, including operating system 205. While executing on processing unit 202, programming modules 206 (e.g., application 220 such as a media player) may perform processes including, for example, one or more stages of methods, algorithms, systems, applications, servers, and databases as described above. The aforementioned process is an example, and processing unit 202 may perform other processes. Other programming modules that may be used in accordance with embodiments of the present disclosure may include machine learning applications.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Figure 3:
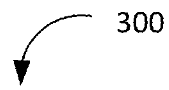
FIG. 3 is a flowchart of a method 300 for facilitating a diagnosis of pathologies using a machine learning model, in accordance with some embodiments.

FIG. 3 is a flowchart of a method 300 for facilitating a diagnosis of pathologies using a machine learning model, in accordance with some embodiments. Accordingly, the method 300 may include a step 302 of receiving, using a communication device, at least one medical data associated with at least one user from at least one device. Further, the at least one medical data may include a medical imaging data. Further, the medical imaging data may include transthoracic echocardiographic data. Further, the at least one medical data may include a Digital Imaging and Communications in Medicine (DICOM) data. Further, the DICOM data may include DICOM images, DICOM videos, etc. Further, the at least one medical data may include echocardiograms. Further, the at least one device may include a user device, a client device, a computing device, etc. Further, in an embodiment, the at least one medical data may include a single frame and/or two or more frames, each from a different DICOM, a cine-loop video composed of at least two frames or multiple cine-loop videos of at least two frames, each video being from a different DICOM.

Further, the method 300 may include a step 304 of analyzing, using a processing device, the at least one medical data using at least one machine learning model. Further, the at least one machine learning model may include at least one artificial neural network comprising a plurality of layers. Further, the plurality of layers may include at least one input layer, a plurality of output layers, and at least one middle layer between the at least one input layer and the plurality of output layers. Further, the at least one input layer may be configured for taking a plurality of medical data as a plurality of inputs to the at least one input layer. Further, the at least one middle layer may be configured for outputting a lower dimensional abstract vector space representation for each of the plurality of inputs by encoding the plurality of medical data to a lower dimensional abstract vector space. Further, the plurality of output layers may be configured for classifying the lower dimensional abstract vector space representation to a plurality of outputs corresponding to a plurality of assessment parameters considered in the diagnosis of the pathologies. Further, each of the plurality of output layers may be configured for communicating each of the plurality of outputs with at least one of the plurality of output layers. Further, each of the plurality of output layers may be configured for adjusting each of the plurality of outputs based on the at least one of the plurality of outputs of at least one of the plurality of output layers. Further, the analyzing of the at least one medical data may include inputting the at least one medical data to the at least one machine learning model. Further, the plurality of outputs may include may be numbers indicating probabilities of a pathology, indicators of a severity of the pathology (e.g., mild, moderate, or severe), probabilities of the two or more frames (or two or more videos) being from a same person or a same date, clinically relevant metrics (e.g., pulmonary pressure), etc. Further, the plurality of assessment parameters may include a pathology classification of the pathologies, a severity grading of the pathologies, one or more quantitative echocardiographic measurements, one or more echocardiographic parameters, etc. Further, the one or more quantitative echocardiographic measurements may include ventricular ejection fraction, chamber dimensions, valvular function assessments, etc. Further, the one or more echocardiographic parameters may include systolic function, diastolic function, left ventricular chamber remodeling, valvular lesions, systolic pulmonary arterial pressure, regional wall-motion abnormality, etc. Further, in an embodiment, the analyzing of the at least one medical data may include processing the at least one medical using a plurality of artificial intelligence (AI) pipelines. Further, the plurality of AI pipelines may include a general DICOM pipeline, a regression pipeline, a keypoint pipeline, and a segmentation pipeline. Further, in an embodiment, the at least one machine learning model may be a multi-pathology model. Further, the at least one artificial neural network may include a base network and a multi-output head. Further, the at least one input layer and the at least one middle layer may be comprised in the base network. Further, the plurality of output layers may be comprised in the multi-output head. Further, in an embodiment, the communicating of each of the plurality of outputs with at least one of the plurality of output layers may be based on an inter-layer communication protocol. Further, the communicating allows sharing and correlating of each of the plurality of outputs with at least one of the plurality of outputs for performing a comprehensive and integrated analysis. Further, in an embodiment, the at least one artificial neural network may be configured for extracting one or more spatiotemporal features from the at least one medical data. Further, the one or more spatiotemporal features correspond to cardiac features and cardia structures. Further, the at least one artificial neural network may be a Deep neural network (DNN), a Convolutional Neural Network (CNN), a "wide" 2-layer multi-level perceptron (MLP), etc. Further, the at least one machine learning model may have an Area Under the Receiver Operating Characteristic curve (AUROC) of 0.88 with 80% sensitivity and specificity, and an F1 score>0.85. Further, in an embodiment, the adjusting of each of the plurality of outputs based on at least one of the plurality of outputs of at least one of the plurality of output layers may be performed by applying a weight associated with at least one of the plurality of outputs to each of the plurality of outputs for adjusting each of the plurality of outputs. Further, in an embodiment, the adjusting of each of the plurality of outputs based on at least one of the plurality of outputs of at least one of the plurality of output layers may be performed by combining a weight associated with at least one of the plurality of outputs with a weight of each of the plurality of outputs for adjusting each of the plurality of outputs.

Further, the method 300 may include a step 306 of obtaining, using the processing device, one or more outputs corresponding to one or more assessment parameters from the at least one machine learning model for the diagnosis of one or more pathologies based on the analyzing of the at least one medical data. Further, the one or more outputs obtained from the at least one machine learning model have at least 80% sensitivity and specificity.

Further, the method 300 may include a step 308 of generating, using the processing device, at least one result based on the one or more outputs. Further, the generating of the at least one result may include formatting the one or more outputs to obtain one or more formatted outputs and processing the one or more formatted outputs using a multimodal language model or a text-text model. Further, in an embodiment, the one or more outputs may be one or more probabilities corresponding to the one or more assessment parameters (such as a presence of the one or more pathologies, a classification of the one or more pathologies, a severity grading of the one or more pathologies, one or more quantitative echocardiographic measurements of the one or more pathologies, etc.). Further, the generating of the at least one result may include inputting the one or more probabilities into a text generation Application Programming Interface (API). Further, the text generation API crafts detailed and accurate clinical reports. Further, the at least one result may include the detailed and accurate clinical reports.

Further, the method 300 may include a step 310 of storing, using a storage device, the at least one result and the at least one machine learning model.

Further, in some embodiments, the at least one device may include at least one medical imaging unit. Further, the at least one medical imaging unit may be configured for generating the at least one medical data associated with the at least one user by imaging at least one portion of at least one body part of the at least one user. Further, the at least one medical imaging unit may include one or more transducers. Further, the one or more transducers generate and transmit ultrasound waves to the at least one portion of the at least one body part and receive echos of the ultrasound waves from the at least one portion of the at least one body part for the generating of the at least one medical data. Further, the at least one device may include a hand held ultrasound devices, a hand held point-of-care ultrasound (POCUS) echocardiographic device, etc.

Further, in some embodiments, each of the plurality of output layers may be configured for executing a discrete function corresponding to each of the plurality of assessment parameters. Further, the classifying of the lower dimensional abstract vector space representation may be based on the executing. Further, the discrete function may corresponds to pathology classification, severity grading of identified pathologies, and quantitative echocardiographic measurements such as ventricular ejection fraction, chamber dimensions, and valvular function assessments.

Further, in some embodiments, each of the plurality of output layers may be configured for determining an interdependency of each of the plurality of outputs corresponding to each of the plurality of output layers with at least one of the plurality of outputs corresponding to at least one of the plurality of output layers. Further, the adjusting of each of the plurality of outputs may be based on the interdependency of each of the plurality of outputs corresponding to each of the plurality of output layers with at least one of the plurality of outputs corresponding to at least one of the plurality of output layers.

Further, in some embodiments, at least one artificial neural network may include a self-supervised learning neural network. Further, the self-supervised learning neural network may learn to understand and represent the at least one medical data by finding patterns and structures in the at least one medical data. Further, the self-supervised learning neural network may recognize variations in cardiac structures of a heart that are indicative of early or mild pathologies based on the learning. Further, the early or mild pathologies are underrepresented in a labeled dataset of medical images. Further, the self-supervised learning neural network offers an enhanced accuracy from the at least one medical data without requiring labeled training datasets.

Further, in some embodiments, the at least one artificial neural network may include at least one additional output layer. Further, the at least one additional output layer may be configured for predicting text tokens by decoding the lower dimensional abstract vector space representation. Further, the obtaining may include obtaining at least one text token corresponding to at least one additional assessment parameter for the diagnosis of the one or more pathologies. Further, the generating of the at least one result may be based on the at least one text token. Further, the at least one medical data may include a freeform text corresponding to a note from a clinician, a doctor, etc. Further, the at least one artificial neural network may include a text decoder. Further, the at least one additional output layer may be comprised in the text decoder. Further, the at least one additional assessment parameter may include a clinician's qualitative analysis of at least one echocardiogram comprised in the at least one medical data.

Further, in some embodiments, the at least one artificial neural network may be trained using a plurality of clinician annotated echo reports and associated DICOM data (such as DICOMs, DICOM images, DICOM videos, etc.).

Further, in some embodiments, the method 300 may include transmitting, using the communication device, the at least one result to the at least one device.

Further, in some embodiments, the at least one medical data may include at least one echocardiography data corresponding to at least one study. Further, the analyzing of the at least one medical data further may include analyzing the at least one echocardiography data using the at least one machine learning model. Further, the one or more outputs may include one or more predictions of a presence of one or more conditions, one or more estimations of one or more measurements, one or more visualizations of the one or more measurements, and one or more conclusions of the diagnosis. Further, the obtaining of the one or more outputs may include obtaining the one or more predictions of the presence of the one or more conditions, the one or more estimations of the one or more measurements, the one or more visualizations of the one or more measurements, and the one or more conclusions of the diagnosis from the at least one machine learning model. Further, the at least one result may include an echocardiography report. Further, the generating of the at least one result may include generating the echocardiography report by combining the one or more predictions of the presence of the one or more conditions, the one or more estimations of the one or more measurements, the one or more visualizations of the one or more measurements, and the one or more conclusions of the diagnosis. Further, the one or more measurements may include one or more of a linear measurement and a volumetric measurement from the trans-thoracic echocardiographic data. Further, the one or more of the linear measurement and the volumetric measurement may include a thickness of the Left Ventricular Inferolateral Wall (LVIWD), a thickness of the Interventricular Septum (LVISD), valve structure diameters of RV Outflow Tract, Right Ventricular Outflow Tract (RVOT), LV Outflow Tract, Left Ventricular Outflow Tract (LVOT), Aortic Valve, Aortic Annulus (AA), Sinus of Valsalva, Sinotubular Junction, and Proximal Ascending Aorta, other measurements such as Pulmonary Artery Pressure, etc. Further, the one or more conditions may include one or more of an aortic-stenosis, a left ventricle-atrial fibrillation, a mitral valve-bioprosthetic, a mitral valve annular calcification, an aortic valve calcification, a right atrium pacemaker, a mitral valve thickening, a myxomatous mitral valve, a left ventricle enlargement, a left ventricle hypokinesis, an aortic valve bioprosthetic, a right atrium enlargement, a right ventricle pacemaker, an aortic sclerosis, a left ventricle basal septal hypertrophy, an aortic root dilation, a left ventricle-hypertrophy, an aortic valve-thickening, a pericardial effusion, a left atrium-enlargement, a dilated ascending aorta, a right ventricle enlargement, a left ventricle diastolic dysfunction, an aortic valve bicuspid, and an aortic valve insufficiency.

Further, in some embodiments, the at least one medical data further may include at least one B mode image. Further, the analyzing of the at least one medical data further may include analyzing the at least one B mode image using the at least one machine learning model. Further, the at least one machine learning model may include a B mode perspective classifier and a view quality classifier. Further, the one or more outputs may include one or more estimations of one or more Doppler echocardiographic measurements and one or more predictions of one or more conditions. Further, the one or more Doppler echocardiographic measurements may include pulmonary pressure, e/e' ratio, etc. Further, the one or more conditions may include mitral regurgitation, tricuspid regurgitation, aortic stenosis, etc. Further, the obtaining of the one or more outputs may include obtaining the one or more estimations of the one or more Doppler echocardiographic measurements and the one or more predictions of the one or more conditions from the at least one machine learning model. Further, the generating of the at least one result may be further based on the one or more estimations of the one or more Doppler echocardiographic measurements and the one or more predictions of the one or more conditions. Further, the one or more Doppler echocardiographic measurements and the one or more predictions of the one or more conditions may be obtained without relying on doppler readings or doppler measurements.

FIG. 4 is a flowchart of a method 400 for facilitating a diagnosis of pathologies using a machine learning model, in accordance with some embodiments. Accordingly, the method 400 may include a step 402 of receiving, using the communication device, at least one additional medical data associated with the at least one user from the at least one device. Further, the at least one medical data may be associated with at least one modality and the at least one additional medical data may be associated with at least one additional modality. Further, the at least one modality may correspond to an echocardiography. Further, the at least one additional modality may correspond to a cardiac computed tomography (CT), a magnetic resonance imaging (MRI), etc. Further, the at least one medical data may include echocardiographs. Further, the at least one additional medical data may include CT scans, MRI scans, etc.

Further, the method 400 may include a step 404 of analyzing, using the processing device, the at least one additional medical data using the at least one machine learning model. Further, the at least one machine learning model may include at least one additional artificial neural network. Further, the at least one artificial neural network may be trained using a set of training medical data associated with the at least one modality and the at least one additional artificial neural network may be trained using a set of additional training medical data associated with the at least one additional modality. Further, the set of additional training medical data corresponds to the set of training medical data. Further, the at least one artificial neural network and the at least one additional artificial neural network may be jointly trained with a cross modality artificial neural network of the at least one machine learning model using a loss function created using outputs from the cross modality artificial neural network, the at least one artificial neural network, and the at least one additional artificial neural network. Further, the jointly training of the at least one artificial neural network and the at least one additional artificial neural network with the cross modality artificial neural network leverages at least one data fusion technique to enhance an accuracy of the at least one machine learning model by combining the at least one modality of the set of training medical data with the at least one additional modality of the set of training medical data. Further, the obtaining of the one or more outputs may be based on the analyzing of the at least one additional medical data. Further, the set of training medical data may include annotated echocardiographs and the set of additional training medical data may include annotated CT scans, annotated MRI scans, etc.

Further, in an embodiment, the cross modality artificial neural network includes a base network, and an auxiliary network for learning spatiotemporal features from the set of training medical data and the set of additional training medical data. Further, the set of training medical data and the set of additional training medical data may include DICOM images, DICOM videos, etc. Further, the at least one artificial neural network may include a base network, and a classification network for classifying the set of training medical data. Further, the at least one additional artificial neural network may include a base network, and an additional classification network for classifying the set of additional training medical data. Further, the at least one machine learning model may correlate the set of training medical data with the set of additional training medical data using the spatiotemporal features learned by the auxiliary network. Further, the at least one machine learning model may correlate one or more features present in the set of training medical data with one or more additional features present in the set of additional training medical data based on the spatiotemporal features learned by the auxiliary network of the cross modality artificial neural network.

Figure 5:
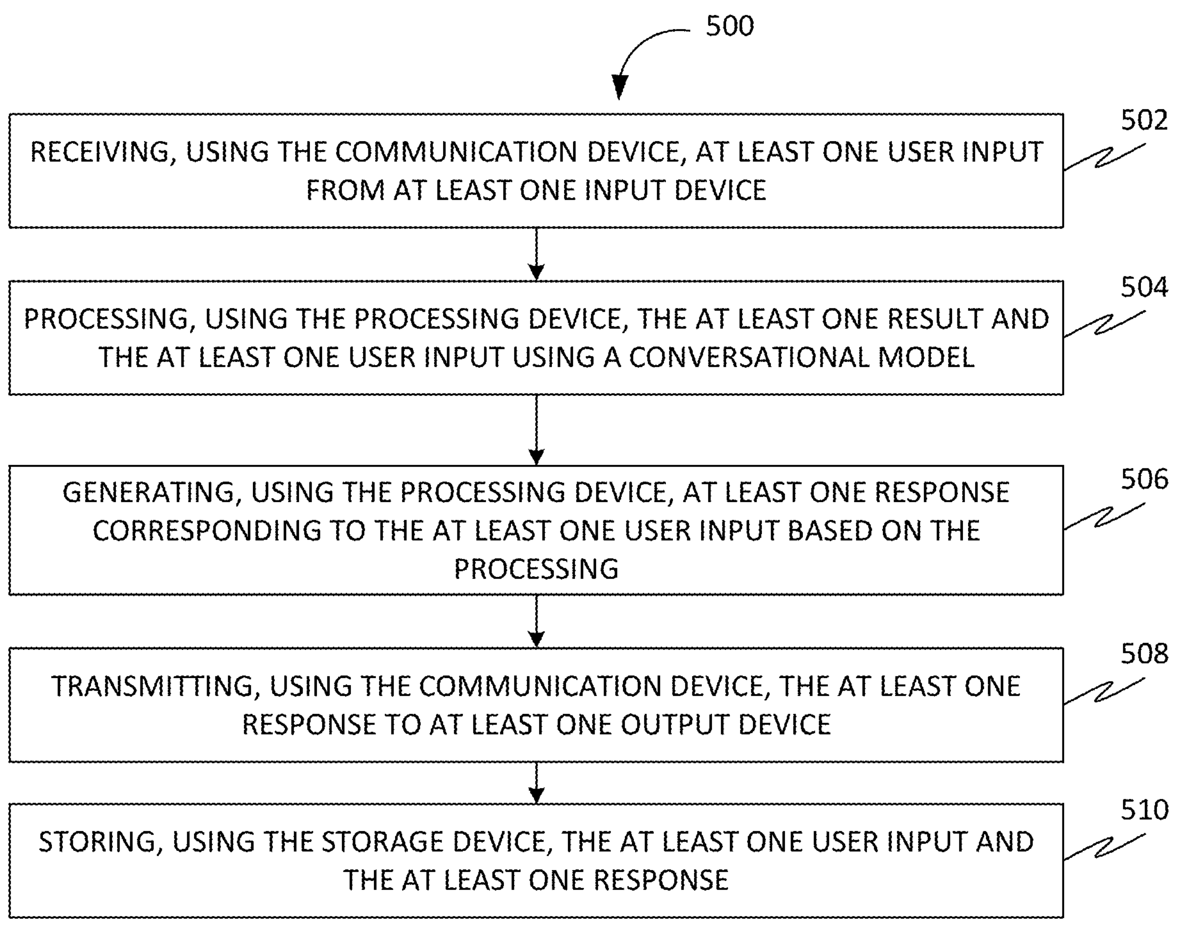
FIG. 5 is a flowchart of a method 500 for facilitating a diagnosis of pathologies using a machine learning model, in accordance with some embodiments.

FIG. 5 is a flowchart of a method 500 for facilitating a diagnosis of pathologies using a machine learning model, in accordance with some embodiments. Accordingly, the method 500 may include a step 502 of receiving, using the communication device, at least one user input from at least one input device. Further, the at least one user input may include a message, a query, a statement, etc. Further, the at least one user may include a doctor, a clinician, a patient, a healthcare provider, etc. Further, the at least one input device may include a user device, a client device, a computing device, etc.

Further, the method 500 may include a step 504 of processing, using the processing device, the at least one result and the at least one user input using a conversational model. Further, the conversational model may be an artificial intelligence model for facilitating a conversation. Further, the conversational model may include a natural language understanding (NLU) unit, a natural language generation (NLG) unit, and an attention mechanism implemented with the NLU unit and the NLG unit.

Further, the method 500 may include a step 506 of generating, using the processing device, at least one response corresponding to the at least one user input based on the processing.

Further, the method 500 may include a step 508 of transmitting, using the communication device, the at least one response to at least one output device. Further, the at least one output device may include a user device, a client device, a computing device, etc.

Further, the method 500 may include a step 510 of storing, using the storage device, the at least one user input and the at least one response.

FIG. 6 is a flowchart of a method 600 for facilitating a diagnosis of pathologies using a machine learning model, in accordance with some embodiments. Further, the conversational model may be configured for determining at least one context associated with the at least one user input.

Further, the method 600 may include a step 602 of retrieving, using the storage device, at least one of at least one historical medical data, at least one historical user input and at least one historical response based on the at least one context.

Further, the method 600 may include a step 604 of processing, using the processing device, at least one of the at least one historical medical data, the at least one historical user input, and the at least one historical response using the conversational model. Further, the generating of the at least one response may be based on the processing of the at least one historical user input.

Figure 7:
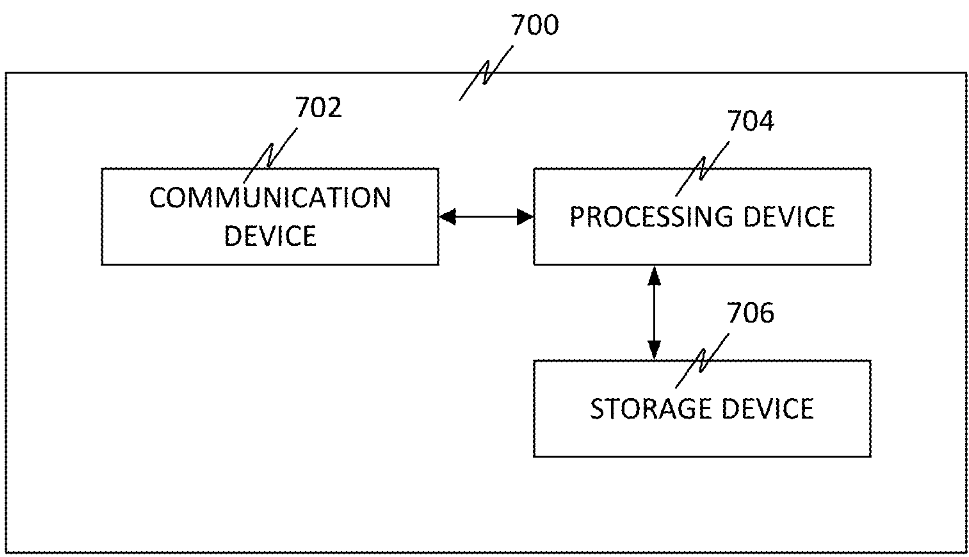
FIG. 7 is a block diagram of a system 700 for facilitating a diagnosis of pathologies using a machine learning model, in accordance with some embodiments.

FIG. 7 is a block diagram of a system 700 for facilitating a diagnosis of pathologies using a machine learning model, in accordance with some embodiments. Accordingly, the system 700 may include a communication device 702, a processing device 704, and a storage device 706.

Figure 8:
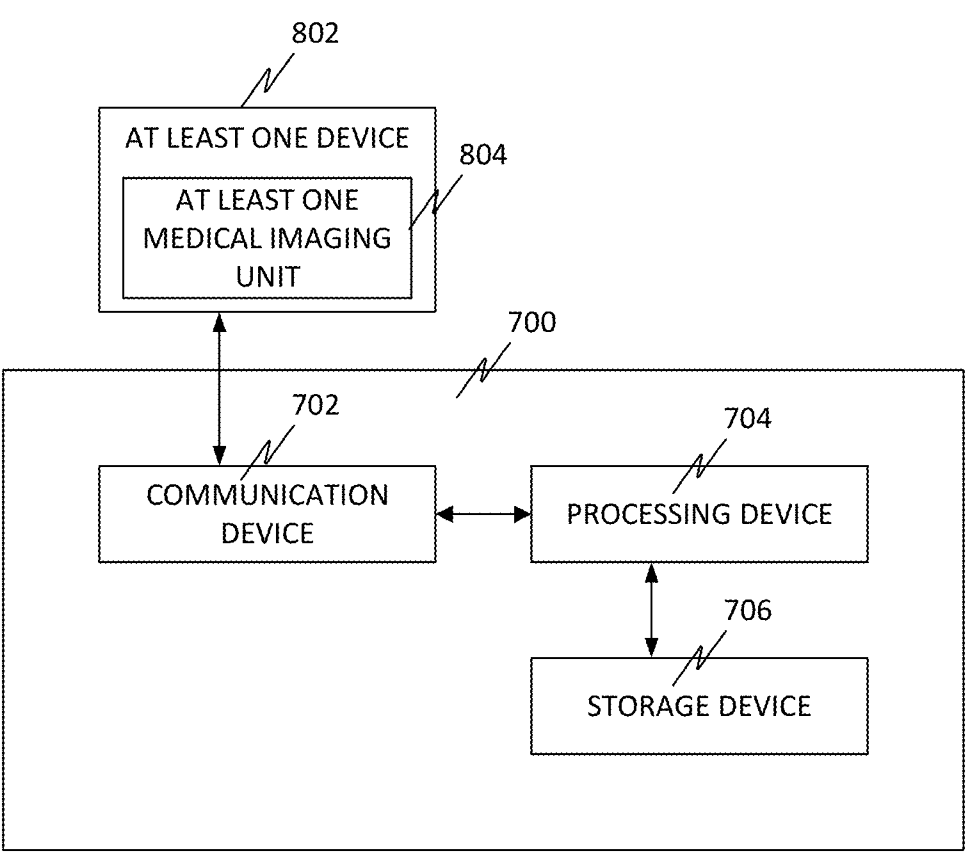
FIG. 8 is a block diagram of the system 700, in accordance with some embodiments.

Further, the communication device 702 may be configured for receiving at least one medical data associated with at least one user from at least one device 802, as shown in FIG. 8.

Further, the processing device 704 may be communicatively coupled with the communication device 702. Further, the processing device 704 may be configured for analyzing the at least one medical data using at least one machine learning model. Further, the at least one machine learning model may include at least one artificial neural network comprising a plurality of layers. Further, the plurality of layers may include at least one input layer, a plurality of output layers, and at least one middle layer between the at least one input layer and the plurality of output layers. Further, the at least one input layer may be configured for taking a plurality of medical data as a plurality of inputs to the at least one input layer. Further, the at least one middle layer may be configured for outputting a lower dimensional abstract vector space representation for each of the plurality of inputs by encoding the plurality of medical data to a lower dimensional abstract vector space. Further, the plurality of output layers may be configured for classifying the lower dimensional abstract vector space representation to a plurality of outputs corresponding to a plurality of assessment parameters considered in the diagnosis of the pathologies. Further, each of the plurality of output layers may be configured for communicating each of the plurality of outputs with at least one of the plurality of output layers. Further, each of the plurality of output layers may be configured for adjusting each of the plurality of outputs based on the at least one of the plurality of outputs of at least one of the plurality of output layers. Further, the analyzing of the at least one medical data may include inputting the at least one medical data to the at least one machine learning model. Further, the processing device 704 may be configured for obtaining one or more outputs corresponding to one or more assessment parameters from the at least one machine learning model for the diagnosis of one or more pathologies based on the analyzing of the at least one medical data. Further, the processing device 704 may be configured for generating at least one result based on the one or more outputs.

Further, the storage device 706 may be communicatively coupled with the processing device 704. Further, the storage device 706 may be configured for storing the at least one result and the at least one machine learning model.

Further, in some embodiments, the at least one device 802 may include at least one medical imaging unit 804, as shown in FIG. 8. Further, the at least one medical imaging unit 804 may be associated with at least one ultrasound imaging modality. Further, the at least one medical imaging unit 804 may be configured for generating the at least one medical data associated with the at least one user by imaging at least one portion of at least one body part of the at least one user. Further, the imaging may include ultrasound imaging of the at least one portion of the at least one body part of the at least one user.

Further, in some embodiments, each of the plurality of output layers may be configured for executing a discrete function corresponding to each of the plurality of assessment parameters. Further, the classifying of the lower dimensional abstract vector space representation may be further based on the executing.

Further, in some embodiments, each of the plurality of output layers may be configured for determining an interdependency of each of the plurality of outputs corresponding to each of the plurality of output layers with at least one of the plurality of outputs corresponding to at least one of the plurality of output layers. Further, the adjusting of each of the plurality of outputs may be further based on the interdependency of each of the plurality of outputs corresponding to each of the plurality of output layers with at least one of the plurality of outputs corresponding to at least one of the plurality of output layers.

Further, in some embodiments, at least one artificial neural network may include a self-supervised learning neural network. Further, the self-supervised learning neural network offers an enhanced accuracy from the at least one medical data without requiring labeled training datasets.

Further, in some embodiments, the at least one artificial neural network may include at least one additional output layer. Further, the at least one additional output layer may be configured for predicting text tokens by decoding the lower dimensional abstract vector space representation. Further, the obtaining further may include obtaining at least one text token corresponding to at least one additional assessment parameter for the diagnosis of the one or more pathologies. Further, the generating of the at least one result may be further based on the at least one text token.

Further, in some embodiments, the communication device 702 may be further configured for receiving at least one additional medical data associated with the at least one user from the at least one device 802. Further, the at least one medical data may be associated with at least one modality and the at least one additional medical data may be associated with at least one additional modality. Further, the processing device 704 may be further configured for analyzing the at least one additional medical data using the at least one machine learning model. Further, the at least one machine learning model further may include at least one additional artificial neural network. Further, the at least one artificial neural network may be trained using a set of training medical data associated with the at least one modality and the at least one additional artificial neural network may be trained using a set of additional training medical data associated with the at least one additional modality. Further, the set of additional training medical data corresponds to the set of training medical data. Further, the at least one artificial neural network and the at least one additional artificial neural network may be jointly trained with a cross modality artificial neural network of the at least one machine learning model using a loss function created using outputs from the cross modality artificial neural network, the at least one artificial neural network, and the at least one additional artificial neural network. Further, the jointly training of the at least one artificial neural network and the at least one additional artificial neural network with the cross modality artificial neural network leverages at least one data fusion technique to enhance an accuracy of the at least one machine learning model by combining the at least one modality of the set of training medical data with the at least one additional modality of the set of training medical data. Further, the obtaining of the one or more outputs may be further based on the analyzing of the at least one additional medical data.

Figure 9:
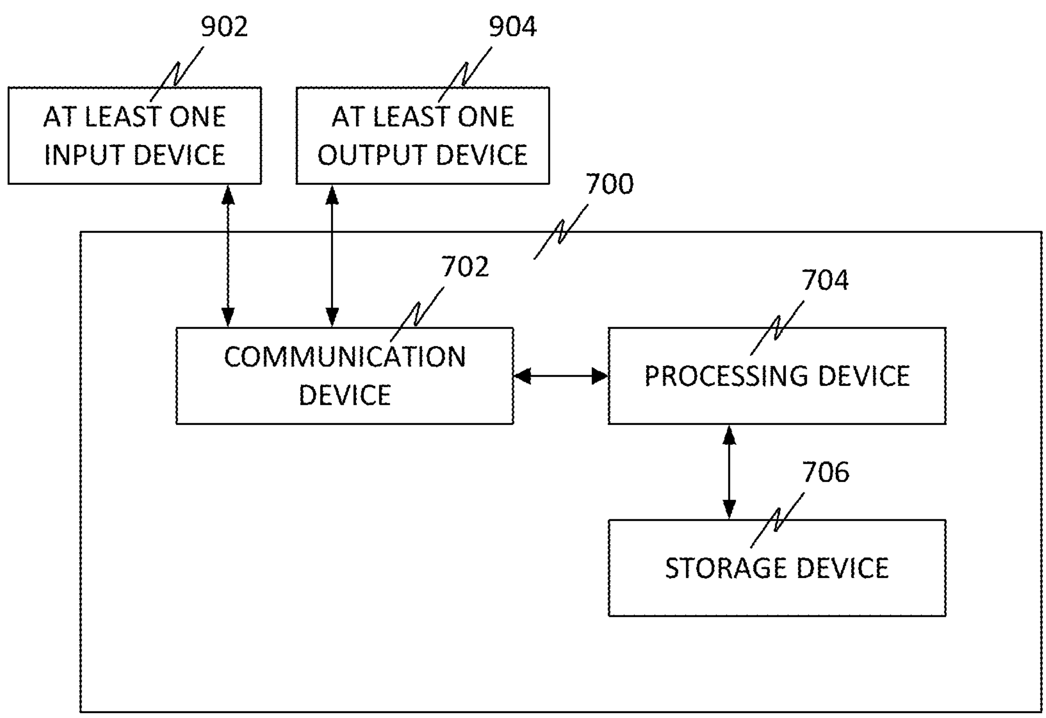
FIG. 9 is a block diagram of the system 700, in accordance with some embodiments.

Further, in some embodiments, the communication device 702 may be configured for receiving at least one user input from at least one input device 902, as shown in FIG. 9. Further, the communication device 702 may be configured for transmitting at least one response to at least one output device 904, as shown in FIG. 9. Further, the processing device 704 may be configured for processing the at least one result and the at least one user input using a conversational model. Further, the processing device 704 may be configured for generating the at least one response corresponding to the at least one user input based on the processing. Further, the storage device 706 may be further configured for storing the at least one user input and the at least one response.

Further, in an embodiment, the conversational model may be configured for determining at least one context associated with the at least one user input. Further, the storage device 706 may be further configured for retrieving at least one of at least one historical medical data, at least one historical user input and at least one historical response based on the at least one context. Further, the processing device 704 may be further configured for processing at least one of the at least one historical medical data, the at least one historical user input, and the at least one historical response using the conversational model. Further, the generating of the at least one response may be further based on the processing of the at least one historical user input.

Further, in some embodiments, the at least one medical data further may include at least one echocardiography data corresponding to at least one study. Further, the analyzing of the at least one medical data further may include analyzing the at least one echocardiography data using the at least one machine learning model. Further, the one or more outputs may include one or more predictions of a presence of one or more conditions, one or more estimations of one or more measurements, one or more visualizations of the one or more measurements, and one or more conclusions of the diagnosis. Further, the obtaining of the one or more outputs may include obtaining the one or more predictions of the presence of the one or more conditions, the one or more estimations of the one or more measurements, the one or more visualizations of the one or more measurements, and the one or more conclusions of the diagnosis from the at least one machine learning model. Further, the at least one result may include an echocardiography report. Further, the generating of the at least one result may include generating the echocardiography report by combining the one or more predictions of the presence of the one or more conditions, the one or more estimations of the one or more measurements, the one or more visualizations of the one or more measurements, and the one or more conclusions of the diagnosis.

Further, in some embodiments, the at least one medical data further may include at least one B mode image. Further, the analyzing of the at least one medical data further may include analyzing the at least one B mode image using the at least one machine learning model. Further, the one or more outputs may include one or more estimations of one or more Doppler echocardiographic measurements and one or more predictions of one or more conditions. Further, the obtaining of the one or more outputs may include obtaining the one or more estimations of the one or more Doppler echocardiographic measurements and the one or more predictions of the one or more conditions from the at least one machine learning model. Further, the generating of the at least one result may be further based on the one or more estimations of the one or more Doppler echocardiographic measurements and the one or more predictions of the one or more conditions.

Further, in some embodiments, the communication device 702 may be further configured for receiving at least one indication corresponding to at least one condition from the at least one device. Further, the processing device 704 may be further configured for identifying a plurality of clinician-annotated echocardiography reports and a plurality of echocardiography data associated with the plurality of clinician-annotated echocardiography reports from at least one data source based on the at least one indication. Further, the processing device 704 may be further configured for extracting at least one category from the plurality of clinician-annotated echocardiography reports using at least one natural language processing model. Further, the processing device 704 may be further configured for training one or more machine learning models using the at least one category and the plurality of echocardiography data. Further, the processing device 704 may be further configured for selecting the at least one machine learning model from the one or more machine learning models based on the at least one medical data. Further, the analyzing of the at least one medical data using the at least one machine learning model may be further based on the selecting.

Further, in some embodiments, the processing device 704 may be configured for identifying a plurality of historical studies from at least one data source based on a time criterion. Further, each of the plurality of historical studies may include at least one historical medical data and a historical result corresponding to the at least one historical medical data. Further, the processing device 704 may be configured for analyzing the plurality of studies using the at least one machine learning model. Further, the processing device 704 may be configured for generating a new result for each of the plurality of studies. Further, the processing device 704 may be configured for identifying at least one historical study from the plurality of historical studies based on at least one flagging criterion. Further, the new result of each of the at least one historical study disagrees with the historical result of each of the at least one historical study. Further, the processing device 704 may be configured for generating at least one warning based on the identifying of the at least one historical study. Further, the at least one warning indicates a misdiagnosis associated with the at least one historical study. Further, the communication device 702 may be further configured for receiving the at least one flagging criterion for flagging at least one of the plurality of studies from the at least one device. Further, the communication device 702 may be further configured for transmitting the at least one warning to the at least one device.

Further, in some embodiments, the communication device 702 may be configured for transmitting the at least one result to at least one clinician device associated with at least one clinician. Further, the communication device 702 may be configured for receiving at least one correction on the at least one result from the at least one clinician device. Further, the processing device 704 may be configured for updating the at least one result based on the at least one correction. Further, the processing device 704 may be configured for generating an updated result based on the updating. Further, the processing device 704 may be configured for retraining the at least one machine learning model based on the updated result. Further, the storage device 706 may be further configured for storing the updated result.

FIG. 8 is a block diagram of the system 700, in accordance with some embodiments.

FIG. 9 is a block diagram of the system 700, in accordance with some embodiments.

Figure 10:
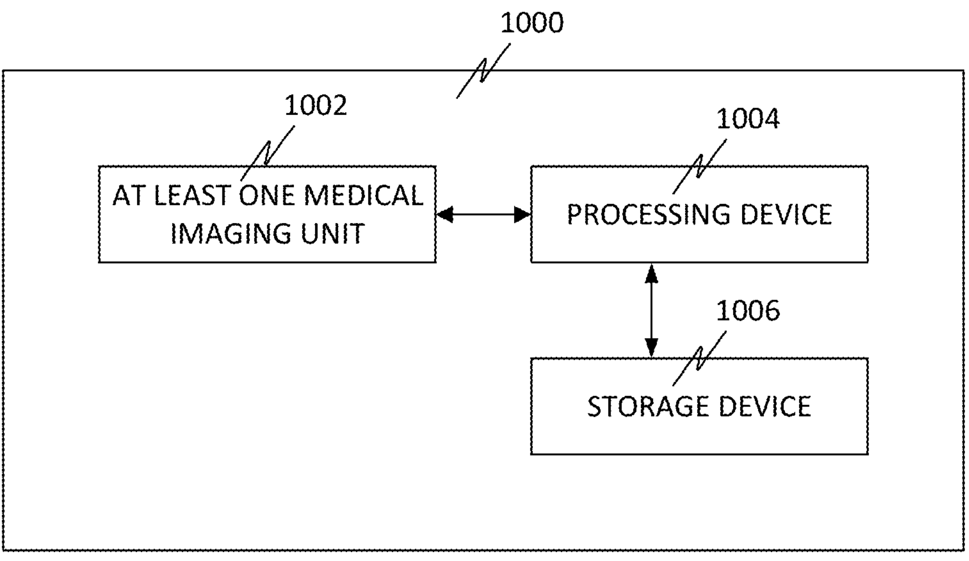
FIG. 10 is a block diagram of a device 1000 for facilitating a diagnosis of pathologies using a machine learning model, in accordance with some embodiments.

FIG. 10 is a block diagram of a device 1000 for facilitating a diagnosis of pathologies using a machine learning model, in accordance with some embodiments. Accordingly, the device 1000 may include at least one medical imaging unit 1002, a processing device 1004, and a storage device 1006.

Further, the at least one medical imaging unit 1002 may be configured for generating at least one medical data associated with at least one user by imaging at least one portion of at least one body part of the at least one user. Further, the at least one medical imaging unit 1002 may be associated with at least one ultrasound imaging modality. Further, the imaging may include ultrasound imaging of the at least one portion of the at least one body part of the at least one user.

Further, the processing device 1004 may be communicatively coupled with the at least one medical imaging unit 1002. Further, the processing device 1004 may be configured for analyzing the at least one medical data using at least one machine learning model. Further, the at least one machine learning model may include at least one artificial neural network comprising a plurality of layers. Further, the plurality of layers may include at least one input layer, a plurality of output layers, and at least one middle layer between the at least one input layer and the plurality of output layers. Further, the at least one input layer may be configured for taking a plurality of medical data as a plurality of inputs to the at least one input layer. Further, the at least one middle layer may be configured for outputting a lower dimensional abstract vector space representation for each of the plurality of inputs by encoding the plurality of medical data to a lower dimensional abstract vector space. Further, the plurality of output layers may be configured for classifying the lower dimensional abstract vector space representation to a plurality of outputs corresponding to a plurality of assessment parameters considered in the diagnosis of the pathologies. Further, each of the plurality of output layers may be configured for communicating each of the plurality of outputs with at least one of the plurality of output layers. Further, each of the plurality of output layers may be configured for adjusting each of the plurality of outputs based on the at least one of the plurality of outputs of at least one of the plurality of output layers. Further, the analyzing of the at least one medical data may include inputting the at least one medical data to the at least one machine learning model. Further, the processing device 1004 may be configured for obtaining one or more outputs corresponding to one or more assessment parameters from the at least one machine learning model for the diagnosis of one or more pathologies based on the analyzing of the at least one medical data. Further, the processing device 1004 may be configured for generating at least one result based on the one or more outputs.

Further, the storage device 1006 may be communicatively coupled with the processing device 1004. Further, the storage device 1006 may be configured for storing the at least one result and the at least one machine learning model.

Further, in some embodiments, each of the plurality of output layers may be configured for communicating each of the plurality of outputs with at least one of the plurality of output layers. Further, the adjusting of each of the plurality of outputs may be further based on at least one of the plurality of outputs of at least one of the plurality of output layers.

Further, in an embodiment, the device 1000 may include a hand held ultrasound devices, a hand held point-of-care ultrasound (POCUS) echocardiographic device, etc.

Figure 11:
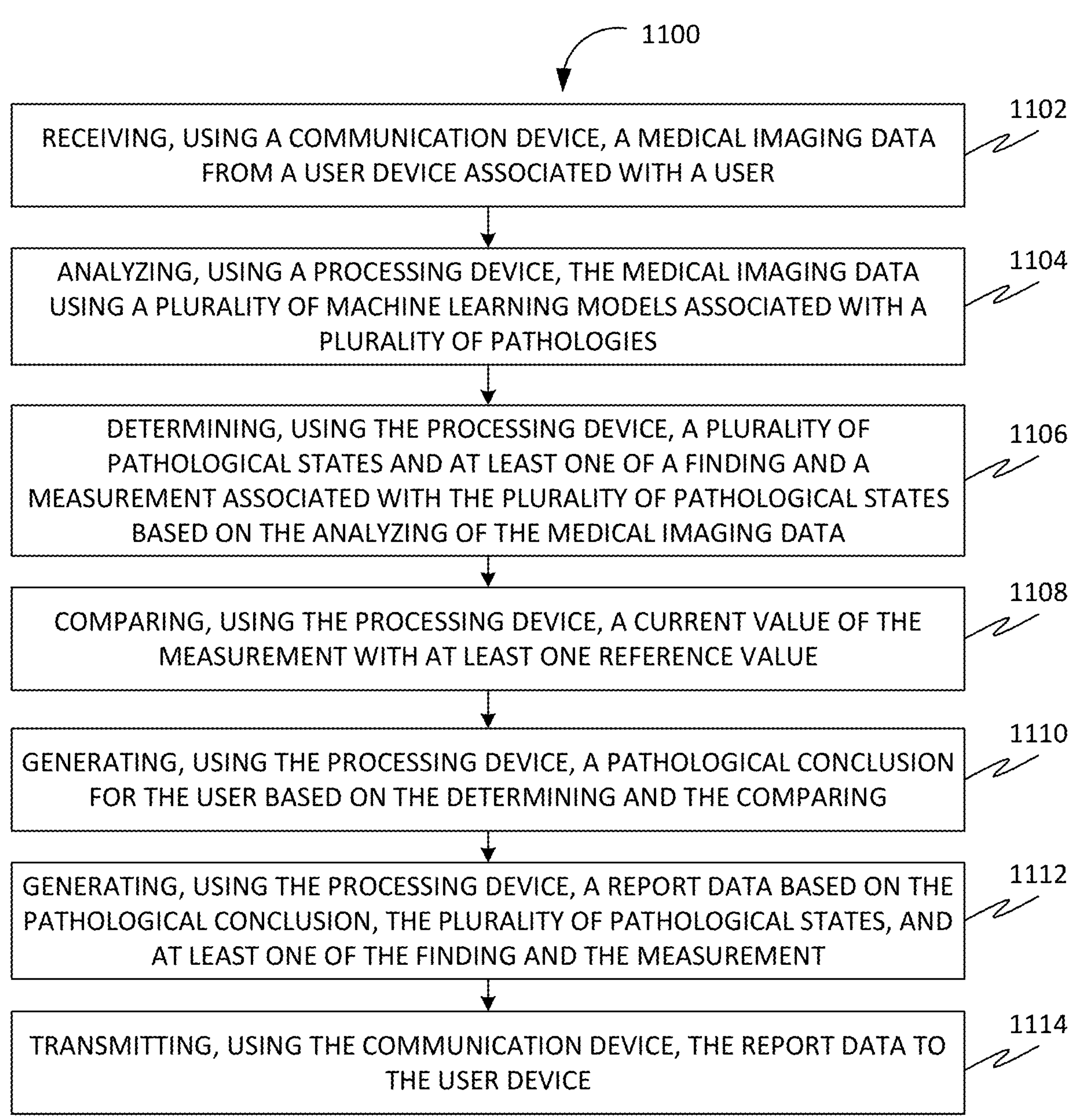
FIG. 11 is a flowchart of a method 1100 for facilitating diagnosis based on medical imaging data, in accordance with some embodiments.

FIG. 11 is a flowchart of a method 1100 for facilitating diagnosis based on medical imaging data, in accordance with some embodiments.

Accordingly, the method 1100 may include a step 1102 of receiving, using a communication device, a medical imaging data from a user device associated with a user. Further, the method 1100 may include a step 1104 of analyzing, using a processing device, the medical imaging data using two or more machine learning models associated with two or more pathologies. Further, the method 1100 may include a step 1106 of determining, using the processing device, two or more pathological states and at least one of a finding and a measurement associated with the two or more pathological states based on the analyzing of the medical imaging data. Further, the method 1100 may include a step 1108 of comparing, using the processing device, a current value of the measurement with one or more reference values. Further, the measurement may be determined to either be normal or pathological based on the comparing. Further, the method 1100 may include a step 1110 of generating, using the processing device, a pathological conclusion for the user based on the determining and the comparing. Further, the method 1100 may include a step 1112 of generating, using the processing device, a report data based on the pathological conclusion, the two or more pathological states, and at least one of the finding and the measurement. Further, the method 1100 may include a step 1114 of transmitting, using the communication device, the report data to the user device.

In some embodiments, the two or more pathological states include two or more cardiac anomalies.

In some embodiments, the two or more cardiac anomalies include Hypertrophic cardiomyopathy (HCM).

In some embodiments, the two or more machine learning models may be trained on a dataset comprising a number of medical imaging data.

In some embodiments, the medical imaging data includes trans-thoracic echocardiographic data.

In some embodiments, the method 1100 may be performed by a medical imaging device.

In some embodiments, the medical imaging device includes a handheld ultrasound device.

In some embodiments, a pathological state includes a severity level of a symptom.

In some embodiments, the severity level includes one of none, mild, moderate, and severe.

In some embodiments, the HCM includes one of symptomatic HCM and asymptomatic HCM.

In some embodiments, the trans-thoracic echocardiographic data includes B-mode images.

In some embodiments, the trans-thoracic echocardiographic may be anonymized using an anonymization algorithm for removing protected health information from the trans-thoracic echocardiographic data. Further, the trans-thoracic echocardiographic data may be classified using a view classifier for identifying a view of the trans-thoracic echocardiographic data.

In some embodiments, the trans-thoracic echocardiographic data may be characterized as one of training data and validation data. Further, the training data may be used for training the two or more machine learning models.

In some embodiments, at least one of the two or more machine learning models includes a video-level end to end HCM model. Further, the video-level end to end HCM model may be configured for facilitating the diagnosis of the HCM and scoring a severity of the HCM (disease).

In some embodiments, one or more of the two or more machine learning models includes a measurement model. Further, the measurement model may be configured for facilitating an anatomical and physiological measurement.

In some embodiments, the two or more machine learning models include at least thirty machine learning models.

In some embodiments, the medical imaging data includes a video. Further, the analyzing of the video may be performed using the two or more machine learning models.

In some embodiments, the medical imaging device includes an echocardiographic device.

In some embodiments, each of the two or more machine learning models may be based on at least sixty artificial intelligence algorithms for determining an anatomical measurement, a physiological measurement, and a pathology.

In some embodiments, the anatomical measurement includes a left ventricular volume. Further, the physiological measurement includes an ejection fraction and the pathology includes an aortic stenosis.

In some embodiments, the medical imaging data includes a Digital Imaging and Communications in Medicine (DICOM) video.

In some embodiments, the dataset may be categorized into a training set and a testing set. Further, the training set includes a first part of the dataset which may facilitate training of the two or more machine learning models. Further, the testing set includes a second part of the dataset which may facilitate validation of the two or more machine learning models.

In some embodiments, the trans-thoracic echocardiographic data includes a B-mode image for a curation of the dataset.

In some embodiments, the medical imaging data includes annotation data. Further, the severity level may be based on the annotation data.

Figure 50:
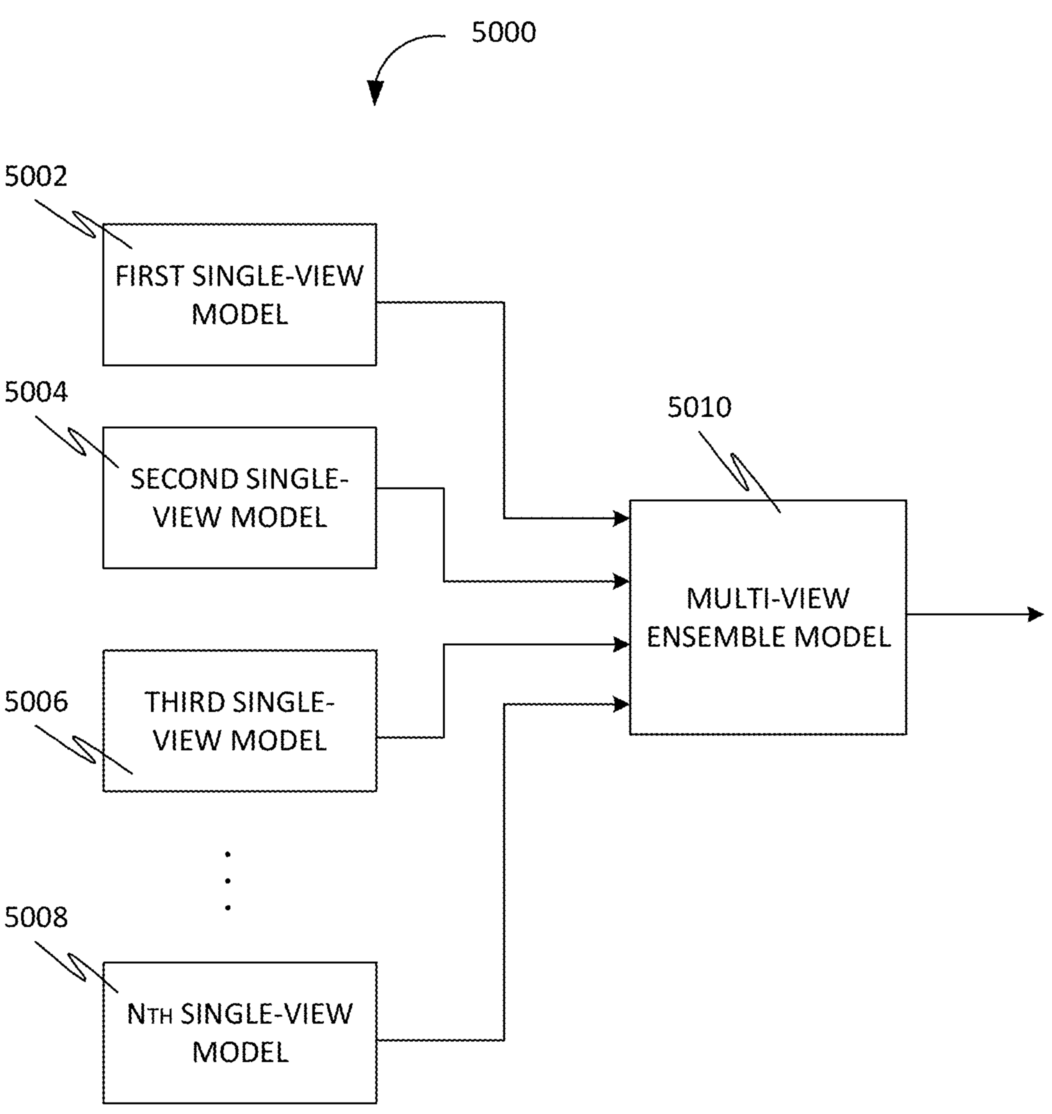
FIG. 50 illustrates a machine learning model 5000 for facilitating diagnosis based on medical imaging data, in accordance with some embodiments.

In some embodiments, the two or more machine learning models include a multi-view ensemble model. For example, as shown in FIG. 50, the multi-view ensemble model may take outputs from a plurality of single-view models for specific pathologies (e.g. an A4C and PLAX model for aortic stenosis) and combine the outputs of the plurality of single-view models with a distinct ensemble model to produce a single pathology propensity score. Further, the multi-view ensemble model use machine learning to optimally weigh the outputs of each of the plurality of single-view models to generate a final output. In some embodiments, the multi-view ensemble model may be trained independently from the plurality of single-view models. Further, in some other embodiments, the multi-view ensemble model may be trained jointly with the plurality of single-view models. Further, the plurality of single-view models may include b-mode views (e.g. A4C), M-Mode views, Doppler views, and other echocardiographic views obtained in standard echo exams.

Further, the multi-view ensemble model may be configured for facilitating diagnosis of a pathology, scoring of a severity of a disease, and an anatomical and physiological measurement.

In some embodiments, the method may include a step of receiving, using the communication device, clinical data from at least one clinician device associated with at least one clinician. Further, the at least one clinician device may execute at least one software application. Further, the at least one software application provides a graphical user interface for inputting the clinical data. Further, the clinical data may be based on a natural language. Further, the clinical data may include a diagnosis, a correction in at least one measurement, etc. from the at least one clinician. Further, the diagnosis, the correction, etc. may be in the natural language. Further, the natural language may include English language, Spanish Language, French language, etc. Further, the method may include a step of analyzing, using the processing device, the clinical data using at least one natural language processing (NLP) model. Further, the identifying of the two or more pathological states may be based on the analyzing of the clinical data.

In some embodiments, the method 1100 may further include retrieving, using a storage device, a clinical report data. Further, the identifying of the two or more pathological states may be based on the clinical report data.

In some embodiments, the medical imaging data includes a Doppler measurement.

In some embodiments, the medical imaging data further includes a previous report data. Further, the generating of the report data may be further based on the previous report data.

In some embodiments, the two or more cardiac anomalies include one or more of an aortic-stenosis, a left ventricle-atrial fibrillation, a mitral valve-bioprosthetic, a mitral valve annular calcification, an aortic valve calcification, a right atrium pacemaker, a mitral valve thickening, a myxomatous mitral valve, a left ventricle enlargement, a left ventricle hypokinesis, an aortic valve bioprosthetic, a right atrium enlargement, a right ventricle pacemaker, an aortic sclerosis, a left ventricle basal septal hypertrophy, an aortic root dilation, a left ventricle-hypertrophy, an aortic valve-thickening, a pericardial effusion, a left atrium-enlargement, a dilated ascending aorta, a right ventricle enlargement, a left ventricle diastolic dysfunction, an aortic valve bicuspid, and an aortic valve insufficiency.

Figure 12:
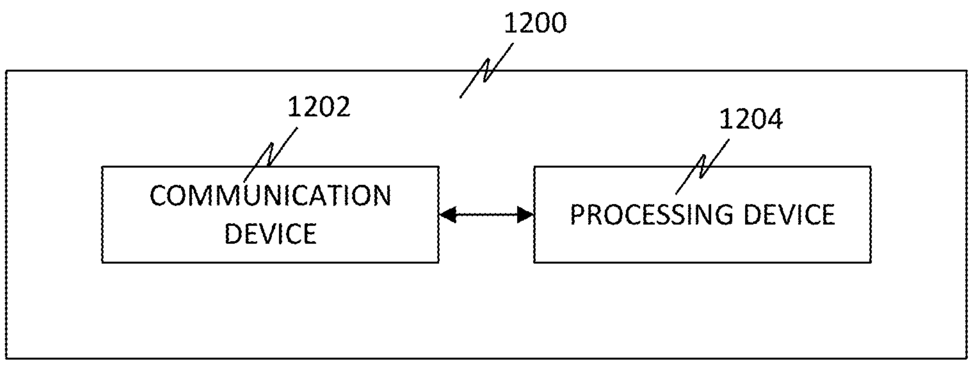
FIG. 12 is a block diagram of a system 1200 for facilitating diagnosis based on medical imaging data, in accordance with some embodiments.

FIG. 12 is a block diagram of a system 1200 for facilitating diagnosis based on medical imaging data, in accordance with some embodiments.

Accordingly, the system 1200 may include a communication device 1202. Further, the communication device 1202 may be configured for receiving medical imaging data from a user device associated with a user. Further, the communication device 1202 may be configured for transmitting report data to the user device. Further, the medical imaging system 1200 may include a processing device 1204. Further, the processing device 1204 may be configured for analyzing the medical imaging data using two or more machine learning models associated with two or more pathologies. Further, the processing device 1204 may be configured for determining two or more pathological states and at least one of a finding and a measurement associated with the two or more pathological states based on the analyzing of the medical imaging data. Further, the processing device 1204 may be configured for comparing a current value of the measurement with one or more reference values. Further, the processing device 1204 may be configured for generating a pathological conclusion for the user based on the determining and the comparing. Further, the processing device 1204 may be configured for generating the report data based on the pathological conclusion, the two or more pathological states, and at least one of the finding and the measurement.

In some embodiments, the two or more pathological states include two or more cardiac anomalies.

In some embodiments, the two or more cardiac anomalies include Hypertrophic cardiomyopathy (HCM).

In some embodiments, the two or more machine learning models may be trained on a dataset comprising a number of medical imaging data.

In some embodiments, the medical imaging data includes a trans-thoracic echocardiographic data.

In some embodiments, the user device may include a medical imaging device.

Further, the medical imaging device may be configured for generating the medical imaging data.

In some embodiments, the medical imaging device includes a handheld ultrasound device.

In some embodiments, at least one of the two or more pathological states includes a severity level of a symptom.

In some embodiments, the severity level includes one of none, mild, moderate, and severe.

In some embodiments, the HCM includes one of symptomatic HCM and asymptomatic HCM.

In some embodiments, the trans-thoracic echocardiographic data includes B-mode images.

In some embodiments, the trans-thoracic echocardiographic data may be anonymized using an anonymization algorithm for removing a protected health information from the trans-thoracic echocardiographic data. Further, the trans-thoracic echocardiographic data may be classified using a view classifier for identifying a view of the trans-thoracic echocardiographic data.

In some embodiments, the trans-thoracic echocardiographic data may be characterized as one of a training data and a validation data. Further, the training data may be used for training the two or more machine learning models.

In some embodiments, at least one of the two or more machine learning models includes a video-level end to end HCM model. Further, the video-level end to end HCM model may be configured for facilitating the diagnosis of the HCM and scoring a severity of the HCM (disease).

In some embodiments, one or more of the two or more machine learning models includes a measurement model. Further, the measurement model may be configured for facilitating an anatomical and physiological measurement.

In some embodiments, the two or more machine learning models include at least thirty machine learning models.

In some embodiments, the medical imaging data includes a video. Further, the analyzing of the video may be performed using the two or more machine learning models.

In some embodiments, the medical imaging device includes an echocardiographic device.

In some embodiments, each of the two or more machine learning models may be based on at least sixty artificial intelligence algorithms for determining an anatomical measurement, a physiological measurement, and a pathology.

In some embodiments, the anatomical measurement includes a left ventricular volume. Further, the physiological measurement includes an ejection fraction and pathology includes an Aortic Stenosis.

In some embodiments, the medical imaging data includes a Digital Imaging and Communications in Medicine (DICOM) video.

In some embodiments, the dataset may be categorized into a training set and a testing set. Further, the training set includes a first part of the dataset which may facilitate training of the two or more machine learning models. Further, the testing set includes a second part of the dataset which may facilitate validation of the two or more machine learning models.

In some embodiments, the trans-thoracic echocardiographic data includes a B-mode image for a curation of the dataset.

In some embodiments, the medical imaging data includes an annotation data. Further, the severity level may be based on the annotation data.

In some embodiments, the two or more machine learning models include a multi-view ensemble model. Further, the multi-view ensemble model may be configured for facilitating the diagnosis of the HCM, scoring of a severity of a disease, and an anatomical and physiological measurement.

In some embodiments, the medical imaging data includes a clinical data. Further, the clinical data may be based on a natural language.

In some embodiments, the system 1200 may further include a storage device. Further, the storage device may be configured for retrieving a clinical report data. Further, the identifying of the two or more pathological states may be based on the clinical report data.

In some embodiments, the medical imaging data includes a Doppler measurement.

In some embodiments, the medical imaging data further includes a previous report data. Further, the generating of the report data may be further based on the previous report data.

In some embodiments, the two or more cardiac anomalies include one or more of an aortic-stenosis, a left ventricle-atrial fibrillation, a mitral valve-bioprosthetic, a mitral valve annular calcification, an aortic valve calcification, a right atrium pacemaker, a mitral valve thickening, a myxomatous mitral valve, a left ventricle enlargement, a left ventricle hypokinesis, an aortic valve bioprosthetic, a right atrium enlargement, a right ventricle pacemaker, an aortic sclerosis, a left ventricle basal septal hypertrophy, an aortic root dilation, a left ventricle-hypertrophy, an aortic valve-thickening, a pericardial effusion, a left atrium-enlargement, a dilated ascending aorta, a right ventricle enlargement, a left ventricle diastolic dysfunction, an aortic valve bicuspid, and an aortic valve insufficiency.

Figure 13:
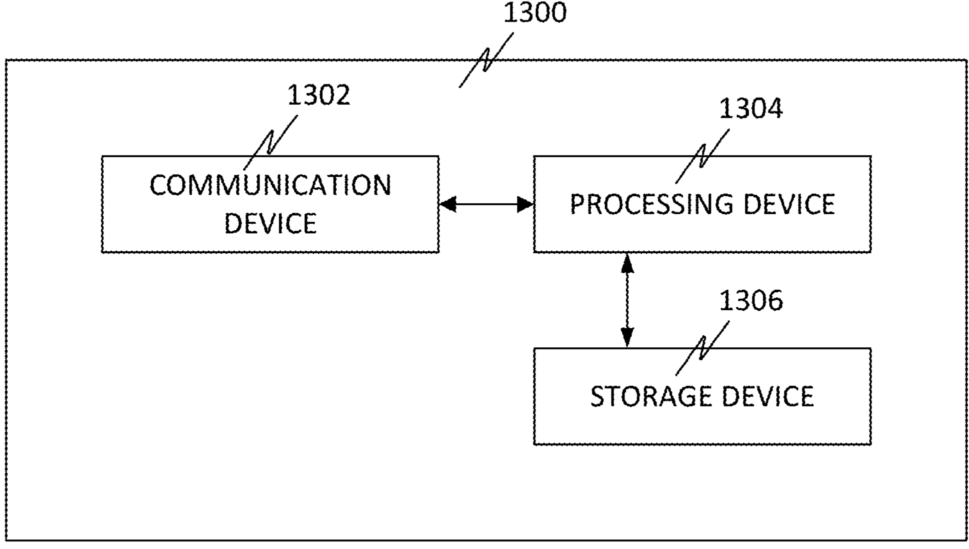
FIG. 13 is a block diagram of a medical imaging device 1300 for facilitating diagnosis based on medical imaging data, in accordance with some embodiments.

FIG. 13 is a block diagram of a medical imaging device 1300 for facilitating diagnosis based on medical imaging data, in accordance with some embodiments. Further, the medical imaging device 1300 may be configured for generating a medical imaging data.

Further, the medical imaging device 1300 may include a processing device 1304. Further, the processing device 1304 may be configured for analyzing the medical imaging data using two or more machine learning models corresponding to two or more pathologies. Further, the processing device 1304 may be configured for identifying two or more pathological states based on the analyzing of the medical imaging data. Further, the processing device 1304 may be configured for generating a report data based on the identifying. Further, the medical imaging device 1300 may include a storage device 1306 communicatively coupled with the processing device 1304. Further, the storage device 1306 may be configured for storing the report data in a database. Further, the medical imaging device 1300 may include a communication device 1302 communicatively coupled with the processing device 1304. Further, the communication device 1302 may be configured for transmitting the report data to a user device.

Figure 14:
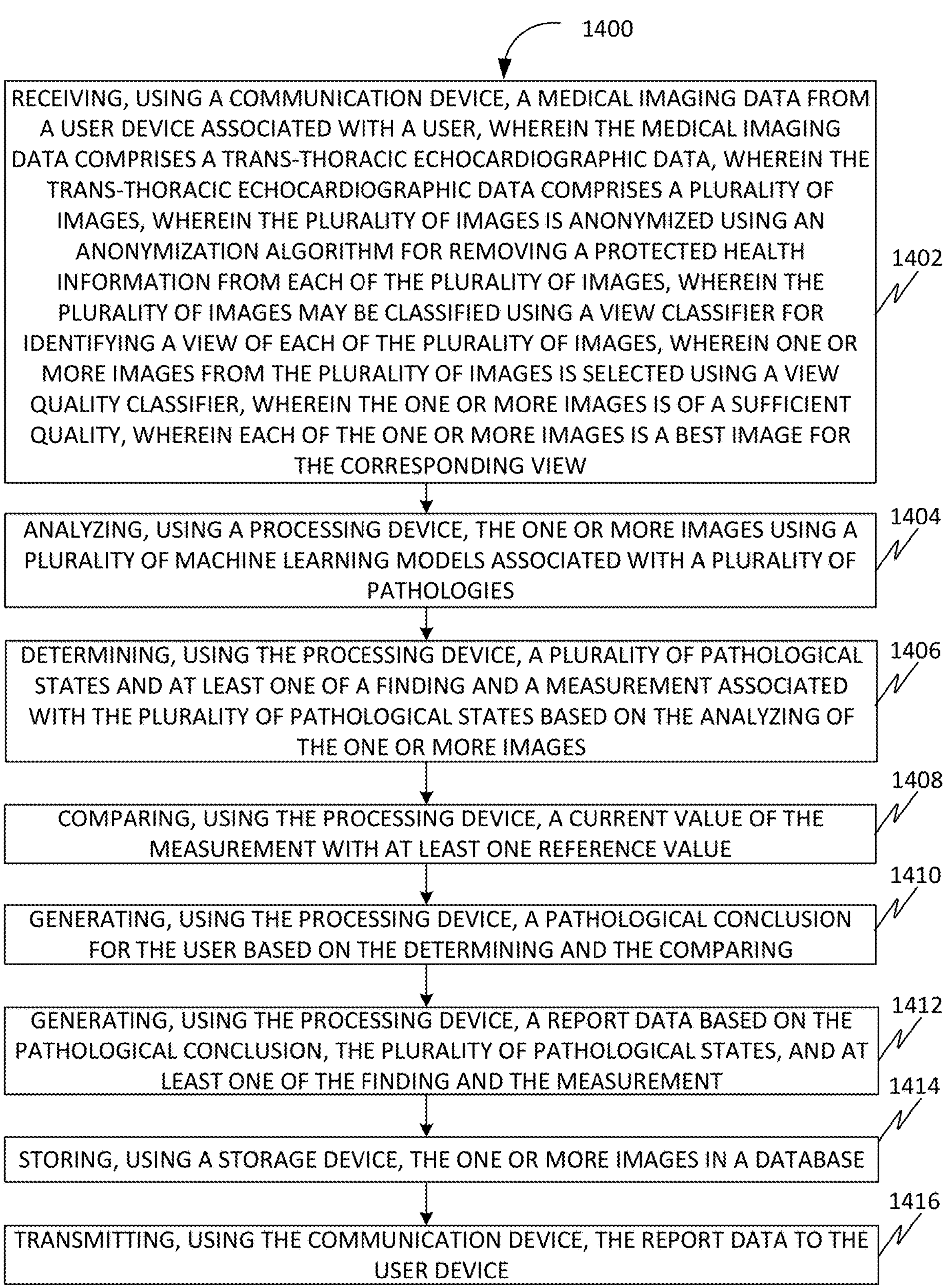
FIG. 14 is a flowchart of a method 1400 for facilitating diagnosis based on medical imaging data, in accordance with some embodiments.

FIG. 14 is a flowchart of a method 1400 for facilitating diagnosis based on medical imaging data, in accordance with some embodiments.

Accordingly, the method 1400 may include a step 1402 of receiving, using a communication device, a medical imaging data from a user device associated with a user. Further, the medical imaging data may include a trans-thoracic echocardiographic data. Further, the trans-thoracic echocardiographic data may include two or more images. Further, the two or more images may be anonymized using an anonymization algorithm for removing a protected health information from each of the two or more images. Further, the two or more images may be classified using a view classifier for identifying a view of each of the two or more images. Further, one or more images from the two or more images may be selected using a view quality classifier. Further, the one or more images may be of a sufficient quality. Further, each of the one or more images may be a best image for the corresponding view. Further, the method 1400 may include a step 1404 of analyzing, using a processing device, the one or more images using two or more machine learning models associated with two or more pathologies. Further, the method 1400 may include a step 1406 of determining, using the processing device, two or more pathological states and at least one of a finding and a measurement associated with the two or more pathological states based on the analyzing of the one or more images. Further, the method 1400 may include a step 1408 of comparing, using the processing device, a current value of the measurement with one or more reference values. Further, the method 1400 may include a step 1410 of generating, using the processing device, a pathological conclusion for the user based on the determining and the comparing. Further, the method 1400 may include a step 1412 of generating, using the processing device, a report data based on the pathological conclusion, the two or more pathological states, and at least one of the finding and the measurement. Further, the method 1400 may include a step 1414 of storing, using a storage device, the one or more images in a database. Further, the method 1400 may include a step 1416 of transmitting, using the communication device, the report data to the user device.

Figure 15:
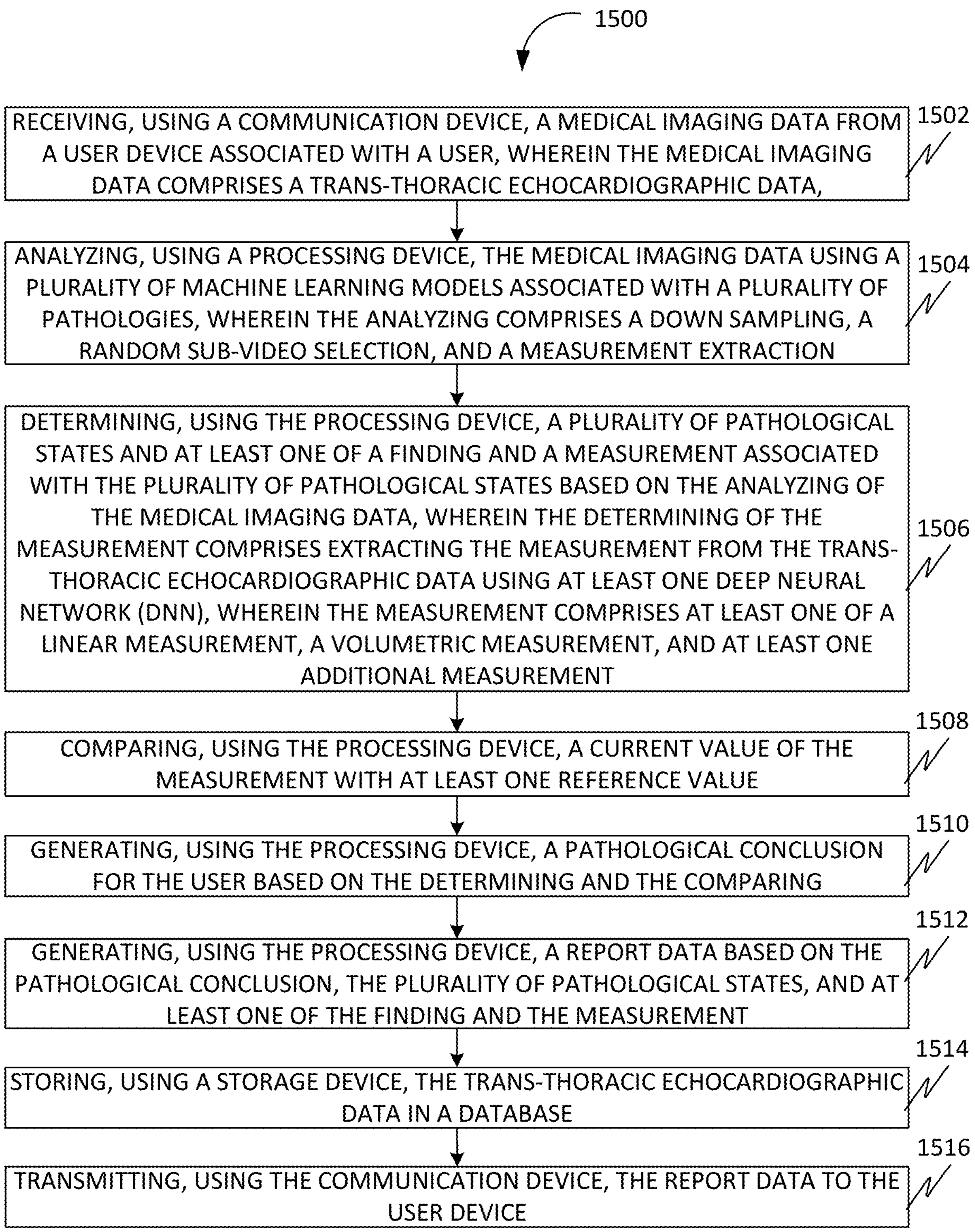
FIG. 15 is a flowchart of a method 1500 for facilitating diagnosis based on medical imaging data, in accordance with some embodiments.

FIG. 15 is a flowchart of a method 1500 for facilitating diagnosis based on medical imaging data, in accordance with some embodiments.

Accordingly, the method 1500 may include a step 1502 of receiving, using a communication device, a medical imaging data from a user device associated with a user. Further, the medical imaging data includes a trans-thoracic echocardiographic data. Further, the method 1500 may include a step 1504 of analyzing, using a processing device, the medical imaging data using two or more machine learning models associated with two or more pathologies. Further, the analyzing includes a down sampling, a random sub-video selection, and a measurement extraction. Further, the method 1500 may include a step 1506 of determining, using the processing device, two or more pathological states and at least one of a finding and a measurement associated with the two or more pathological states based on the analyzing of the medical imaging data. Further, the determining of the measurement may include extracting the measurement from the trans-thoracic echocardiographic data using one or more deep neural networks (DNNs). Further, the measurement may include at least one of a linear measurement, a volumetric measurement, and one or more additional measurements. Further, at least one of the linear measurement, the volumetric measurement, and the one or more additional measurements may include a thickness of the Left Ventricular Inferolateral Wall (LVIWD), a thickness of the Interventricular Septum (LVISD), valve structure diameters of RV Outflow Tract, Right Ventricular Outflow Tract (RVOT), LV Outflow Tract, Left Ventricular Outflow Tract (LVOT), Aortic Valve, Aortic Annulus (AA), Sinus of Valsalva, Sinotubular Junction, and Proximal Ascending Aorta, other measurements such as Pulmonary Artery Pressure, etc. Further, the method 1500 may include a step 1508 of comparing, using the processing device, a current value of the measurement with one or more reference values. Further, the method 1500 may include a step 1510 of generating, using the processing device, a pathological conclusion for the user based on the determining and the comparing. Further, the method 1500 may include a step 1512 of generating, using the processing device, a report data based on the pathological conclusion, the two or more pathological states, and at least one of the finding and the measurement. Further, the method 1500 may include a step 1514 of storing, using a storage device, the trans-thoracic echocardiographic data in a database. Further, the method 1500 may include a step 1516 of transmitting, using the communication device, the report data to the user device.

Figure 16:
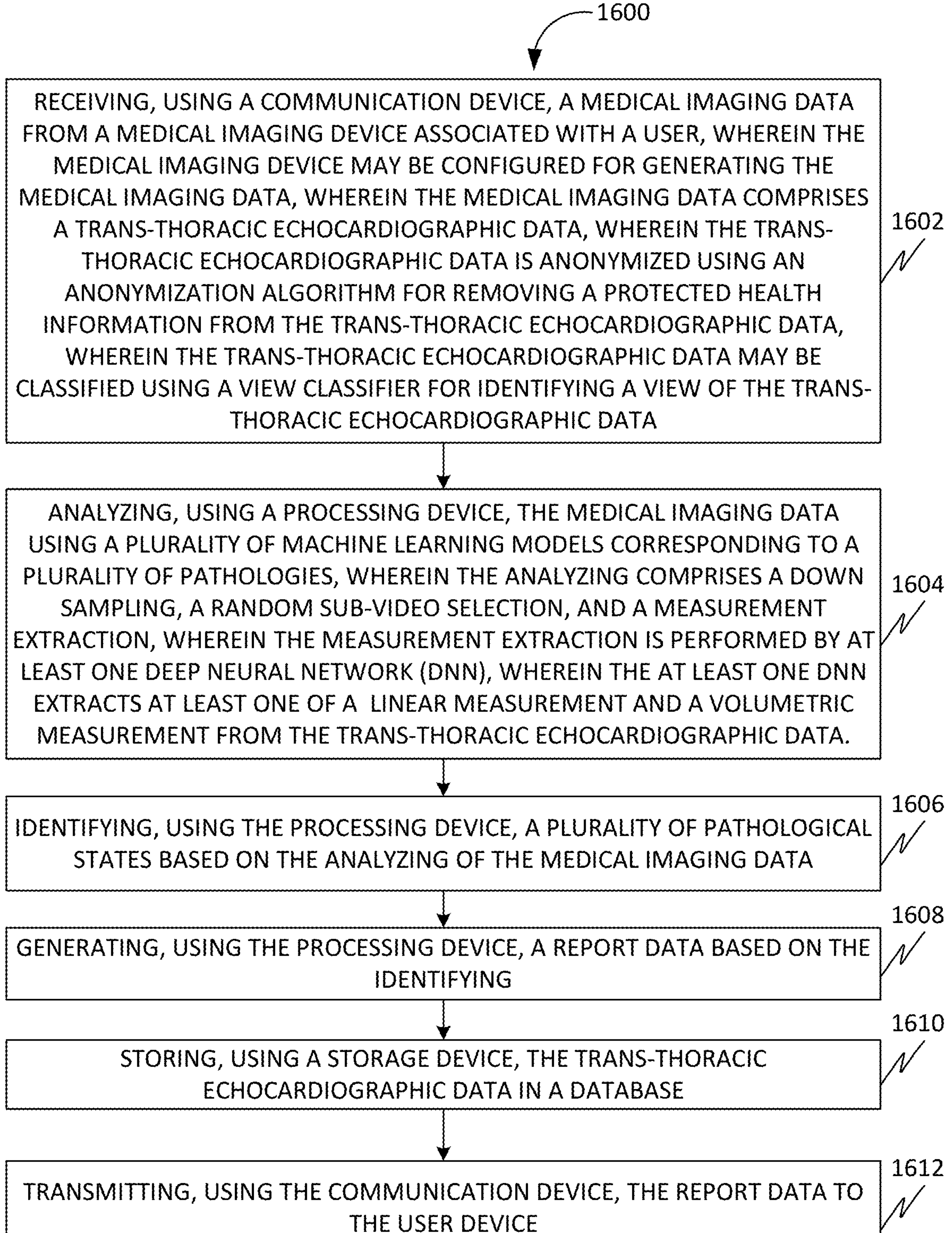
FIG. 16 is a flowchart of a method 1600 for facilitating diagnosis based on medical imaging data, in accordance with some embodiments.

FIG. 16 is a flowchart of a method 1600 for facilitating diagnosis based on medical imaging data, in accordance with some embodiments.

Accordingly, the method 1600 may include a step 1602 of receiving, using a communication device, a medical imaging data from a medical imaging device associated with a user. Further, the medical imaging device may be configured for generating the medical imaging data. Further, the medical imaging data includes a trans-thoracic echocardiographic data. Further, the trans-thoracic echocardiographic data may be anonymized using an anonymization algorithm for removing a protected health information from the trans-thoracic echocardiographic data. Further, the trans-thoracic echocardiographic data may be classified using a view classifier for identifying a view of the trans-thoracic echocardiographic data. Further, the method 1600 may include a step 1604 of analyzing, using a processing device, the medical imaging data using two or more machine learning models corresponding to two or more pathologies. Further, the analyzing includes a down sampling, a random sub-video selection, and a measurement extraction. Further, the measurement extraction may be performed by one or more deep neural networks (DNNs). Further, the one or more DNNs extracts one or more of a linear measurement and a volumetric measurement from the trans-thoracic echocardiographic data. Further, the one or more of the linear measurement and the volumetric measurement may include a thickness of the Left Ventricular Inferolateral Wall (LVIWD), a thickness of the Interventricular Septum (LVISD), valve structure diameters of RV Outflow Tract, Right Ventricular Outflow Tract (RVOT), LV Outflow Tract, Left Ventricular Outflow Tract (LVOT), Aortic Valve, Aortic Annulus (AA), Sinus of Valsalva, Sinotubular Junction, and Proximal Ascending Aorta, other measurements such as Pulmonary Artery Pressure, etc. Further, the method 1600 may include a step 1606 of identifying, using the processing device, two or more pathological states based on the analyzing of the medical imaging data. Further, the method 1600 may include a step 1608 of generating, using the processing device, a report data based on the identifying. Further, the method 1600 may include a step 1610 of storing, using a storage device, the trans-thoracic echocardiographic data in a database. Further, the method 1600 may include a step 1612 of transmitting, using the communication device, the report data to the user device.

FIG. 17 is a table 1700 listing cardia indication and corresponding AUROC for a model, in accordance with some embodiments.

Figure 18:
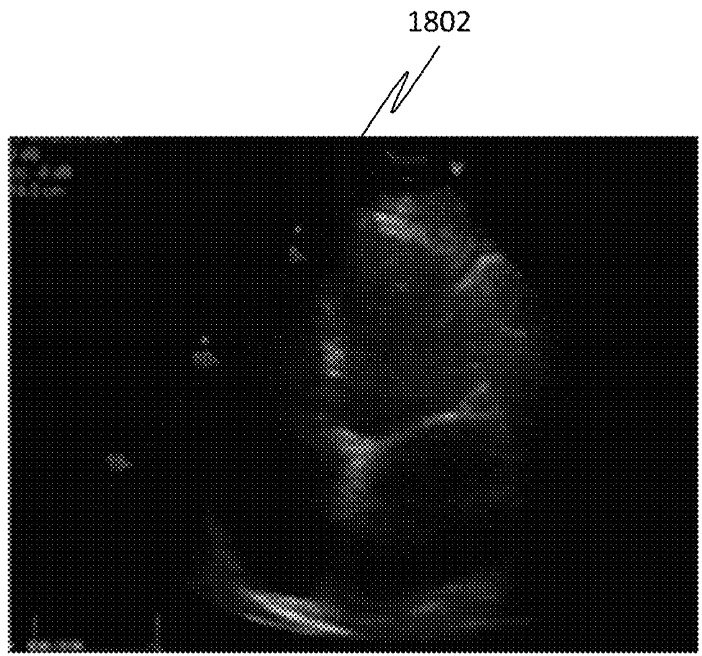
FIG. 18 shows a first apical four-chamber (A4C) view 1802 of echocardiograms showing a pathology (such as HCM), in accordance with some embodiments.

FIG. 18 shows a first apical four-chamber (A4C) view 1802 of echocardiograms showing a pathology (such as HCM), in accordance with some embodiments. Further, the first Apical four-chamber (A4C) view 1802 of studies labeled as consistent with HCM. Further, a section of the cardiologist's report corresponding to the first A4C view 1802 is "consistent with possible reverse stress-induced cardiomyopathy".

Figure 19:
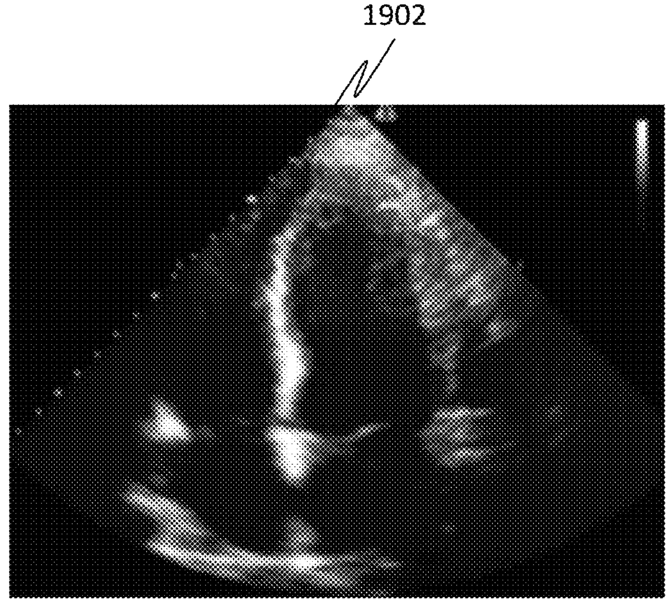
FIG. 19 shows a second apical four-chamber (A4C) view 1902 of the echocardiograms showing the pathology (such as HCM), in accordance with some embodiments.

FIG. 19 shows a second apical four-chamber (A4C) view 1902 of the echocardiograms showing the pathology (such as HCM), in accordance with some embodiments. Further, the second Apical four-chamber (A4C) view 1902 of the studies labeled as consistent with the HCM. Further, a section of the cardiologist's report corresponding to the second A4C view 1902 is "suggestive of apical hypertrophic cardiomyopathy".

Figure 20:
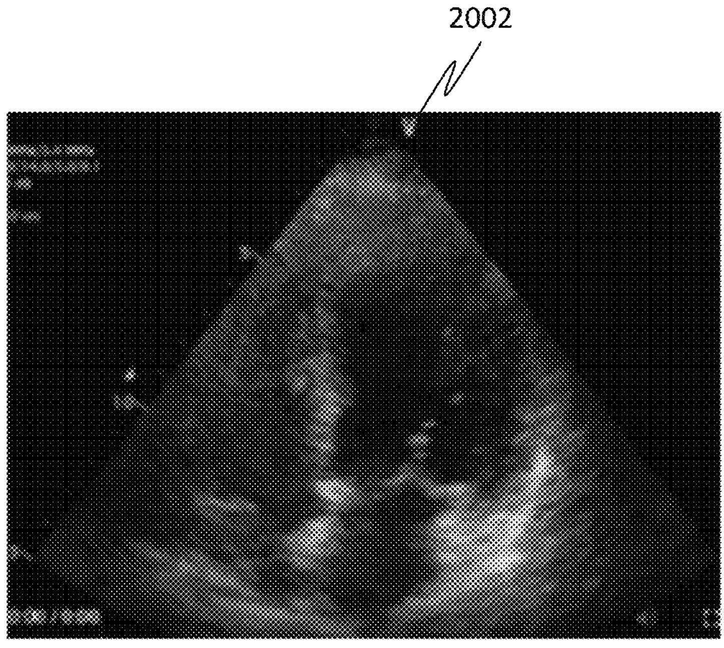
FIG. 20 shows a third apical four-chamber (A4C) view 2002 of the echocardiograms showing the pathology (such as HCM), in accordance with some embodiments.

FIG. 20 shows a third apical four-chamber (A4C) view 2002 of the echocardiograms showing the pathology (such as HCM), in accordance with some embodiments. Further, the third Apical four-chamber (A4C) view 2002 of the studies labeled as consistent with the HCM. Further, a section of the cardiologist's report corresponding to the third A4C view 2002 is "consistent with hypertrophic obstructive cardiomyopathy".

Figure 21:
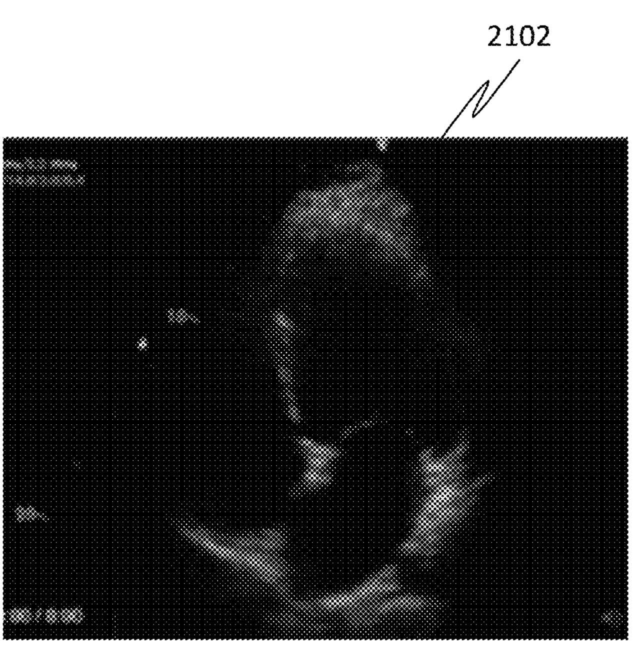
FIG. 21 shows a fourth apical four-chamber (A4C) view 2102 of the echocardiograms showing the pathology (such as HCM), in accordance with some embodiments.

FIG. 21 shows a fourth apical four-chamber (A4C) view 2102 of the echocardiograms showing the pathology (such as HCM), in accordance with some embodiments. Further, the fourth Apical four-chamber (A4C) view 2102 of the studies labeled as consistent with the HCM. Further, a section of the cardiologist's report corresponding to the fourth A4C view 2102 is "Severe cardiomyopathy".

Figure 22:
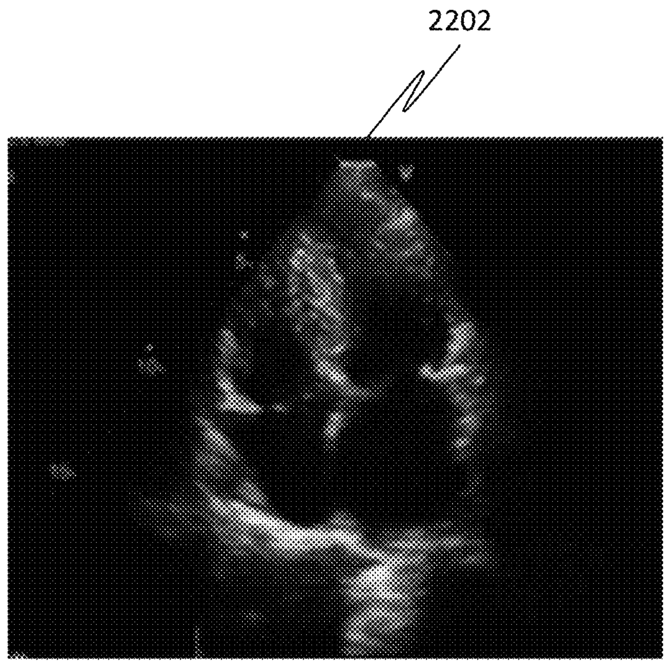
FIG. 22 shows a fifth apical four-chamber (A4C) view 2202 of the echocardiograms showing the pathology (such as HCM), in accordance with some embodiments.

FIG. 22 shows a fifth apical four-chamber (A4C) view 2202 of the echocardiograms showing the pathology (such as HCM), in accordance with some embodiments. Further, the fifth Apical four-chamber (A4C) view 2202 of the studies labeled as consistent with the HCM. Further, a section of the cardiologist's report corresponding to the fifth A4C view 2202 is "further workup for hypertrophic cardiomyopathy or undiagnosed hypertension may be indicated".

Figure 23:
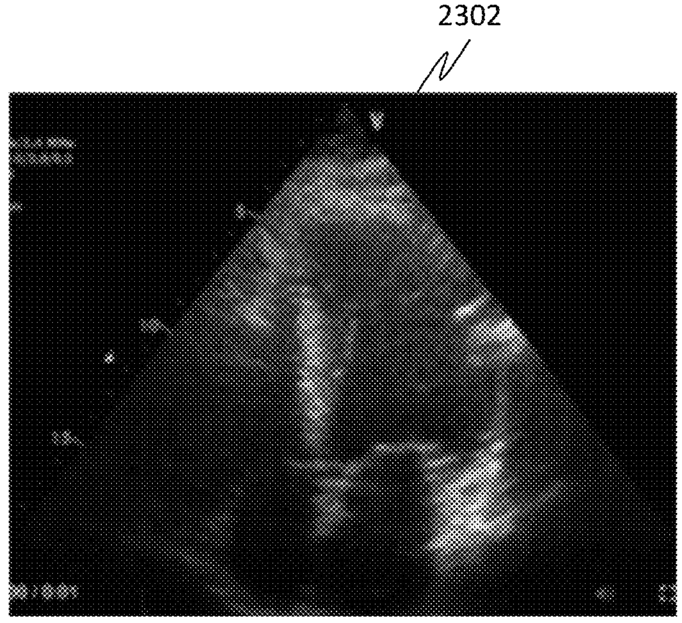
FIG. 23 shows a sixth apical four-chamber (A4C) view 2302 of the echocardiograms showing the pathology (such as HCM), in accordance with some embodiments.

FIG. 23 shows a sixth apical four-chamber (A4C) view 2302 of the echocardiograms showing the pathology (such as HCM), in accordance with some embodiments. Further, the sixth Apical four-chamber (A4C) view 2302 of the studies labeled as consistent with the HCM. Further, a section of the cardiologist's report corresponding to the sixth A4C view 2302 is "further workup for hypertrophic cardiomyopathy may be indicated".

Figure 24:
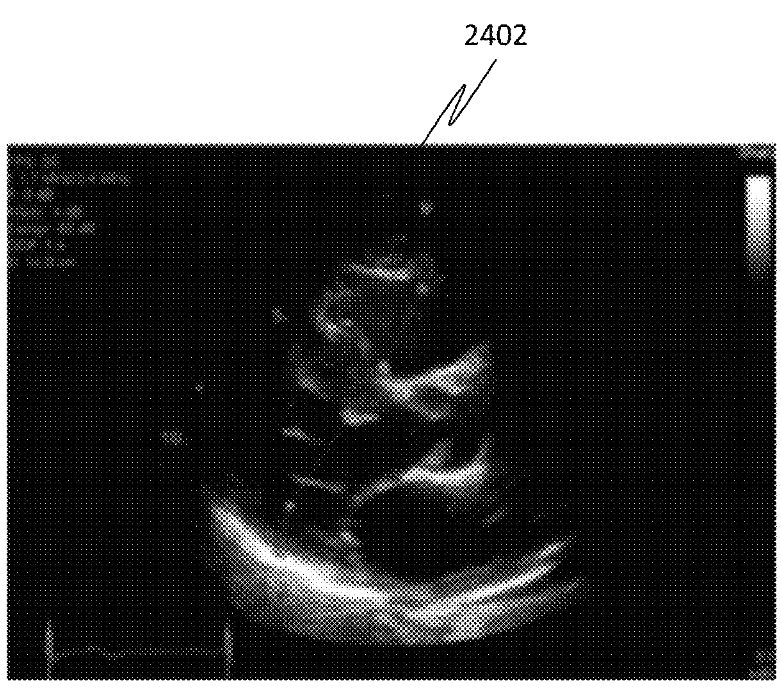
FIG. 24 shows a view 2402 corresponding to a PLAX chamber key point model representative output of a iCardio.ai's measurement model associated with a medical imaging system for facilitating diagnosis, in accordance with some embodiments.

FIG. 24 shows a view 2402 corresponding to a PLAX chamber key point model representative output of a iCardio.ai's measurement model associated with a medical imaging system for facilitating diagnosis, in accordance with some embodiments.

Figure 25:
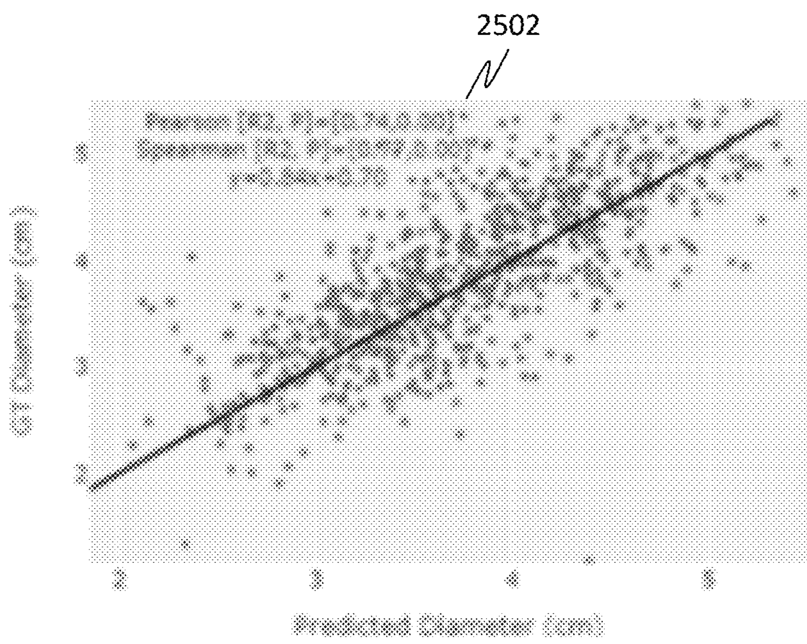
FIG. 25 is a graph 2502 corresponding to a correlation between ground truth lengths and predicted lengths for the Intraventricular septum, one of the measurements in the view 2402, in accordance with some embodiments.

FIG. 25 is a graph 2502 corresponding to a correlation between ground truth lengths and predicted lengths for the Intraventricular septum, one of the measurements in the view 2402, in accordance with some embodiments. Further, the view 2402 and the graph 2502 are a sample output of the iCardio.ai's measurement model for predicting LV wall thickness.

Figure 26:
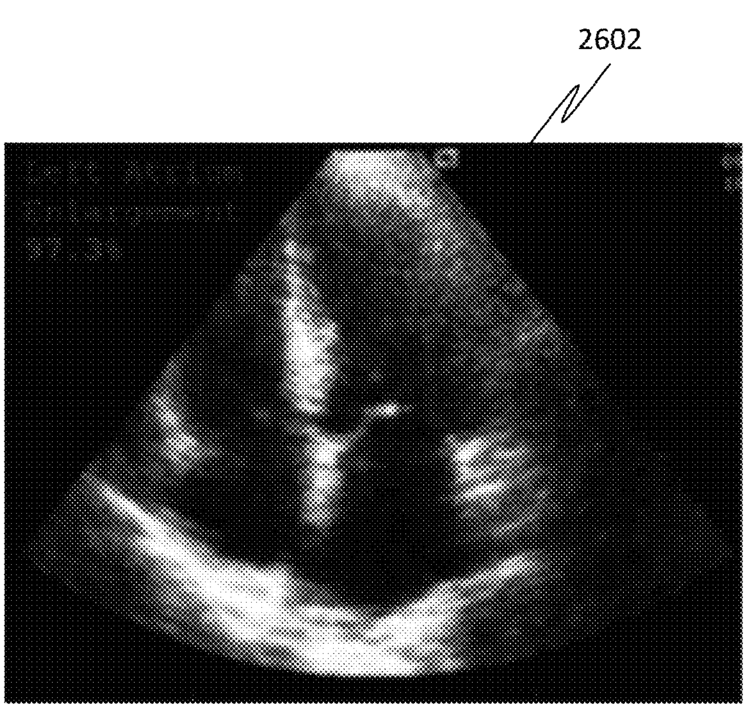
FIG. 26 shows a view 2602 corresponding to an examplary Left atrium enlargement model prediction of the iCardio.ai's measurement model associated with the medical imaging system for facilitating diagnosis, in accordance with some embodiments.

FIG. 26 shows a view 2602 corresponding to an examplary Left atrium enlargement model prediction of the iCardio.ai's measurement model associated with the medical imaging system for facilitating diagnosis, in accordance with some embodiments.

Figure 27:
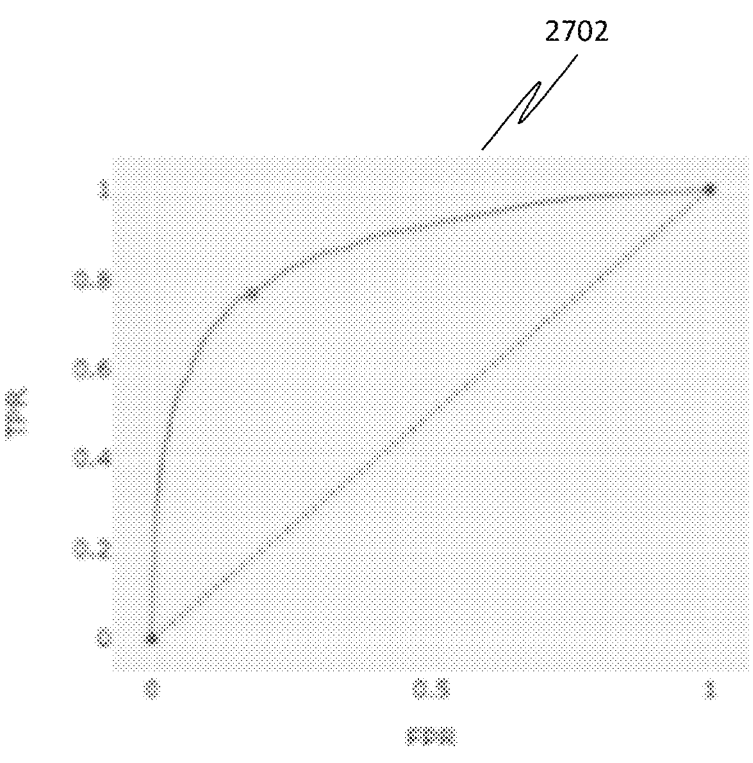
FIG. 27 is a receiver operating characteristic (ROC) plot 2702 for the left atrium enlargement model of the iCardio.ai's measurement model associated with the medical imaging system for facilitating diagnosis, in accordance with some embodiments.

FIG. 27 is a receiver operating characteristic (ROC) plot 2702 for the left atrium enlargement model of the iCardio.ai's measurement model associated with the medical imaging system for facilitating diagnosis, in accordance with some embodiments. Further, the view 2602 and the ROC plot 2702 may be the output of the iCardio.ai's models to predict Basal Septal Hypertrophy with an AUROC of 0.91.

FIG. 28 is a flow diagram of a Training/Validation Data Preprocessing Pipeline 2800 for facilitating diagnosis based on medical imaging data, in accordance with some embodiments. Further, at 2804, the Training/Validation Data Preprocessing Pipeline 2800 anonymizes DICOMs of a patient study stored in a patient study database 2802. Further, at 2806, the Training/Validation Data Preprocessing Pipeline 2800 determines whether a view confidence of the anonymized DICOMS is above a threshold after classifying the anonymized DICOMs using a view classifier 2808. If the view confidence is above the threshold then the anonymized DICOMs classified using the view classifier 2808 are stored in a pathology ML database 2810. Further, the anonymized DICOMs classified using the view classifier 2808 are stored in the pathology ML database 2810. Further, at 2812, the Training/Validation Data Preprocessing Pipeline 2800 manually parses freeform clinician labels of the patient study. Further, at 2814, the Training/Validation Data Preprocessing Pipeline 2800 performs pathology stratification to obtain ground truth HCM labels. Further, the ground truth HCM labels are stored in the pathology ML database 2810.

FIG. 29 is a flow diagram of a pathology (such as HCM) Training Pipeline 2900 for facilitating diagnosis based on medical imaging data, in accordance with some embodiments. Further, at 2904, the pathology Training Pipeline 2900 down samples videos stored in a pathology ML database 2902. Further, at 2906, the pathology Training Pipeline 2900 performs random sub-video selection on video samples obtained after the downsampling. Further, at 2908, the pathology Training Pipeline 2900 performs random augmentation of the video samples obtained after the random sub-video selection. Further, samples obtained after the random augmentation are fed into a base CNN of a wide and deep DNN 2910. Further, the video samples obtained after the downsampling are fed into a measurement extraction network 2912. Further, outputs obtained from the measurement extraction network 2912 are fed into a wide MLP of the wide and deep DNN 2910. Further, a ground truth HCM stratification obtained from the pathology ML database 2902 and HCM predictions obtained from the wide and deep DNN 2910 are fed into a loss function 2914. Further, outputs from the loss function 2914 are used for weight adjustment of the wide and deep DNN 2910 via backpropagation.

FIG. 30 is a flow diagram of an Inference Pipeline 3000 for facilitating diagnosis based on medical imaging data, in accordance with some embodiments. Further, at 3002, the Inference Pipeline 3000 obtains a new study using an API upload. Further, the new study may include multiple videos of multiple views. Further, at 3004, the Inference Pipeline 3000 performs anonymization of multiple videos. Further, at 3006, the Inference Pipeline 3000 performs downsampling of anonymized multiple videos obtained after the anonymization. Further, at 3008, the Inference Pipeline 3000 determines whether the target view and the view confidence of outputs obtained after classifying multiple down-sampled and anonymized videos using a view classifier 3010 is above a threshold. If the outputs are not above the threshold, the outputs are rejected. If the outputs are above the threshold, the outputs are fed into a wide and Deep DNN 3012. Further, the outputs after determining whether the target view and the view confidence of outputs above the threshold, are fed into a measurement extraction network 3014. Further, outputs from the measurement extraction network 3014 are fed into the wide and Deep DNN 3012. Further, pathology predictions are obtained from the wide and Deep DNN 3012.

FIG. 31 is a flow chart of a diagnosis method 3100 for facilitating diagnosis based on medical imaging data, in accordance with some embodiments. Further, at 3102, the diagnosis method 3100 intakes mitral inflow. Further, after 3102 and at 3104 of the diagnosis method 3100, the mitral inflow satisfies a condition "E/A<=0.8+E<=50 cm/s". Further, after 3102 and at 3106 of the diagnosis method 3100, the mitral inflow satisfies a condition "E/A<=0.8+E>50 cm/s or E/A>0.8-<2". Further, after 3102 and at 3108 of the diagnosis method 3100, the mitral inflow satisfies a condition "E/A>=2". Further, based on the mitral inflow 3 criteria are evaluated which are: 1. Average E/e'>14; 2. TR velocity>2.8 m/s; and 3. LA vol. index >34 ml/m$^2$. Further, after 3104 and at 3110 of the diagnosis method 3100, normal LAP grade 1 diastolic dysfunction is determined if 2 or 3 or 3 of 3 criteria are negative. Further, after 3110 and at 3112 of the diagnosis method 3100, the availability of only 2 criteria is determined. Further, after 3112 and at 3114 of the diagnosis method 3100, LAP and diastolic dysfunction grade cannot be determined based on 1 positive and 1 negative criteria. Further, after 3112 and at 3116 of the diagnosis method 3100, increased LAP and grade 2 diastolic dysfunction are determined based on 2 positive criteria. Further, at 3116 of the diagnosis method 3100, increased LAP and grade 2 diastolic dysfunction are also determined based on 2 of 3 or 3 of 3 positive criteria. Further, after 3108 and at 3118 of the diagnosis method 3100, increased LAP and grade 3 diastolic dysfunction are determined. Further, after 3110 and at 3120 of the diagnosis method 3100, CAD or proceeding to a diastolic stress test is considered if normal LAP grade 1 diastolic dysfunction is symptomatic.

FIG. 32 is a flow diagram of a method 3200 for processing a study for facilitating diagnosis based on medical imaging data, in accordance with some embodiments. Further, at 3202, the method 3200 may include uploading a study from a device (smartphone) 3204. Further, the study includes unlabeled DICOMS. Further, the unlabeled DICOMS are fed into a B mode DICOM perspective classifier 3206. Further, the B mode DICOM perspective classifier 3206 outputs perspectives (A4C views). Further, the perspectives are fed into a view quality classifier 3208. Further, the view quality classifier 3208 outputs feature representations (good-quality images). Further, at 3210, the method 3200 may include detecting features and abnormalities (such as left ventricle-basal septal hypertrophy-A4C). Further, at 3212, the method 3200 may include performing post-processing on the detected features. Further, at 3214, the method 3200 may include generating a report after the post-processing. Further, the report may also be generated by retrieving previous studies from a database 3216.

FIG. 33 is a screenshot of a user interface 3300 of a iCardio.ai platform for facilitating diagnosis based on medical imaging data, in accordance with some embodiments.

FIG. 34 shows a 'conclusions' 3402 of a iCardio.ai Brain v1 report 3400 produced by the iCardio.ai platform for facilitating diagnosis based on medical imaging data, in accordance with some embodiments.

FIG. 35 is a 'findings' table 3502 of the iCardio.ai Brain v1 report 3400 produced by the iCardio.ai platform for facilitating diagnosis based on medical imaging data, in accordance with some embodiments.

FIG. 36 is a 'measurements' table 3602 of the iCardio.ai Brain v1 report 3400 produced by the iCardio.ai platform for facilitating diagnosis based on medical imaging data, in accordance with some embodiments.

FIG. 37 shows a first image 3702 of 'visualizations' of the iCardio.ai Brain v1 report 3400 produced by the iCardio.ai platform for facilitating diagnosis based on medical imaging data, in accordance with some embodiments.

FIG. 38 shows a second image 3802 of 'visualizations' of the iCardio.ai Brain v1 report 3400 produced by the iCardio.ai platform for facilitating diagnosis based on medical imaging data, in accordance with some embodiments.

FIG. 39 shows a third image 3902 of 'visualizations' of the iCardio.ai Brain v1 report 3400 produced by the iCardio.ai platform for facilitating diagnosis based on medical imaging data, in accordance with some embodiments.

FIG. 40 shows a fourth image 4002 of 'visualizations' of the iCardio.ai Brain v1 report 3400 produced by the iCardio.ai platform for facilitating diagnosis based on medical imaging data, in accordance with some embodiments.

FIG. 41 shows a fifth image 4102 of 'visualizations' of the iCardio.ai Brain v1 report 3400 produced by the iCardio.ai platform for facilitating diagnosis based on medical imaging data, in accordance with some embodiments.

FIG. 42 shows a sixth image 4202 of 'visualizations' of the iCardio.ai Brain v1 report 3400 produced by the iCardio.ai platform for facilitating diagnosis based on medical imaging data, in accordance with some embodiments.

FIG. 43 shows a seventh image 4302 of 'visualizations' of the iCardio.ai Brain v1 report 3400 produced by the iCardio.ai platform for facilitating diagnosis based on medical imaging data, in accordance with some embodiments.

FIG. 44 shows an eighth image 4402 of 'visualizations' of the iCardio.ai Brain v1 report 3400 produced by the iCardio.ai platform for facilitating diagnosis based on medical imaging data, in accordance with some embodiments.

FIG. 45 shows a ninth image 4502 of 'visualizations' of the iCardio.ai Brain v1 report 3400 produced by the iCardio.ai platform for facilitating diagnosis based on medical imaging data, in accordance with some embodiments.

FIG. 46 shows a tenth image 4602 of 'visualizations' of the iCardio.ai Brain v1 report 3400 produced by the iCardio.ai platform for facilitating diagnosis based on medical imaging data, in accordance with some embodiments.

FIG. 47 shows an eleventh image 4702 of 'visualizations' of the iCardio.ai Brain v1 report 3400 produced by the iCardio.ai platform for facilitating diagnosis based on medical imaging data, in accordance with some embodiments.

Figure 48:
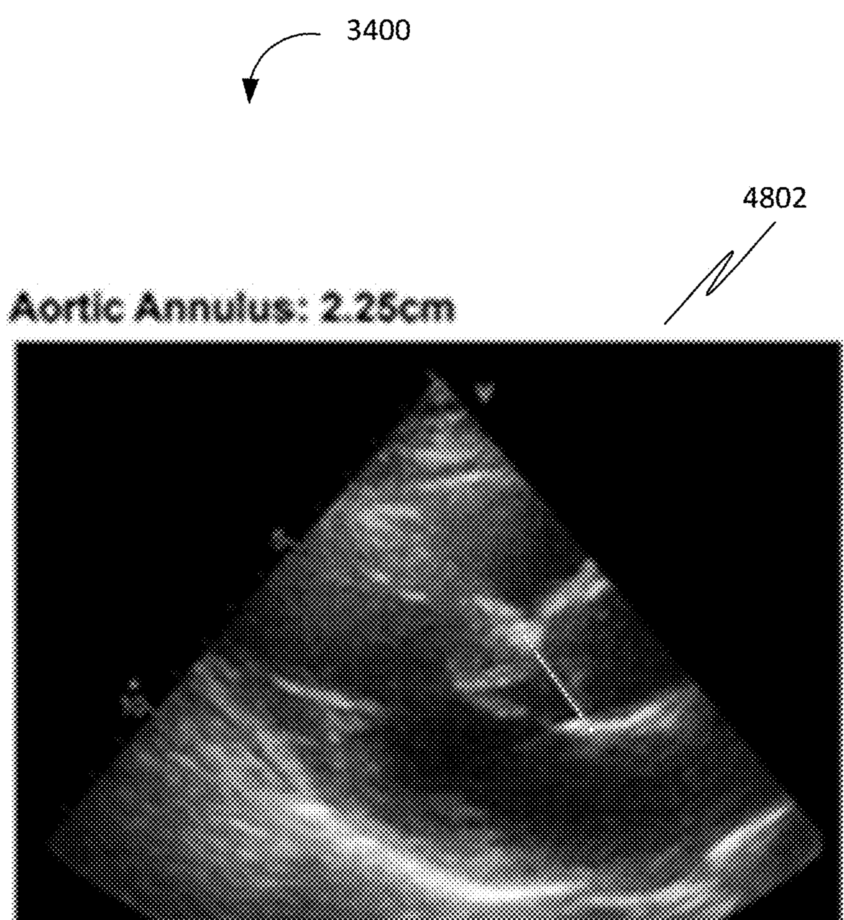
FIG. 48 shows a twelfth image 4802 of 'visualizations' of the iCardio.ai Brain v1 report 3400 produced by the iCardio.ai platform for facilitating diagnosis based on medical imaging data, in accordance with some embodiments.

FIG. 48 shows a twelfth image 4802 of 'visualizations' of the iCardio.ai Brain v1 report 3400 produced by the iCardio.ai platform for facilitating diagnosis based on medical imaging data, in accordance with some embodiments.

Figure 49:
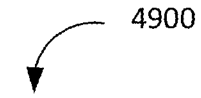
FIG. 49 is a table 4900 representing a pathology with corresponding Echo, Accuracy, and ROCAUC of a model associated with the iCardio.ai platform for facilitating diagnosis based on medical imaging data, in accordance with some embodiments.

FIG. 49 is a table 4900 representing a pathology with corresponding Echo, Accuracy, and ROCAUC of a model associated with the iCardio.ai platform for facilitating diagnosis based on medical imaging data, in accordance with some embodiments.

FIG. 50 illustrates a machine learning model 5000 for facilitating diagnosis based on medical imaging data, in accordance with some embodiments. Further, the machine learning model 5000 may include a multi-view ensemble model 5010 and a plurality of single-view models 5002-5008.

Further, the plurality of single-view models 5002-5008 may include an N number of single-view models. Further, the N number of single-view models may be associated with an N number of specific pathologies. Further, the N number of single-view models may produce an N number of outputs corresponding to the N number of specific pathologies.

Further, the multi-view ensemble model 5010 may take the N number of outputs from the N number of single-view models and combine the N number of outputs to produce a single output. Further, the single output may be a single pathology propensity score. Further, the multi-view ensemble model 5010 uses machine learning to optimally weigh the N number of outputs of the N number of single-view models to generate the single output.

Further, in some embodiments, the multi-view ensemble model 5010 may be trained independently from the N number of single-view models.

Further, in some embodiments, the multi-view ensemble model 5010 may be trained jointly with the N number of single-view models.

Further in some embodiments, the multi-view ensemble model 5010 may take into account measurements concerning a patient. Further, the measurements may be estimated using a machine learning (ML) model from the data. Further, the data may be provided by a physician. Further, the measurements may include data such as patient age, BMI, sex, etc. Further, the data of the measurements may not be obtained from echo imagery.

FIG. 51 illustrates a multi-pathology model 5100 for facilitating diagnosis based on medical imaging data, in accordance with some embodiments. Further, the multi-pathology model 5100 may include a base network 5102. Further, Echo data is fed to the base network 5102. Further, the base network 5102 encodes the Echo data to a lower dimensional space 5104. Further, a plurality of pathologies and one or more measurements are obtained from the lower dimensional space 5104.

FIG. 52 is a flow diagram of a method 5200 for facilitating diagnosis based on medical imaging data, in accordance with some embodiments. Further, the medical imaging data may include echocardiograms. Further, at 5202, the method 5200 may include feeding the echocardiogram to a feature extractor 5204. Further, at 5206, the method 5200 may include obtaining low-dimensional representations from the feature extractor 5204. Further, at 5208, the method 5200 may include performing direct text decoding of the low-dimensional representations using a text decoder 5210. Further, at 5212, the method 5200 may include performing classifier-based decoding using a pathology classifier 5214. Further, the performing of the classifier-based decoding may include obtaining a plurality of pathologies probabilities at 5216 of the method 5200, formatting the plurality of pathologies probabilities at 5218 of the method 5200, and processing the plurality of formatted pathologies probabilities using a text-text or multimodal language model 5220. Further, at 5222, the method 5200 may include obtaining text outputs after the direct text decoding and the classifier-based decoding.

FIG. 53 is a flow diagram of a method 5300 for facilitating diagnosis based on medical imaging data, in accordance with some embodiments. Further, the medical imaging data may include echocardiograms. Further, at 5302, the method 5300 may include feeding the echocardiogram to a feature extractor 5304. Further, at 5306, the method 5300 may include obtaining low-dimensional representations from the feature extractor 5304. Further, at 5308, the method 5300 may include obtaining a first reply by feeding the low-dimensional representations and a first chat message 5312 to a first text decoder 5310. Further, at 5314, the method 5300 may include obtaining a second reply by feeding the low-dimensional representations, a second chat message 5318, and the first reply to a second text decoder 5316.

FIG. 54 illustrates a system 5400 for producing clinically relevant measurements and findings, in accordance with some embodiments. Further, the system 5400 may include an anonymizer 5402, an artificial intelligence (AI) model module 5404, a cloud platform 5406, and a retraining module 5408. Further, echo image data is fed into the anonymizer 5402. Further, an output from the anonymizer 5402 is fed into the AI model module 5404. Further, the AI model module 5404 provides an output. Further, the output provided by the AI model module 5404 is reviewed by a clinician. Further, a clinician reviewed output is uploaded to the cloud platform 5406. Further, the retraining module 5408 may communicate with the cloud platform 5406 and the AI model module 5404. Further, the retraining module 5408 may retrain an AI model of the AI model module 5404 using the clinician reviewed output. Further, a report may be generated using the output from the AI model module 5404.

Figure 55:
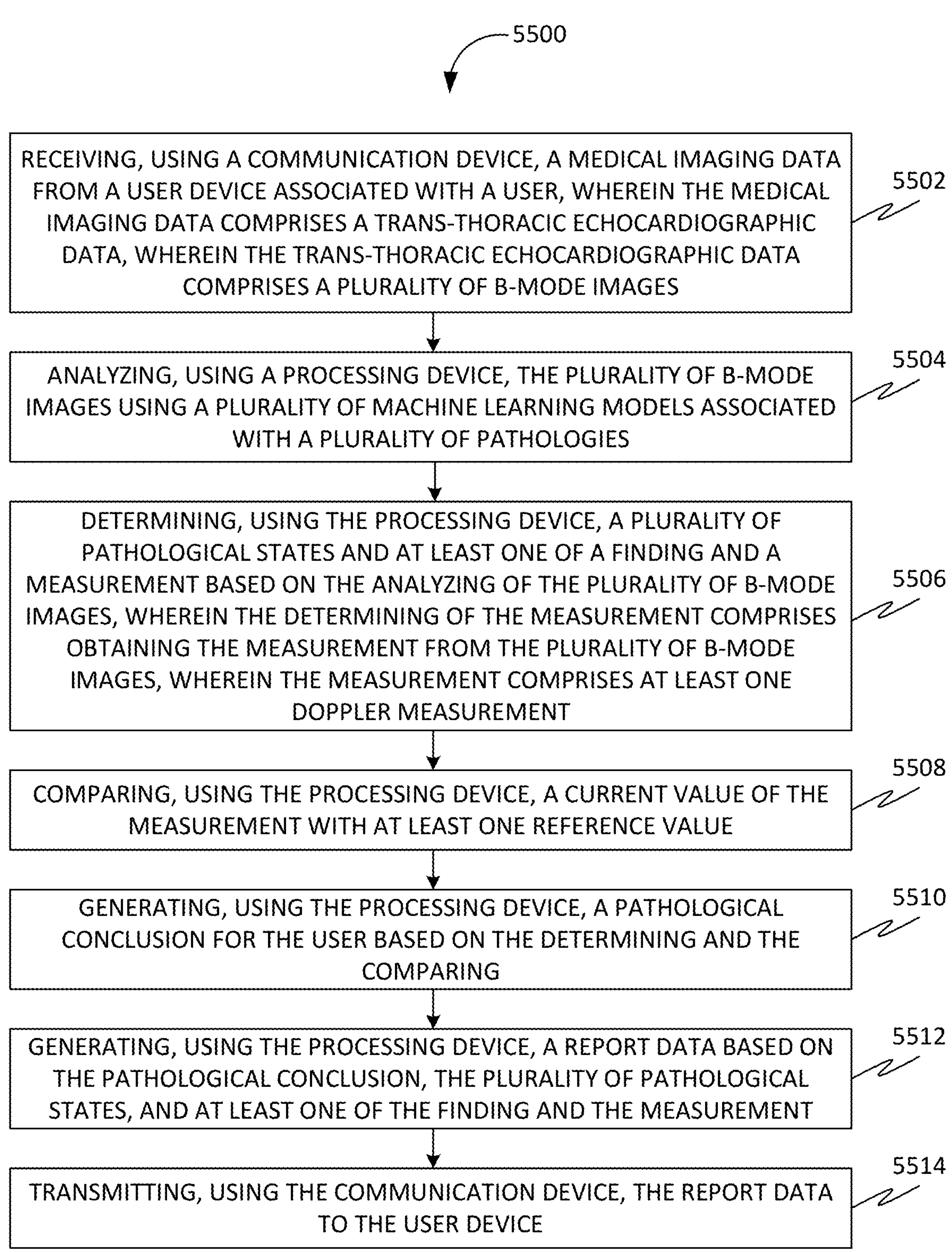
FIG. 55 is a flowchart of a method 5500 for facilitating diagnosis based on medical imaging data, in accordance with some embodiments.

FIG. 55 is a flowchart of a method 5500 for facilitating diagnosis based on medical imaging data, in accordance with some embodiments.

Accordingly, the method 5500 may include a step S502 of receiving, using a communication device, a medical imaging data from a user device associated with a user. Further, the medical imaging data may include a trans-thoracic echocardiographic data. Further, the trans-thoracic echocardiographic data may include two or more b-mode images. Further, the method 5500 may include a step S504 of analyzing, using a processing device, the two or more b-mode images using two or more machine learning models associated with two or more pathologies. Further, the method 5500 may include a step S506 of determining, using the processing device, two or more pathological states and at least one of a finding and a measurement associated with the two or more pathological states based on the analyzing of the two or more b-mode images. Further, the determining of the measurement may include obtaining the measurement from the two or more b-mode images. Further, the measurement may include one or more doppler measurements. Further, the method 5500 may include a step S508 of comparing, using the processing device, a current value of the measurement with one or more reference values. Further, the method 5500 may include a step S510 of generating, using the processing device, a pathological conclusion for the user based on the determining and the comparing. Further, the method 5500 may include a step S512 of generating, using the processing device, a report data based on the pathological conclusion, the two or more pathological states, and at least one of the finding and the measurement. Further, the method 5500 may include a step S514 of transmitting, using the communication device, the report data to the user device.

Figure 56:
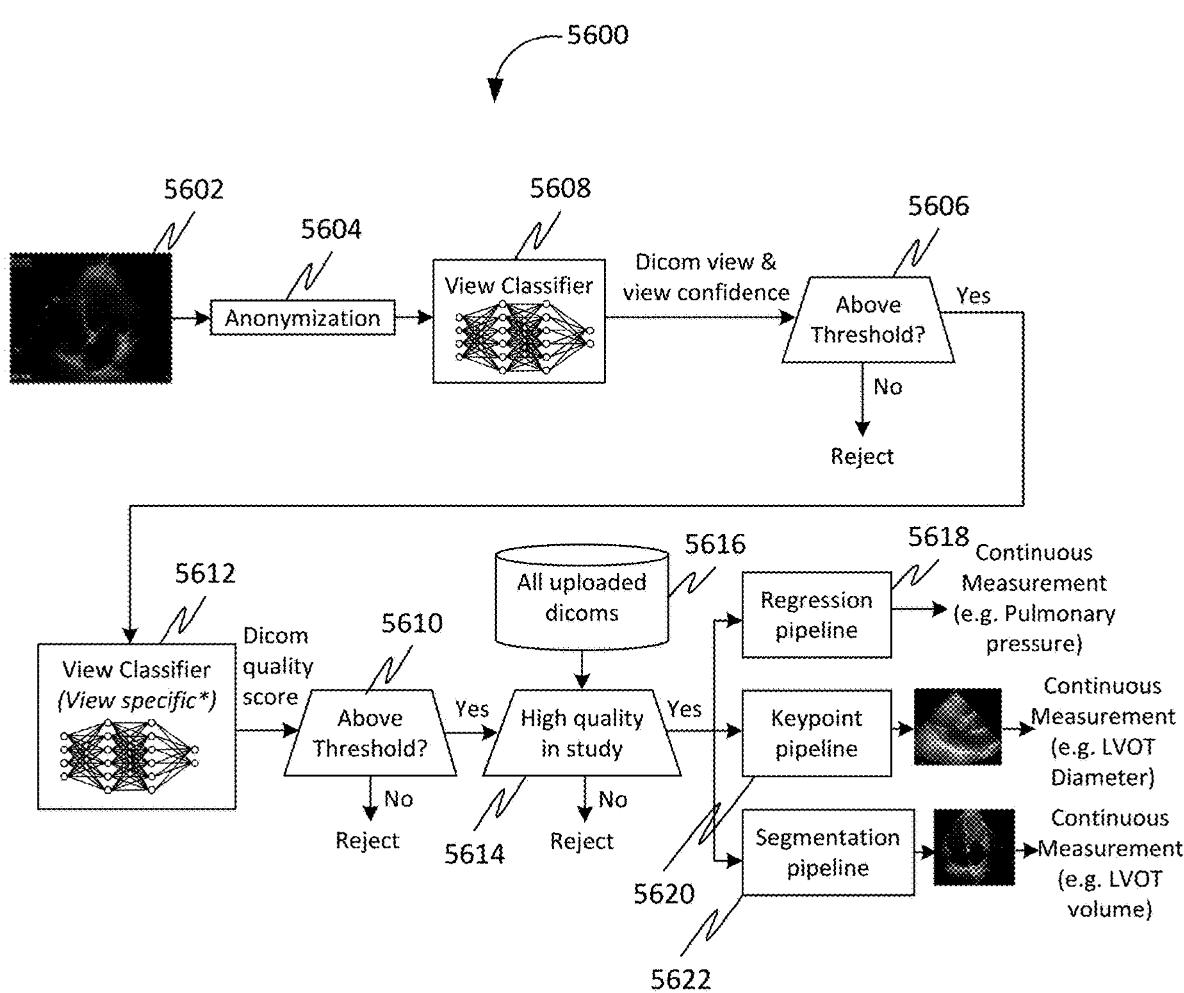
FIG. 56 is a flow diagram of a general DICOM pipeline 5600 facilitating diagnosis based on medical imaging data, in accordance with some embodiments.

FIG. 56 is a flow diagram of a general DICOM pipeline 5600 facilitating diagnosis based on medical imaging data, in accordance with some embodiments. Further, the medical imaging data may include DICOMs. Further, at step S602 of the general DICOM pipeline 5600, the DICOMs from a single echocardiography exam are obtained. Further, at step S604 of the general DICOM pipeline 5600, the DICOMs are anonymized. Further, at step S606 of the general DICOM pipeline 5600, whether a DICOM view and a view confidence obtained by classifying the DICOMs using a view classifier 5608 are above a threshold is determined. If the DICOM view and the view confidence are below the threshold then the DICOMs are rejected. If the DICOM view and the view confidence are above the threshold then at step S610 of the general DICOM pipeline 5600, whether a DICOM quality score obtained by classifying the DICOMs using another view classifier (view-specific classifier) 5612, is above a threshold is determined. If the DICOM quality score is below the threshold then the DICOMs are rejected. Further, if the DICOM quality score is above the threshold then at step S614 of the general DICOM pipeline 5600, whether the DICOMs uploaded in a database 5616 are of a high quality is determined. If the DICOMs are not of high quality then the DICOMs are rejected, and if the DICOMs are of high quality then the DICOMs are processed using a regression pipeline 5618, a keypoint pipeline 5620, a segmentation pipeline 5622. Further, the regression pipeline 5618 produces a continuous measurement (such as pulmonary pressure). Further, the keypoint pipeline 5620 produces a continuous measurement (such as an LVOT diameter).

Further, the segmentation pipeline 5622 produces a continuous measurement (such as LVOT volume).

FIG. 57 is a flow diagram of a classification pipeline 5700 facilitating diagnosis based on medical imaging data, in accordance with some embodiments. Further, the medical imaging data may include DICOMs. Further, at step S702 of the classification pipeline 5700, a single DICOM from a study is obtained. Further, the DICOM is a video (H×W×Nf×3). Further, at step S704 of the classification pipeline 5700, the DICOM is preprocessed by cropping, monochroming, and frame cropping of the DICOM to obtain a video (He×We×24). Further, at step S706 of the classification pipeline 5700, the video (He×We×24) is downsampled to obtain a video (224×224×24). Further, at step S708 of the classification pipeline 5700, the video (224×224×24) is classified using a classifier CNN to obtain classifier softmax scores.

Figure 58:
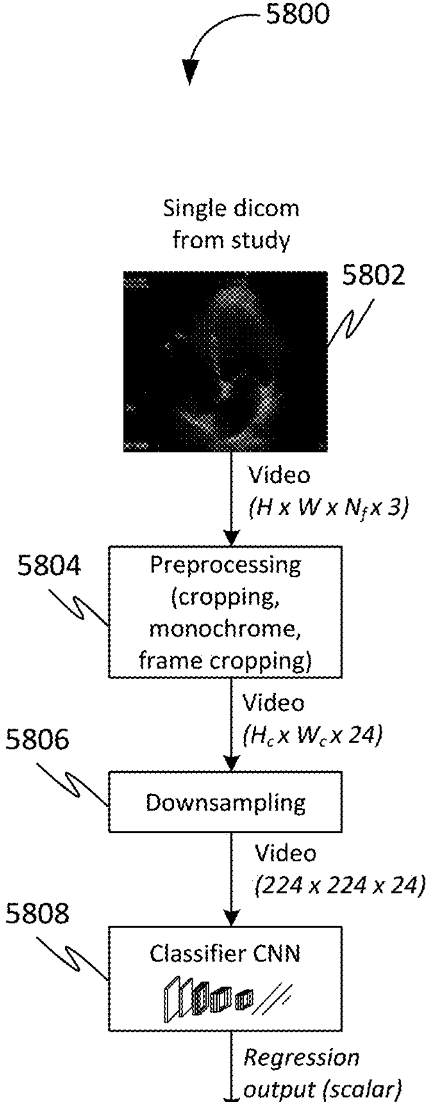
FIG. 58 is a flow diagram of a regression pipeline 5800 facilitating diagnosis based on medical imaging data, in accordance with some embodiments.

FIG. 58 is a flow diagram of a regression pipeline 5800 facilitating diagnosis based on medical imaging data, in accordance with some embodiments. Further, the medical imaging data may include DICOMs. Further, at step S802 of the regression pipeline 5800, a single DICOM from a study is obtained. Further, the DICOM is a video (H×W×Nf×3). Further, at step S804 of the regression pipeline 5800, the DICOM is preprocessed by cropping, monochroming, and frame cropping of the DICOM to obtain a video (He×We×24). Further, at step S806 of the regression pipeline 5800, the video (He×We×24) is downsampled to obtain a video (224×224×24). Further, at step S808 of the regression pipeline 5800, the video (224×224×24) is classified using a classifier CNN to obtain regression output (scalar).

Figure 59:
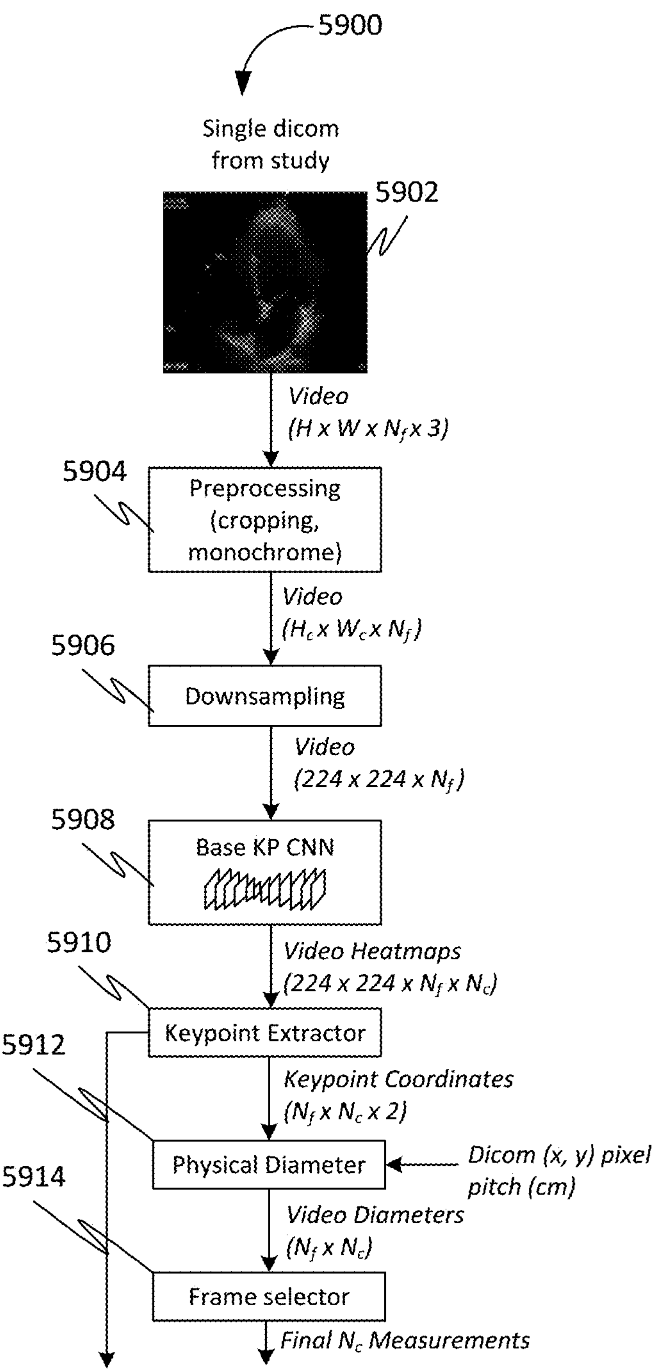
FIG. 59 is a flow diagram of a keypoint pipeline 5900 facilitating diagnosis based on medical imaging data, in accordance with some embodiments.

FIG. 59 is a flow diagram of a keypoint pipeline 5900 facilitating diagnosis based on medical imaging data, in accordance with some embodiments. Further, the medical imaging data may include DICOMs. Further, at step S902 of the keypoint pipeline 5900, a single DICOM from a study is obtained. Further, the DICOM is a video (H×W×Nf×3). Further, at step S904 of the keypoint pipeline 5900, the DICOM is preprocessed by cropping and monochroming the DICOM to obtain a video (He×We×Nf). Further, at step S906 of the keypoint pipeline 5900, the video (He×We×Nf) is downsampled to obtain a video (224×224×Nf). Further, at step S908 of the keypoint pipeline 5900, the video (224×224×Nf) is processed using a Base KP CNN to obtain video heatmaps (224×224×Nf×Nc). Further, at step S910 of the keypoint pipeline 5900, keypoint coordinates (Nf×Nc×2) are obtained from the video heatmaps (224×224×Nf×Nc) using a keypoint extractor. Further, at step S912 of the keypoint pipeline 5900, video diameters (Nf×Nc) are obtained from keypoint coordinates (Nf×Nc×2) using a physical diameter which is associated with DICOM (x, y) and pixel pitch (cm). Further, at step S914 of the keypoint pipeline 5900, final Nc measurements are obtained from the video diameters (Nf×Nc) using a frame selector.

Figure 60:
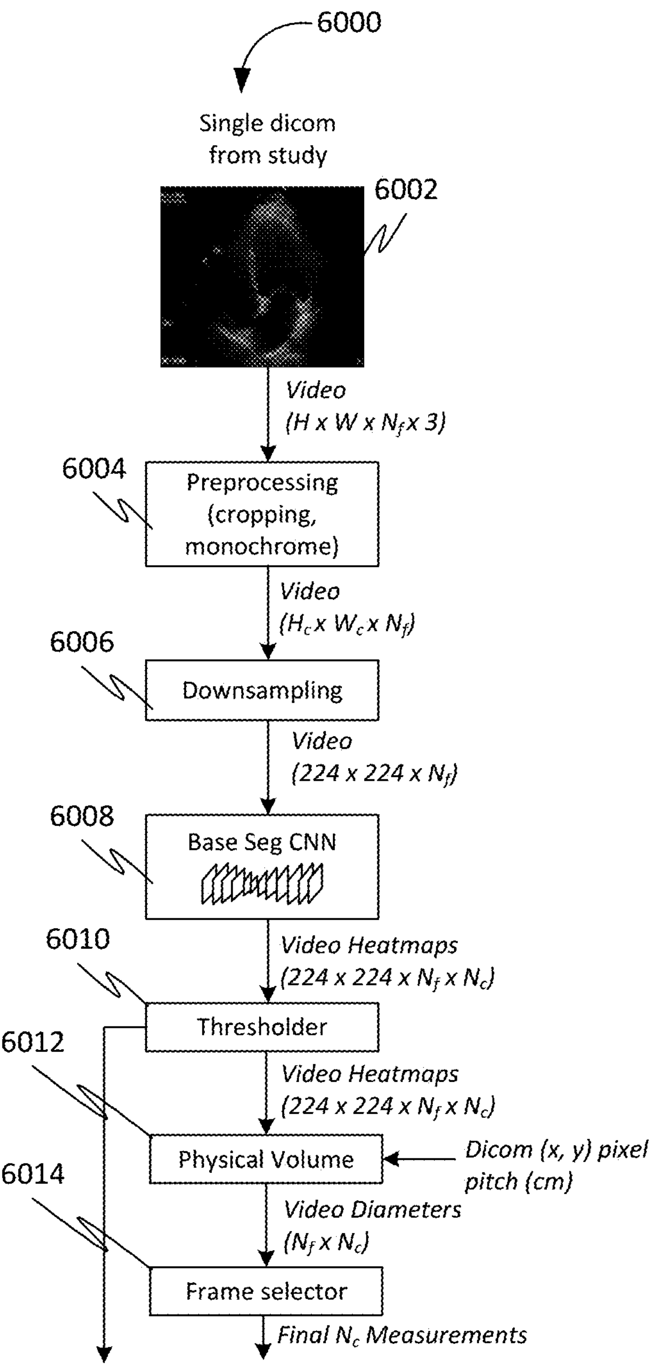
FIG. 60 is a flow diagram of a segmentation pipeline 6000 facilitating diagnosis based on medical imaging data, in accordance with some embodiments.

FIG. 60 is a flow diagram of a segmentation pipeline 6000 facilitating diagnosis based on medical imaging data, in accordance with some embodiments. Further, the medical imaging data may include DICOMs. Further, at step 6002 of the segmentation pipeline 6000, a single DICOM from a study is obtained. Further, the DICOM is a video (H×W×Nf×3). Further, at step 6004 of the segmentation pipeline 6000, the DICOM is preprocessed by cropping and monochroming the DICOM to obtain a video (He×We×Nf). Further, at step 6006 of the segmentation pipeline 6000, the video (He×We×Nf) is downsampled to obtain a video (224×224×Nf). Further, at step 6008 of the segmentation pipeline 6000, the video (224×224×Nf) is processed using a Base Seg CNN to obtain video heatmaps (224×224×Nf×Nc). Further, at step 6010 of the segmentation pipeline 6000, video heatmaps (224×224×Nf×Nc) are obtained from the video heatmaps (224×224×Nf×Nc) using a thresholder. Further, at step 6012 of the segmentation pipeline 6000, video diameters (Nf×Nc) are obtained from video heatmaps (224×224×Nf×Nc) using a physical volume which is associated with DICOM (x, y) and pixel pitch (cm). Further, at step 6014 of the segmentation pipeline 6000, final Nc measurements are obtained from the video diameters (Nf×Nc) using a frame selector.

Functionality

Logical Structure and Algorithms

1. General DICOM pipeline: The general study algorithm pipeline, as shown in FIG. 56, includes a study consisting of a set of DICOMs obtained from a single echocardiography exam. Further, the study is submitted to the iCardio.ai Brain either through a web app or API. Upon submission, the first processing step associated with the general study algorithm pipeline include anonymizing the set of DICOMs to remove any PHI from the data, including from DICOM metadata and image pixels. After anonymization, the original DICOMs are deleted to avoid storing PHI and only the anonymized DICOMs are used for further processing. After anonymization, each DICOM goes through the view classifier (classification) pipeline. Further, the classification pipeline outputs a view prediction (e.g. A4C) and a view confidence. Further, the view confidence is a scalar between 0 and 1 and expresses confidence in the view prediction. If the DICOM's view confidence is below VIEW_CONFIDENCE_REJECT_THRESHOLD, then the DICOM is rejected. If the DICOM's view confidence is above VIEW_CONFIDENCE_REJECT_THRESHOLD, but below VIEW_CONFIDENCE_WARNING_THRESHOLD, then the DICOM is used, but a warning is issued that it is a low quality DICOM. As an additional safeguard for image quality, the iCardio.ai Brain includes a dedicated binary quality pipeline for A4C and PLAX views. The dedicated binary quality pipeline is based on a binary classifier and trained on manual annotations of image quality from experienced technicians. The output of the dedicated binary quality pipeline is a DICOM quality score between 0 and 1. Further, the quality score and the view confidence score are overlapping but are not identical, and focus on different aspects of image quality. For example, a blurry or low-contrast DICOM obtained from a well-positioned A4C view has a high view confidence score but a low quality score. As with the view confidence score, if the DICOM's quality score is below QUALITY_REJECT_THRESHOLD, then the DICOM is rejected. If the DICOM's quality score is above QUALITY_REJECT_THRESHOLD, but below QUALITY_WARNING_THRESHOLD, then the DICOM is used, but a warning is issued that it is a low quality DICOM. After both the quality score is obtained, the DICOM of each view with the highest quality score is used for upstream processing. For example, if a study has 3 DICOMs estimated to be in the A4C view with quality scores of {0.56, 0.89, 0.99}, the DICOM with a score of 0.99 may be used for all upstream pipelines which use the A4C view. Upstream pipeline types include regression pipelines, keypoint pipelines, and segmentation pipelines.

2. Individual AI Pipelines: The iCardio.ai Brain consists of 4 types of AI pipelines, as shown in FIG. 57, classification pipelines, regression pipelines, keypoint pipelines, and segmentation pipelines. In the context of the iCardio.ai Brain, a pipeline refers to the full set of processing of an AI algorithm. The input to a pipeline is a single DICOM. The output is varied and depends on the type of pipeline. All of iCardio.ai Brain's pipelines begin with a relatively similar set of preprocessing steps. Further, the preprocessing steps may include:

- Monochrome: In monochrome, only a first (red) channel from a plurality of channels (red, blue, and green) is used in each DICOM video.
- Cropping: Cropping is done using an automated algorithm that removes superfluous pixels around an actual echocardiogram (echo). Examples of cropped images are shown in FIG. 58. Cropping is done based on the assumption that only the actual echo itself changes across frames of a DICOM, while superfluous blank pixels and text do not change. For each pixel (value range 0 to 256), the absolute change in pixel values between adjacent frames is averaged over all frames in the DICOM. If this value is below the threshold, CROP_CHANGE_THRESHOLD, that pixel is deemed superfluous. The cropping border is determined by the first non-superfluous pixel from each border.
- Downsampling: In downsampling, the cropped video is downsampled to 256×256 (width×height) pixels.
- Frame cropping: Dicom imagery can have an arbitrary amount of frames. The iCardio.ai Brain selects the first $N_f$ frames for each pipeline, where $N_f$ is pipeline specific. Further, the frame cropping is done in order to not overwhelm upstream processing.
- Normalization: In normalization, imagery is converted from UINT8 format with values ranging from 0 to 256 to Float format with values ranging from 0 to 1.

After preprocessing and downsampling, each DICOM is represented by an $\{N_f, H, W, I\}$ tensor with values ranging from 0 to 1. At this point, processing varies based on the type of pipeline. Further, the types of pipelines are described below:

Classification Pipelines: In the classification pipelines, the input tensor goes through a DNN which outputs a tensor of shape $\{N_f, N_c\}$ where $N_c$ is the number of output classes of the classifier. This tensor consists of class probabilities between 0 and 1 for each classifier class. There are two classification pipelines used in the iCardio.ai Brain, the view classification pipeline and the quality classifier. The view classification pipeline has 28 output classes and the quality classifier has two output classes: "good quality" and "bad quality". Each frame of the tensor is processed independently (i.e. it is the batch dimension of the DNN). Afterward, the class probabilities are averaged across frames to obtain an $\{N_c, 1\}$ tensor. The class with the highest probability is the estimated class. The DNN architecture used for classification and regression pipelines in the iCardio.ai Brain is the Inception Resnet V2 architecture.

Regression Pipelines: Regression pipelines are similar to the classification pipelines except that they only output a single scalar rather than a vector of class probabilities. Averaging is also done across frames. The only regression pipeline in the iCardio.ai Brain is the Pulmonary pressure pipeline.

Segmentation Pipelines: Segmentation pipelines put the input tensor through an image-to-image DNN which outputs a set of $N_h$ heatmaps of the same height and width as the original image. $N_h$ is determined by the number of anatomical regions the model is segmenting (e.g. left ventricle, right ventricle) as well as an additional channel for background. The heatmap values correspond to probabilities that the given pixel is a member of that class. The final class predictions for each pixel are determined by which channel has the highest probability. The iCardio.ai Brain consists of 2 segmentation pipelines to segment the left ventricle in A4C and A2C views. Once a contiguous area is identified for each anatomical region, its volume is determined via the method of disks. Further, to reduce volume jitter, the volume in each frame is averaged with that of adjacent frames using a moving average filter. After a volume is determined for each frame, the systolic and diastolic keyframes are selected based on the min and max volumes of the anatomical structure. For example, peak systole is defined as the frame where the left ventricle has the minimum volume and peak diastole is defined as the frame where the left ventricle has the maximum volume.

The DNN architecture used for segmentation and keypoint pipelines in the iCardio.ai Brain is the DeepLabV3+ architecture.

Keypoint Pipelines: Like the segmentation pipelines, the keypoint pipelines consist of an image-to-image DNN which also outputs $N_h$ heatmaps of the same height and width as the original image. $N_h$ is determined by the number of key points in the model, with an additional heatmap for the background. The maximum pixel value in each heatmap is used for the x and y coordinates of each keypoint. To reduce jitter in keypoint positions, the keypoint x and y coordinates in each frame are averaged with that of adjacent frames using a moving average filter. Physical diameters are then obtained by using the following formula:

$$d = x1 - x2 * px2 + y1 - y2 * py2$$

Where $(x_1, y_1)$ and $(x_2, y_2)$ correspond to the x and y coordinates of the two key points forming the endpoints of each linear measurement, and $(p_x, p_y)$ corresponds to the pixel pitches of the DICOM in the x and y dimensions. As with segmentation pipelines, after linear measurements are determined for each frame, the systolic and diastolic keyframes are selected based on the min and max lengths of a given measurement.

3. Conclusions: For each measurement, the iCardio.ai Brain has a reference range found in healthy individuals. If the estimated value of a measurement is outside this range, this will be mentioned in the report conclusions.

FIG. 61 shows a first DICOM image 6100 associated with a plurality of pipelines, in accordance with some embodiments. Further, lines show a cropped portion of the first DICOM image 6100.

FIG. 62 shows a second DICOM image 6200 associated with the plurality of pipelines, in accordance with some embodiments. Further, lines show a cropped portion of the second DICOM image 6200.

FIG. 63 shows a third DICOM image 6300 associated with the plurality of pipelines, in accordance with some embodiments. Further, lines show a cropped portion of the third DICOM image 6300.

Report Generation

The disclosed software produces reports which may be consumed in several ways, such as a report presented by a GUI in a single-page web application, a PDF report, and a JSON-formatted report that allows integration with other systems. Further, the GUI presents a tabular report that is rendered with the wireframe structure. Further, the PDF report is generated by rendering an HTML page which is then converted to a PDF format using off-the-shelf open-source software. Further, the JSON report is created by serializing the persisted data to a schema.

Architecture

Architecture Diagrams

Figure 64:
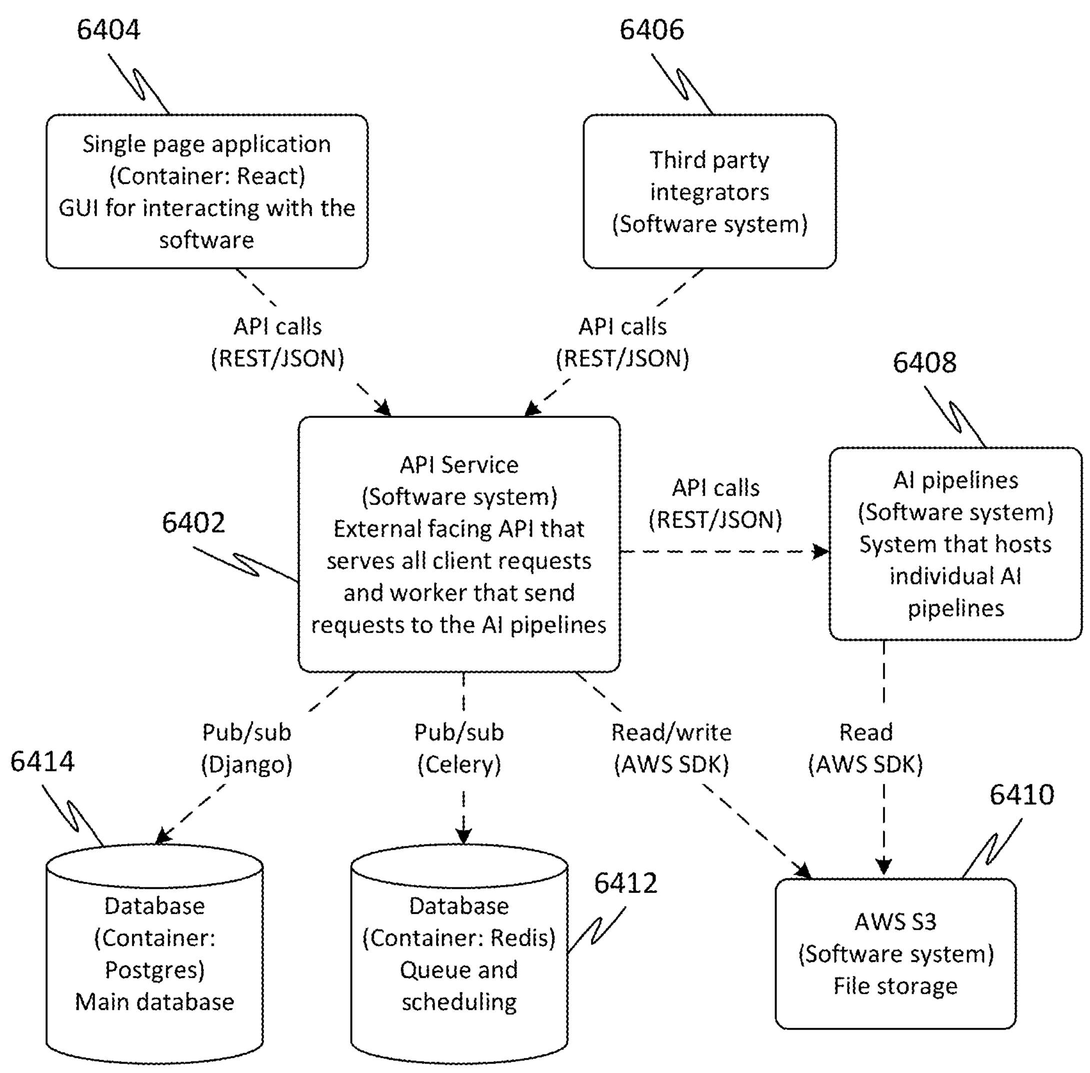
FIG. 64 illustrates a system diagram of the disclosed system, in accordance with some embodiments.

FIG. 64 illustrates a system diagram of the disclosed system, in accordance with some embodiments. Further, the disclosed system may include an API service (software system) 6402, a single page application (Container: React) 6404, third party integrators (software system) 6406, AI pipelines (software system) 6408, an AWS S3 (software system) 6410, a database (Container: Redis) 6412, and a database (Container: Postgres) 6414. Further, the API service (software system) 6402 may be an external facing API that serves all client requests and worker that send requests to the AI pipelines. Further, the single page application (Container: React) 6404 may be a GUI for interacting with the software. Further, the AI pipelines (software system) 6408 may be a system that hosts individual AI pipelines. Further, the AWS S3 (software system) 6410 may be a file storage. Further, the database (Container: Redis) 6412 may be used for queue and scheduling. Further, the database (Container: Postgres) 6414 is a main database. Further, the API service (software system) 6402 receives API calls (REST/JSON) from the single page application (Container: React) 6404 and the third party integrators (software system) 6406, send API calls (REST/JSON) to the AI pipelines (software system) 6408, reads/writes (AWS SDK) to the AWS S3 (software system) 6410, publish/subscribe (celery) to the database (Container: Redis) 6412, and publish/subscribe (Django) to the database (Container: Postgres) 6414. Further, the AI pipelines (software system) 6408 reads (AWS SDK) from the AWS S3 (software system) 6410.

Figure 65:
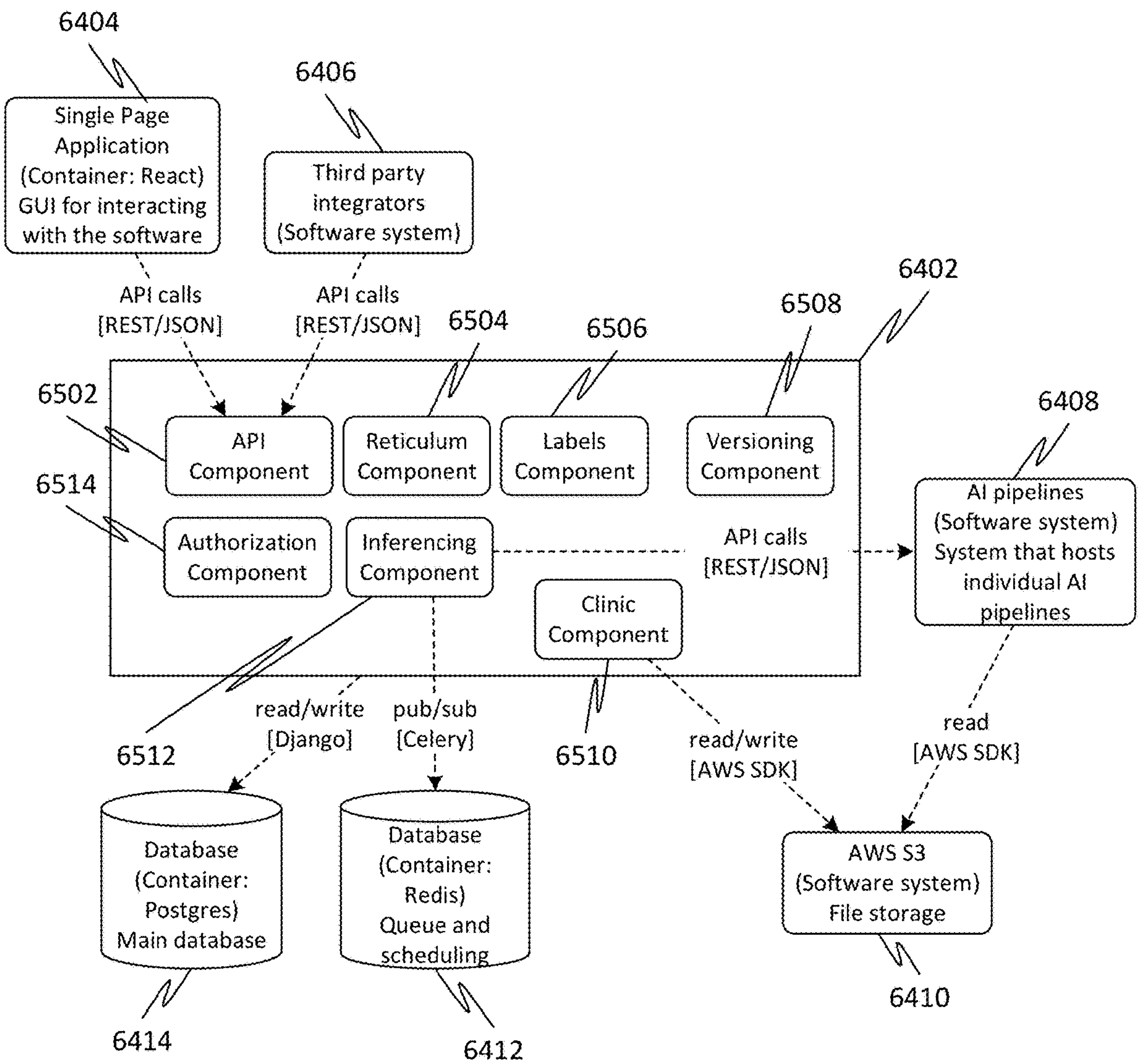
FIG. 65 illustrates a component diagram of the disclosed system, in accordance with some embodiments.

FIG. 65 illustrates a component diagram of the disclosed system, in accordance with some embodiments. Further, the API service (software system) 6402 may include an API component 6502, a reticulum component 6504, a labels component 6506, a versioning component 6508, a clinic component 6510, an inferencing component 6512, and an authorization component 6514. Further, the API component 6502 may receives API calls (REST/JSON) from the single page application (Container: React) 6404 and the third party integrators (software system) 6406. Further, the inferencing component 6512 sends API calls (REST/JSON) to the AI pipelines (software system) 6408 and publish/subscribe (celery) to the database (Container: Redis) 6412. Further, the clinic component 6510 read/write (AWS SDK) to the AWS S3 (software system) 6410.

Figure 66:
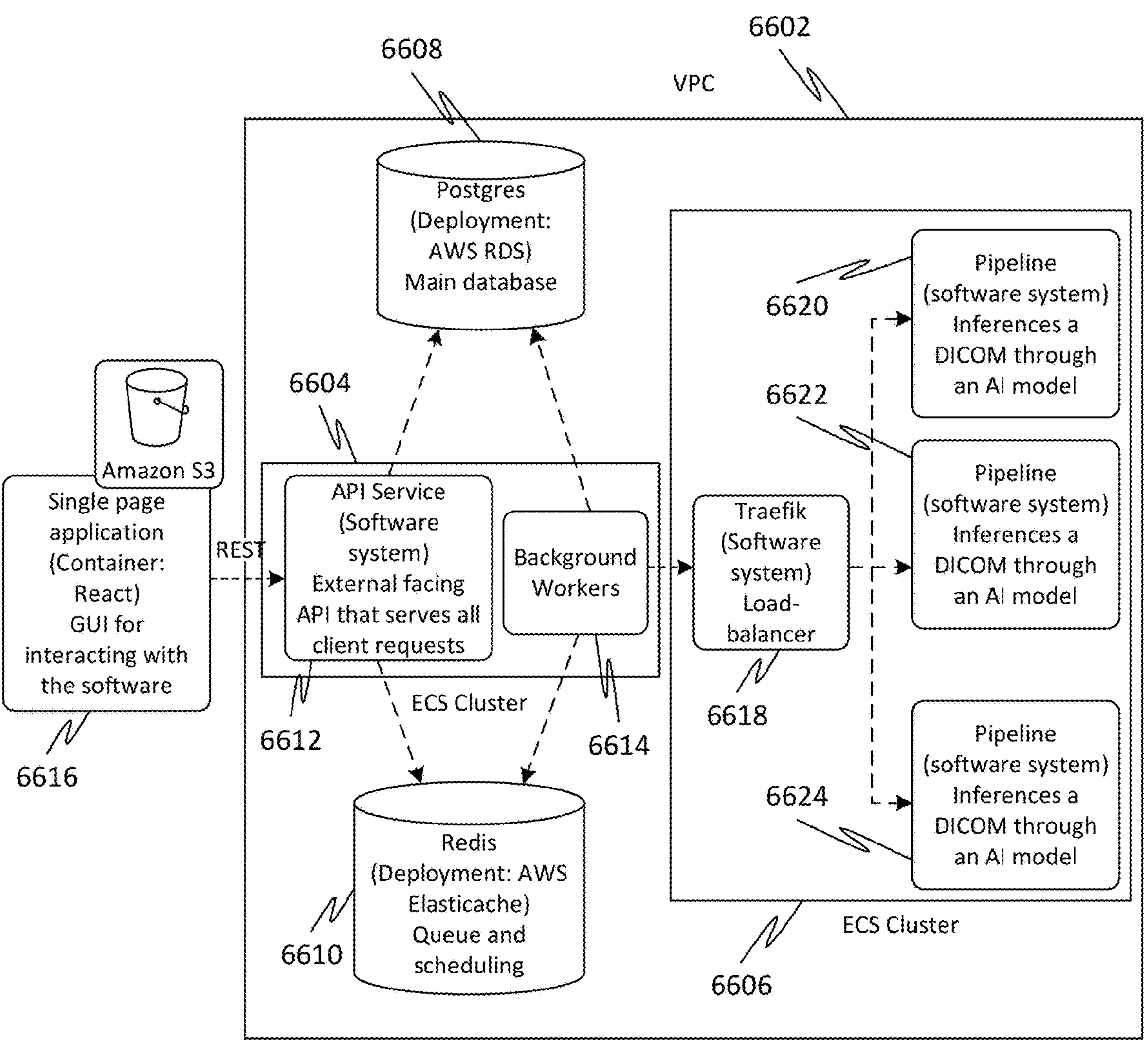
FIG. 66 illustrates a deployment diagram of the disclosed system, in accordance with some embodiments.

FIG. 66 illustrates a deployment diagram of the disclosed system, in accordance with some embodiments. Further, the disclosed system may include a virtual private cloud (VPC) 6602. Further, the VPC 6602 may include a first Elastic Container Service (ECS) cluster 6604, a second Elastic Container Service (ECS) cluster 6606, a main database 6608, and a queue and scheduling database 6610. Further, the main database 6608 may be a Postgres (Deployment AWS RDS) and the queue and scheduling database 6610 may be a Redis (Deployment: AWS Elasticache). Further, the first ECS cluster 6604 may include an API service (software system) 6612 and background workers 6614. Further, the API service (software system) 6612 may be an external facing API that serves all client requests. Further, the API service (software system) 6612 may receive API calls (REST) from a single page application (container: React) 6616. Further, the single page application (container: React) 6616 may be a GUI for interacting with the software. Further, the second ECS cluster 6606 may include a trafik (software system) 6618 and a plurality of pipelines (software systems) 6620-6624 connected with the trafik (software system) 6618. Further, the trafik (software system) 6618 may be a load balancer. Further, each of the plurality of pipelines (software systems) 6620-6624 inferences a DICOM through an AI model. Further, the trafik (software system) 6618 may be connected to the background workers 6614.

Figure 67:
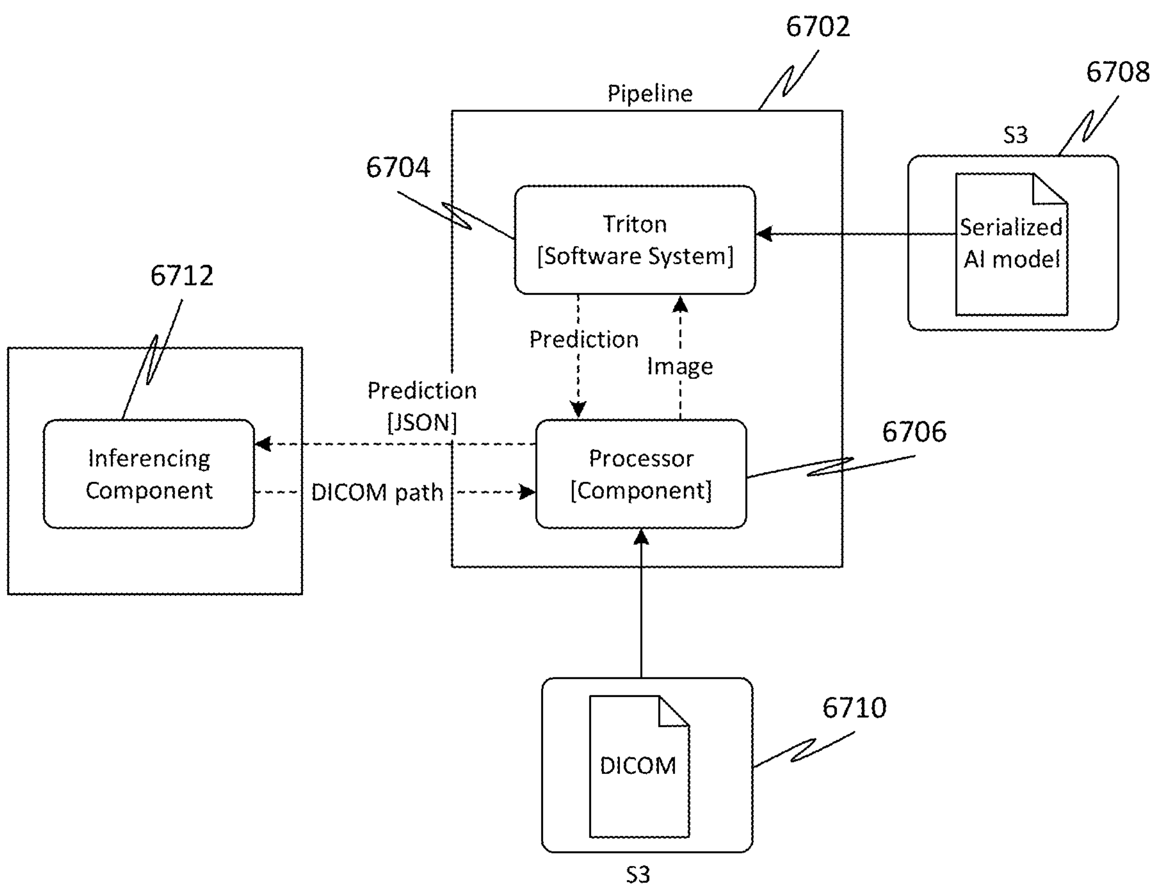
FIG. 67 illustrates a pipeline component diagram of the disclosed system, in accordance with some embodiments.

FIG. 67 illustrates a pipeline component diagram of the disclosed system, in accordance with some embodiments. Further, the disclosed system may include a pipeline 6702 comprising a triton (software system) 6704 and a processor (component) 6706. Further, the triton (software system) 6704 receives images from the processor (component) 6706 and a serialized AI model from a first Simple Storage Service (S3) 6708. Further, the processor (component) 6706 receives predictions from the triton (software system) 6704 and DICOM from a second Simple Storage Service (S3) 6710. Further, the processor (component) 6706 sends predictions (JSON) to an inferencing component 6712 and receives a DICOM path from the inferencing component 6712.

Modules

The modules associated with the disclosed system are:

1. API: The API module is a presentation layer of the disclosed system. Further, the API module exposes a REST API and handles most client requests. Further, the API module delegates the requests to the appropriate modules.
2. Clinic: The clinic module is responsible for the data received from the clients. Further, the clinic module holds the study, DICOM, and report entities. Further, the clinic module is responsible for extracting metadata, validation of the inputs, and initiation of scans.
3. Authorization: The authorization module is responsible for holding data related to the users, handles authorization, and manages authentication. Further, the authorization module holds information for webhooks.
4. Conclusions: The conclusions module is responsible for the storage and processing of the data related to the final reports that are presented to the clients.
5. Inferencing: The inferencing module is responsible for orchestrating the whole process of AI inference. Further, the inferencing module holds the tasks and the logic that is required to perform an end-to-end orchestration of all the AI pipelines. Further, the inferencing module handles exceptions, enforces rules and thresholds, and persists the data to the storage. Further, the inferencing module creates queue items that are related to the inference process, which the background workers consume.
6. Labels: The labels module holds static predefined entities that are used throughout the system.
7. Reticulum: The reticulum module holds data about the tools and pipelines of the disclosed system. Further, the reticulum module defines which pipeline will be executed for a given tool/solution.
8. Version: The version module holds the entities related to the history of the system configuration and the current version. Further, the version module provides a way to access the configuration of the system at any given time in the past and replicate the outputs. For example, the scans are related to the specific version that was used when they were issued.

FIG. 68 illustrates a 'base model' table 6802 of a clinic module database schema 6800, in accordance with some embodiments.

FIG. 69 illustrates a 'study <base model>' table 6902 of the clinic module database schema 6800, in accordance with some embodiments.

FIG. 70 illustrates a 'DICOM <base model>' table 7002 of the clinic module database schema 6800, in accordance with some embodiments.

FIG. 71 illustrates a 'Frame <base model>' table 7102 of the clinic module database schema 6800, in accordance with some embodiments.

FIG. 72 illustrates a 'Media <base model>' table 7202 of the clinic module database schema 6800, in accordance with some embodiments.

FIG. 73 illustrates a 'Reportconclusion <base model>' table 7302 of the clinic module database schema 6800, in accordance with some embodiments.

FIG. 74 illustrates a 'Report <base model>' table 7402 of the clinic module database schema 6800, in accordance with some embodiments.

FIG. 75 illustrates a 'base model' table 7502 of an authorization module database schema 7500, in accordance with some embodiments.

FIG. 76 illustrates a 'PermissionMixin' table 7602 of the authorization module database schema 7500, in accordance with some embodiments.

FIG. 77 illustrates an 'AbstractBaseUser' table 7702 of the authorization module database schema 7500, in accordance with some embodiments.

FIG. 78 illustrates a 'User<abstractBaseUser, PermissionMixin, BaseModel>' table 7802 of the authorization module database schema 7500, in accordance with some embodiments.

FIG. 79 illustrates a 'Webhook <baseModel>' table 7902 of the authorization module database schema 7500, in accordance with some embodiments.

FIG. 80 illustrates a 'WebhookDeliveryFailure<baseModel>' table 8002 of the authorization module database schema 7500, in accordance with some embodiments.

Figure 81:
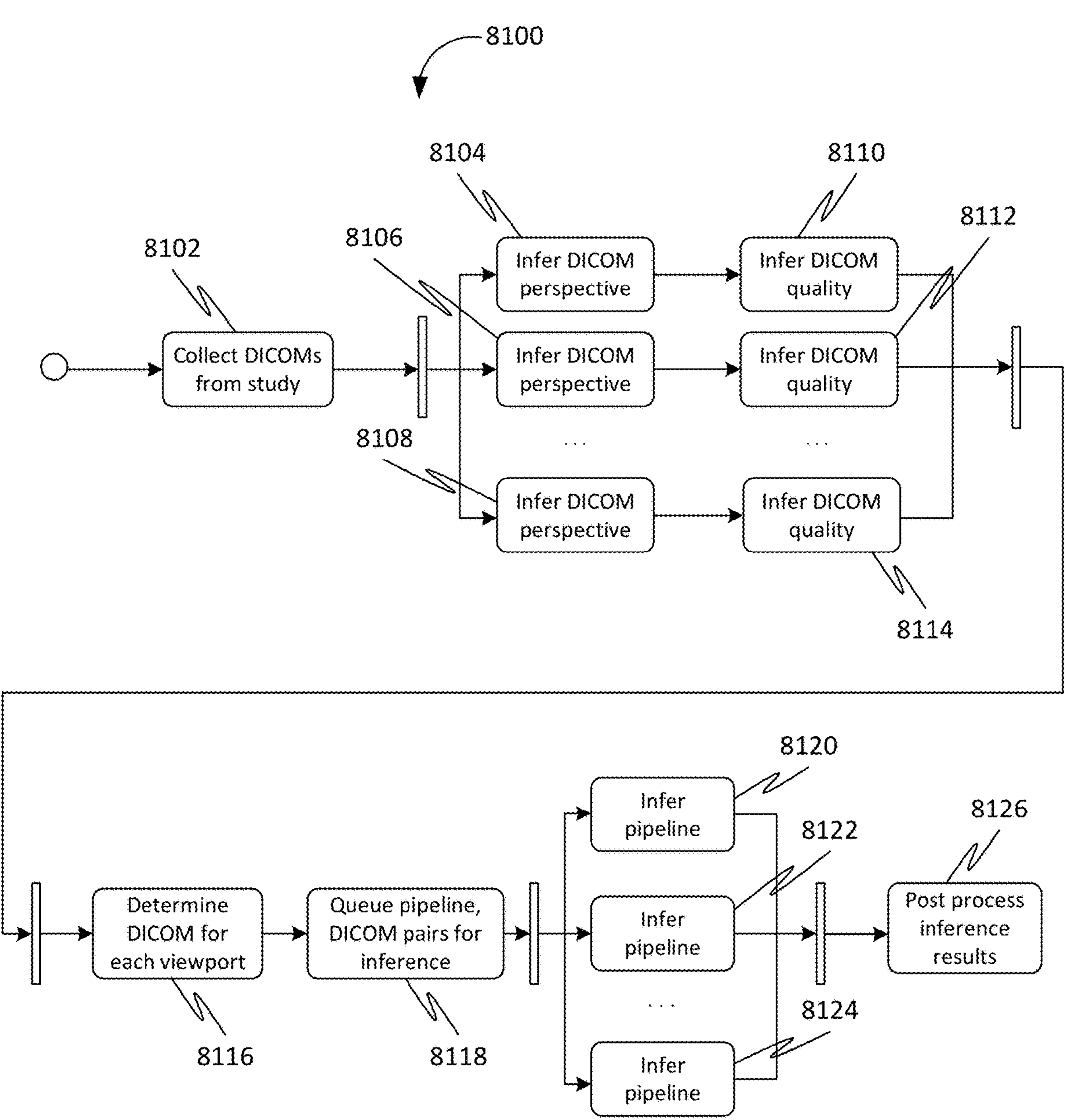
FIG. 81 is an activity diagram for an inference process 8100, in accordance with some embodiments.

FIG. 81 is an activity diagram for an inference process 8100, in accordance with some embodiments. Further, at step 8102 of the inference process 8100, DICOMs from a study are collected. Further, at steps 8104-8108 of the inference process 8100, a DICOM perspective of each DICOMs is inferred. Further, at steps 8110-8114 of the inference process 8100, a DICOM quality of each DICOMs is inferred. Further, at step 8116 of the inference process 8100, a DICOM for each viewport is determined. Further, at step 8118 of the inference process 8100, pipelines are queued with DICOM pairs for inference. Further, at steps 8120-8124 of the inference process 8100, each of the pipelines is inferred. Further, at step 8126 of the inference process 8100, inference results are post-processed.

Figure 82:
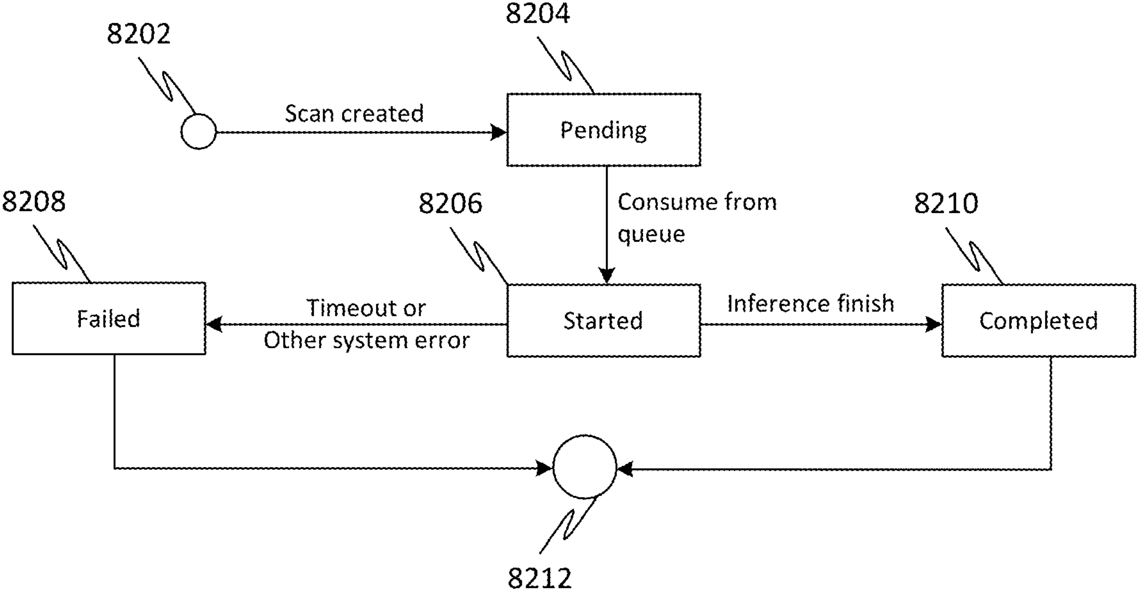
FIG. 82 is a scan state transition diagram for the disclosed system, in accordance with some embodiments.

FIG. 82 is a scan state transition diagram for the disclosed system, in accordance with some embodiments. Further, the disclosed system transitions from a first state 8202 to a pending state 8204 when a scan is created. Further, the disclosed system transitions from the pending state 8204 to a started state 8206 when the scan is consumed from the queue. Further, the disclosed system transitions from the started state 8206 to a failed state 8208 when there is a timeout or other system errors. Further, the disclosed system transitions from the started state 8206 to a completed state 8210 when the inference is finished. Further, the disclosed system transitions from the failed state 8208 and the completed state 8210 to a last state 8212.

Figure 83:
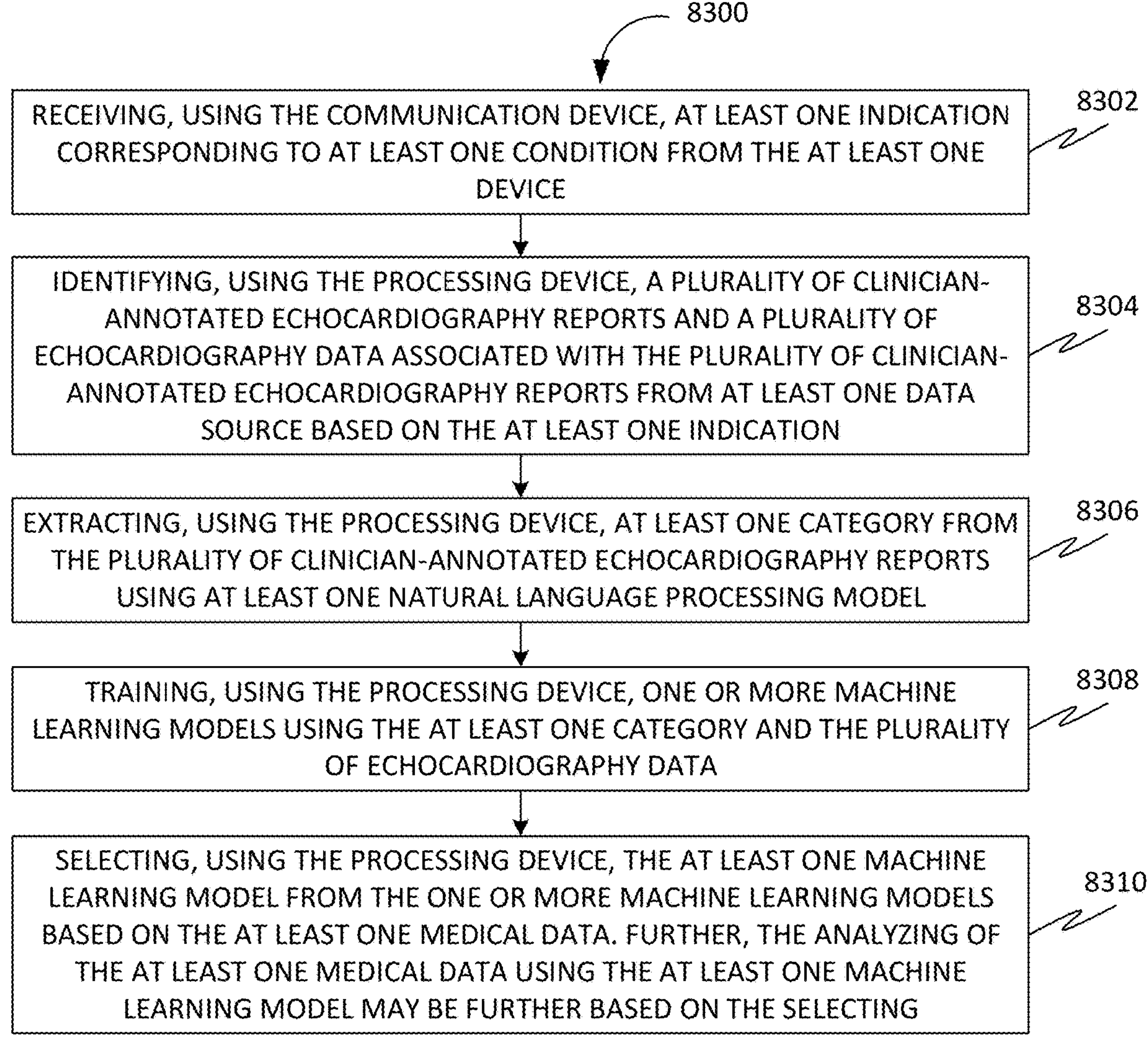
FIG. 83 is a flowchart of a method 8300 for facilitating a diagnosis of pathologies using a machine learning model, in accordance with some embodiments.

FIG. 83 is a flowchart of a method 8300 for facilitating a diagnosis of pathologies using a machine learning model, in accordance with some embodiments. Accordingly, the method 8300 may include a step 8302 of receiving, using the communication device, at least one indication corresponding to at least one condition from the at least one device. Further, the at least one condition may include a cardiac condition such as aortic stenosis, mitral regurgitation, tricuspid regurgitation, etc. Further, the at least one indication may include a cardia indication.

Further, the method 8300 may include a step 8304 of identifying, using the processing device, a plurality of clinician-annotated echocardiography reports and a plurality of echocardiography data associated with the plurality of clinician-annotated echocardiography reports from at least one data source based on the at least one indication. Further, the plurality of clinician-annotated echocardiography reports may include freeform clinician notes.

Further, the method 8300 may include a step 8306 of extracting, using the processing device, at least one category from the plurality of clinician-annotated echocardiography reports using at least one natural language processing model. Further, the at least one category may include "Present—Any Hypokinesis", "Severe—Global Hypokinesis", "Moderate—Enlargement", etc.

Further, the method 8300 may include a step 8308 of training, using the processing device, one or more machine learning models using the at least one category and the plurality of echocardiography data. Further, in an embodiment, the one or more machine learning models may be trained in a plurality of views of the plurality of echocardiography data. Further, in an embodiment, the one or more machine learning models may be trained in one or more selected view of the plurality of echocardiography data based on one or more view selection comprised in the at least one indication.

Further, the method 8300 may include a step 8310 of selecting, using the processing device, the at least one machine learning model from the one or more machine learning models based on the at least one medical data. Further, the analyzing of the at least one medical data using the at least one machine learning model may be further based on the selecting. Further, the at least one machine learning model may be selected based on an accuracy of the at least one machine learning model.

Figure 84:
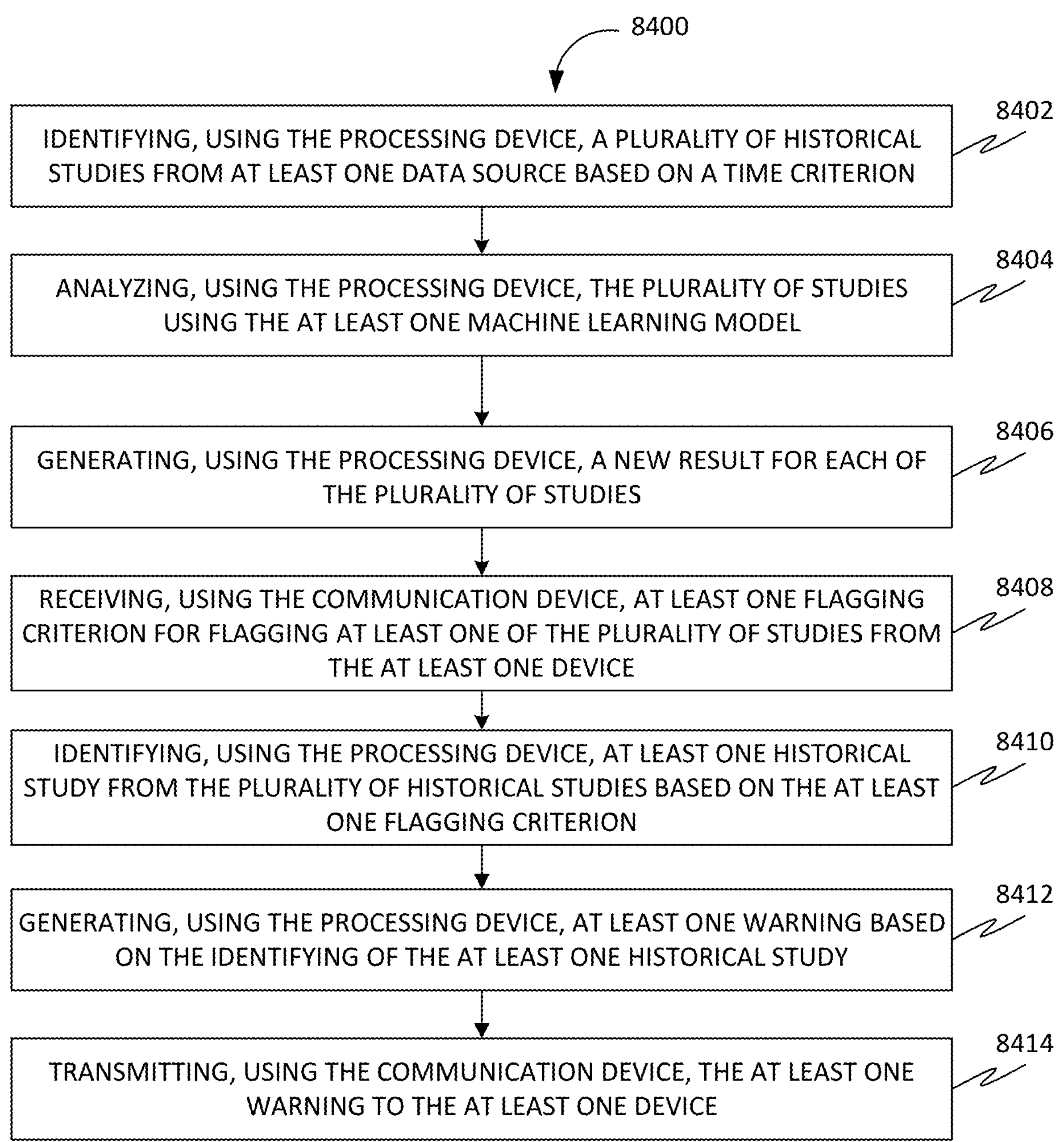
FIG. 84 is a flowchart of a method 8400 for facilitating a diagnosis of pathologies using a machine learning model, in accordance with some embodiments. 14

FIG. 84 is a flowchart of a method 8400 for facilitating a diagnosis of pathologies using a machine learning model, in accordance with some embodiments. Accordingly, the method 8400 may include a step 8402 of identifying, using the processing device, a plurality of historical studies from at least one data source based on a time criterion. Further, each of the plurality of historical studies may include at least one historical medical data and a historical result corresponding to the at least one historical medical data. Further, the at least one data source may include a database, a server, a client device, a hospital picture archiving and communication (PAC)/Electronic health record (EMR) system, etc. Further, the time criterion may be a specified date range.

Further, the method 8400 may include a step 8404 of analyzing, using the processing device, the plurality of studies using the at least one machine learning model.

Further, the method 8400 may include a step 8406 of generating, using the processing device, a new result for each of the plurality of studies.

Further, the method 8400 may include a step 8408 of receiving, using the communication device, at least one flagging criterion for flagging at least one of the plurality of studies from the at least one device. Further, the at least one flagging criterion may include a presence of moderate to severe aortic stenosis.

Further, the method 8400 may include a step 8410 of identifying, using the processing device, at least one historical study from the plurality of historical studies based on the at least one flagging criterion. Further, the new result of each of the at least one historical study disagrees with the historical result of each of the at least one historical study.

Further, the method 8400 may include a step 8412 of generating, using the processing device, at least one warning based on the identifying of the at least one historical study. Further, the at least one warning indicates a misdiagnosis associated with the at least one historical study.

Further, the method 8400 may include a step 8414 of transmitting, using the communication device, the at least one warning to the at least one device.

Figure 85:
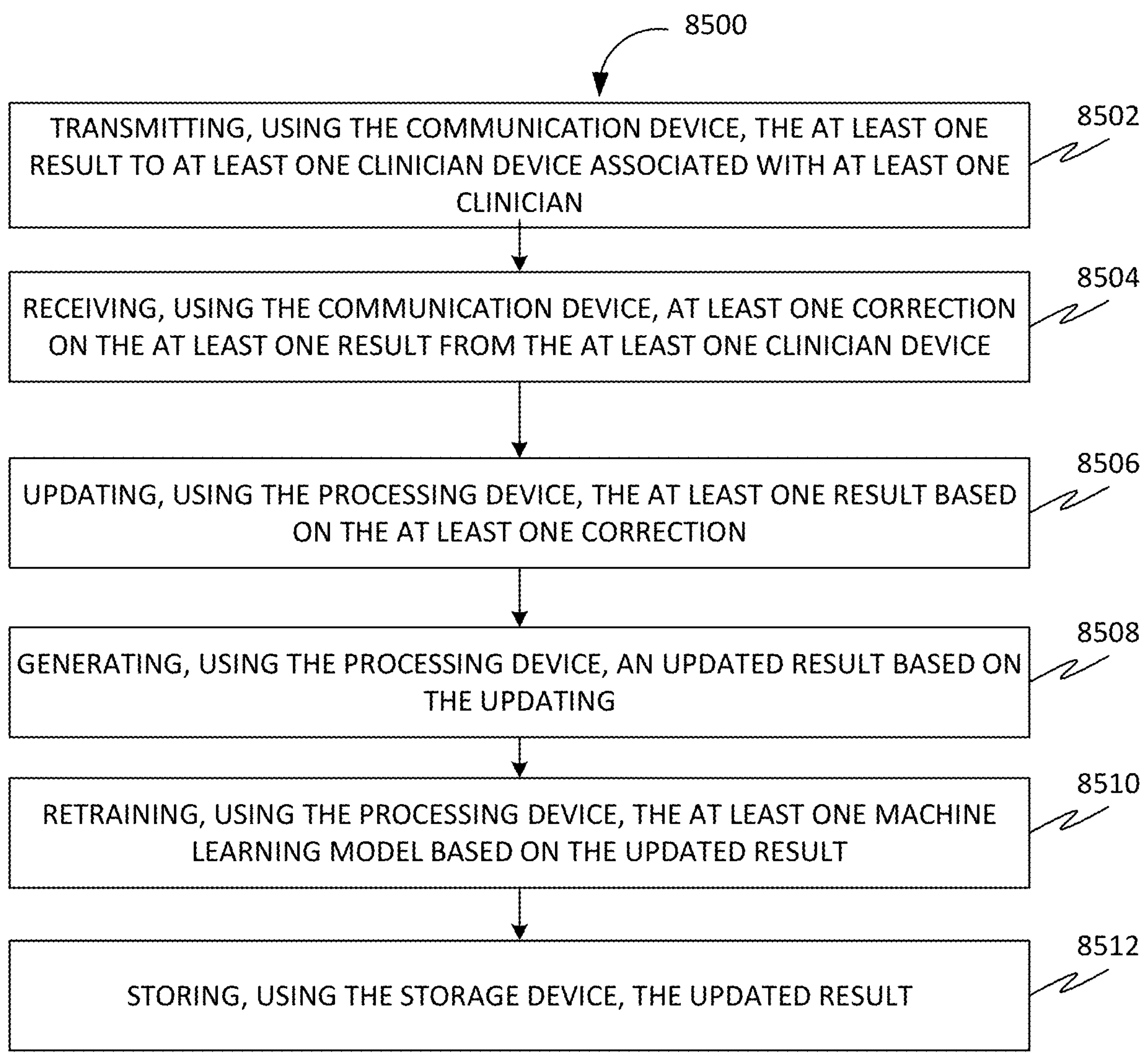
FIG. 85 is a flowchart of a method 8500 for facilitating a diagnosis of pathologies using a machine learning model, in accordance with some embodiments.

FIG. 85 is a flowchart of a method 8500 for facilitating a diagnosis of pathologies using a machine learning model, in accordance with some embodiments. Accordingly, the method 8500 may include a step 8502 of transmitting, using the communication device, the at least one result to at least one clinician device associated with at least one clinician. Further, the at least one clinician device may be the at least one device, a client device, a computing device, a user device, etc. Further, the at least one result may include at least one of a conclusion, a measurement, a finding, etc.

Further, the method 8500 may include a step 8504 of receiving, using the communication device, at least one correction on the at least one result from the at least one clinician device.

Further, the method 8500 may include a step 8506 of updating, using the processing device, the at least one result based on the at least one correction.

Further, the method 8500 may include a step 8508 of generating, using the processing device, an updated result based on the updating.

Further, the method 8500 may include a step 8510 of retraining, using the processing device, the at least one machine learning model based on the updated result.

Further, the method 8500 may include a step 8512 of storing, using the storage device, the updated result.

Components:

The present disclosure describes external software components associated with the disclosed system. Further, the external software components are:

1. Triton: Triton is an off-the-shelf software component that serves AI model inference requests. Further, the Triton loads the serialized AI model in a saved model format. The model is loaded from S3. Further, the inputs associated with the Triton may be an N-dimensional array of bytes that may represent the image or images from the DICOM preprocessing step from the AI Pipeline.
2. S3: S3 is a file storage system. Further, the S3 is used for persisting the DICOMs, report artifacts, images, video files, AI model weights, and other artifacts. Further, the S3 may be provided by a cloud provider as a service.
3. ECS: ECS is a container orchestration service that is used to host the components of a system. Further, ECS may be provided by a cloud provider as a service.
4. Traefik: Traefik is an off-the-shelf software component that provides load-balancing and routing capability. Further, Traefik may be used to load-balance and route the requests to specific AI pipelines.

According to some aspects, a method for facilitating diagnosis based on medical imaging data is disclosed. Further, the method may include receiving, using a communication device, a medical imaging data from a user device associated with a user. Further, the method may include analyzing, using a processing device, the medical imaging data using a plurality of machine learning models corresponding to a plurality of pathologies. Further, the method may include identifying, using the processing device, a plurality of pathological states based on the analyzing of the medical imaging data. Further, the method may include generating, using the processing device, a report data based on the identifying. Further, the method may include transmitting, using the communication device, the report data to the user device.

Further, according to some aspects, the method may include generating, using the processing device, at least one of a measurement and a finding associated with the plurality of pathologies based on the analyzing of the medical imaging data. Further, the medical imaging data may include echocardiography data. Further, the generating of the report data may be based on the generating of at least one of the measurement and the finding. Further, the report data may include at least one of the measurement and the finding. Further, the method may include transmitting, using the communication device, the report data to at least one clinician device associated with at least one clinician. Further, the at least one clinician device presents the report data comprising at least one of the measurement and the finding to the at least one clinician. Further, the method may include receiving, using the communication device, at least one correction on at least one of the measurement and the finding from the at least one clinician device. Further, the method may include updating, using the processing device, at least one of the measurement and the finding based on the at least one correction. Further, the method may include generating, using the processing device, at least one of a corrected measurement and a corrected finding based on the updating. Further, the method may include retraining, using the processing device, the plurality of machine learning models using at least one of the corrected measurement and the corrected finding. Further, the retraining improves future results produced by the plurality of machine learning models. Further, the method may include storing, using a storage device, at least one of the corrected measurement and the corrected finding.

Further, according to some aspects, the method may include accessing, using the processing device, a plurality of clinician-annotated echo reports and a plurality of echocardiography imagery from a database. Further, the method may include analyzing, using the processing device, the plurality of clinician-annotated echo reports and the plurality of echocardiography imagery based on the accessing. Further, the method may include identifying, using the processing device, the plurality of pathologies present in the plurality of clinician-annotated echo reports and the plurality of echocardiography imagery based on the analyzing of the plurality of clinician-annotated echo reports and the plurality of echocardiography imagery. Further, the method may include generating, using the processing device, the plurality of machine learning models corresponding to the plurality of pathologies based on the analyzing of the plurality of clinician-annotated echo reports and the plurality of echocardiography imagery and the identifying of the plurality of pathologies. Further, the analyzing of the medical imaging data using the plurality of machine learning models corresponding to the plurality of pathologies may be based on the generating of the plurality of machine learning models. Further, the method may include storing, using a storage device, the plurality of machine learning models.

Further, according to some aspects, the method may include receiving, using the communication device, a plurality of primary medical imaging data from a device.

Further, the plurality of primary medical imaging data may include a plurality of echocardiography images. Further, the method may include receiving, using the communication device, a plurality of secondary medical imaging data associated with a plurality of imaging modalities from the device. Further, the plurality of primary medical imaging data corresponds to the plurality of secondary medical imaging data. Further, the plurality of secondary medical imaging data may include a plurality of annotations. Further, the plurality of secondary medical imaging data may include at least one of magnetic resonance imaging (MRI) images, computed tomography (CT) images, and stress echo images. Further, the method may include training, using the processing device, a plurality of untrained machine learning models using the plurality of primary medical imaging data and the plurality of secondary medical imaging data. Further, the plurality of untrained machine learning models learns a correlation between a plurality of features in the plurality of primary medical imaging data with the plurality of annotations in the plurality of secondary medical imaging data. Further, the method may include generating, using the processing device, the plurality of machine learning models for diagnosing the plurality of pathologies based on the training. Further, the analyzing of the medical imaging data using the plurality of machine learning models corresponding to the plurality of pathologies may be based on the generating of the plurality of machine learning models. Further, the method may include storing, using a storage device, the plurality of machine learning models.

Further, according to some aspects, the method may include accessing, using the processing device, a plurality of studies and a plurality of results corresponding to the plurality of studies from a database based on a time criterion. Further, the method may include analyzing, using the processing device, the plurality of studies using the plurality of machine learning models. Further, the method may include generating, using the processing device, a plurality of new results for the plurality of studies. Further, the method may include receiving, using the communication device, a plurality of criteria for flagging at least one of the plurality of studies. Further, the method may include identifying, using the processing device, at least one study from the plurality of studies based on the plurality of criteria. Further, the at least one study may be associated with at least one result and at least one new result. Further, the at least one result disagrees with the at least one new result. Further, the generating of the report data may be based on the identifying of the at least one study.

According to some aspects, a system facilitating diagnosis based on medical imaging data of a user is disclosed. Further, the system may include a communication device and a processing device. Further, the communication device may be configured for receiving a medical imaging data from a user device associated with a user. Further, the communication device may be configured for transmitting a report data to the user device. Further, the processing device may be communicatively coupled with the communication device. Further, the processing device may be configured for analyzing the medical imaging data using a plurality of machine learning models corresponding to a plurality of pathologies. Further, the processing device may be configured for identifying a plurality of pathological states based on the analyzing of the medical imaging data. Further, the processing device may be configured for generating the report data based on the identifying.

According to some aspects, a medical imaging device facilitating diagnosis of a user is disclosed. Further, the medical imaging device may be configured for generating a medical imaging data of the user. Further, the medical imaging device may include a processing device and a communication device. Further, the processing device may be configured for analyzing the medical imaging data using a plurality of machine learning models corresponding to a plurality of pathologies. Further, the processing device may be configured for identifying a plurality of pathological states based on the analyzing of the medical imaging data. Further, the processing device may be configured for generating a report data based on the identifying. Further, the communication device may be communicatively coupled with the processing device. Further, the communication device may be configured for transmitting the report data to a user device.

Although the invention has been explained in relation to its preferred embodiment, it is to be understood that many other possible modifications and variations can be made without departing from the spirit and scope of the invention as hereinafter claimed.

What is claimed is:

1. A method for facilitating a diagnosis of pathologies using at least one machine learning model, the method comprising:

receiving, using a communication connection, at least one medical data associated with at least one user from at least one device;

receiving, using the communication connection, at least one indication corresponding to at least one condition from the at least one device;

identifying, using a processing unit, a plurality of clinician-annotated echocardiography reports and a plurality of echocardiography data associated with the plurality of clinician-annotated echocardiography reports from at least one data source based on the at least one indication;

extracting, using the processing unit, at least one category from the plurality of clinician-annotated echocardiography reports using at least one natural language processing model;

training, using the processing unit, one or more machine learning models using the at least one category and the plurality of echocardiography data;

selecting, using the processing unit, the at least one machine learning model from the one or more machine learning models based on the at least one medical data;

analyzing, using the processing unit, the at least one medical data using the at least one machine learning model, wherein the analyzing of the at least one medical data using the at least one machine learning model is further based on the selecting, wherein the at least one machine learning model comprises at least one artificial neural network comprising a plurality of layers, wherein the plurality of layers comprises at least one input layer, a plurality of output layers, and at least one middle layer between the at least one input layer and the plurality of output layers, wherein the at least one input layer is configured for taking a plurality of medical data as a plurality of inputs to the at least one input layer, wherein the at least one middle layer is configured for outputting a lower dimensional abstract vector space representation for each of the plurality of inputs by encoding the plurality of medical data to a lower dimensional abstract vector space, wherein the plurality of output layers is configured for classifying the lower dimensional abstract vector space representation to a plurality of outputs corresponding to a plurality of assessment parameters considered in the diagnosis of the pathologies, wherein each of the plurality of output layers is configured for communicating each of the plurality of outputs with at least one of the plurality of output layers, wherein each of the plurality of output layers is configured for adjusting each of the plurality of outputs based on the at least one of the plurality of outputs of at least one of the plurality of output layers, wherein the analyzing of the at least one medical data comprises inputting the at least one medical data to the at least one machine learning model;

obtaining, using the processing unit, one or more outputs corresponding to one or more assessment parameters from the at least one machine learning model for the diagnosis of one or more pathologies based on the analyzing of the at least one medical data;

generating, using the processing unit, at least one result based on the one or more outputs; and storing, using a system memory, the at least one result and the at least one machine learning model.

2. The method of claim 1, wherein the at least one device comprises at least one medical imaging unit, wherein the at least one medical imaging unit is associated with at least one ultrasound imaging modality, wherein the at least one medical imaging unit is configured for generating the at least one medical data associated with the at least one user by imaging at least one portion of at least one body part of the at least one user, wherein the imaging comprises ultrasound imaging of the at least one portion of the at least one body part of the at least one user, wherein the at least one medical imaging unit comprises at least one transducer, wherein the at least one transducer generates and transmits ultrasound waves to the at least one portion of the at least one body part and receives echos of the ultrasound waves from the at least one portion of the at least one body part for the generating of the at least one medical data.

3. The method of claim 1, wherein the at least one medical data further comprises at least one echocardiography data corresponding to at least one study, wherein the analyzing of the at least one medical data further comprises analyzing the at least one echocardiography data using the at least one machine learning model, wherein the one or more outputs comprises one or more predictions of a presence of one or more conditions, one or more estimations of one or more measurements, one or more visualizations of the one or more measurements, and one or more conclusions of the diagnosis, wherein the obtaining of the one or more outputs comprises obtaining the one or more predictions of the presence of the one or more conditions, the one or more estimations of the one or more measurements, the one or more visualizations of the one or more measurements, and the one or more conclusions of the diagnosis from the at least one machine learning model, wherein the at least one result comprises an echocardiography report, wherein the generating of the at least one result comprises generating the echocardiography report by combining the one or more predictions of the presence of the one or more conditions, the one or more estimations of the one or more measurements, the one or more visualizations of the one or more measurements, and the one or more conclusions of the diagnosis.

4. The method of claim 1, wherein the at least one medical data further comprises at least one B mode image, wherein the analyzing of the at least one medical data further comprises analyzing the at least one B mode image using the at least one machine learning model, wherein the one or more outputs comprises one or more estimations of one or more Doppler echocardiographic measurements and one or more predictions of one or more conditions, wherein the obtaining of the one or more outputs comprises obtaining the one or more estimations of the one or more Doppler echocardiographic measurements and the one or more predictions of the one or more conditions from the at least one machine learning model, wherein the generating of the at least one result is further based on the one or more estimations of the one or more Doppler echocardiographic measurements and the one or more predictions of the one or more conditions.

5. The method of claim 1 further comprising:

identifying, using the processing unit, a plurality of historical studies from at least one data source based on a time criterion, wherein each of the plurality of historical studies comprises at least one historical medical data and a historical result corresponding to the at least one historical medical data;

analyzing, using the processing unit, the plurality of studies using the at least one machine learning model;

generating, using the processing unit, a new result for each of the plurality of studies;

receiving, using the communication connection, at least one flagging criterion for flagging at least one of the plurality of studies from the at least one device;

identifying, using the processing unit, at least one historical study from the plurality of historical studies based on the at least one flagging criterion, wherein the new result of each of the at least one historical study disagrees with the historical result of each of the at least one historical study;

generating, using the processing unit, at least one warning based on the identifying of the at least one historical study, wherein the at least one warning indicates a misdiagnosis associated with the at least one historical study; and transmitting, using the communication connection, the at least one warning to the at least one device.

6. The method of claim 1 further comprising:

transmitting, using the communication connection, the at least one result to at least one clinician device associated with at least one clinician;

receiving, using the communication connection, at least one correction on the at least one result from the at least one clinician device;

updating, using the processing unit, the at least one result based on the at least one correction;

generating, using the processing unit, an updated result based on the updating;

retraining, using the processing unit, the at least one machine learning model based on the updated result; and storing, using the system memory, the updated result.

7. The method of claim 1 further comprising:

receiving, using the communication connection, at least one additional medical data associated with the at least one user from the at least one device, wherein the at least one medical data is associated with at least one modality and the at least one additional medical data is associated with at least one additional modality; and analyzing, using the processing unit, the at least one additional medical data using the at least one machine learning model, wherein the at least one machine learning model further comprises at least one additional artificial neural network, wherein the at least one artificial neural network is trained using a set of training medical data associated with the at least one modality and the at least one additional artificial neural network is trained using a set of additional training medical data associated with the at least one additional modality, wherein the set of additional training medical data corresponds to the set of training medical data, wherein the at least one artificial neural network and the at least one additional artificial neural network are jointly trained with a cross modality artificial neural network of the at least one machine learning model using a loss function created using outputs from the cross modality artificial neural network, the at least one artificial neural network, and the at least one additional artificial neural network, wherein the jointly training of the at least one artificial neural network and the at least one additional artificial neural network with the cross modality artificial neural network leverages at least one data fusion technique to enhance an accuracy of the at least one machine learning model by combining the at least one modality of the set of training medical data with the at least one additional modality of the set of training medical data, wherein the obtaining of the one or more outputs is further based on the analyzing of the at least one additional medical data.

8. The method of claim 1 further comprising:

receiving, using the communication connection, at least one user input from at least one input device;

processing, using the processing unit, the at least one result and the at least one user input using a conversational model;

generating, using the processing unit, at least one response corresponding to the at least one user input based on the processing;

transmitting, using the communication connection, the at least one response to at least one output device; and storing, using the system memory, the at least one user input and the at least one response.

9. The method of claim 1, wherein the at least one medical data further comprises a freeform text corresponding to a note, wherein the at least one artificial neural network comprises at least one additional output layer, wherein the at least one additional output layer is configured for predicting text tokens by decoding the lower dimensional abstract vector space representation, wherein the obtaining of the one or more outputs further comprises obtaining at least one text token corresponding to at least one additional assessment parameter for the diagnosis of the one or more pathologies, wherein the generating of the at least one result is further based on the at least one text token.

10. A system for facilitating a diagnosis of pathologies using at least one machine learning model, the system comprising:

a communication connection configured for:

receiving at least one medical data associated with at least one user from at least one device; and receiving at least one indication corresponding to at least one condition from the at least one device:

a processing unit communicatively coupled with the communication connection, wherein the processing unit is configured for:

identifying a plurality of clinician-annotated echocardiography reports and a plurality of echocardiography data associated with the plurality of clinician-annotated echocardiography reports from at least one data source based on the at least one indication;

extracting at least one category from the plurality of clinician-annotated echocardiography reports using at least one natural language processing model;

training one or more machine learning models using the at least one category and the plurality of echocardiography data;

selecting the at least one machine learning model from the one or more machine learning models based on the at least one medical data;

analyzing the at least one medical data using the at least one machine learning model, wherein the analyzing of the at least one medical data using the at least one machine learning model is further based on the selecting, wherein the at least one machine learning model comprises at least one artificial neural network comprising a plurality of layers, wherein the plurality of layers comprises at least one input layer, a plurality of output layers, and at least one middle layer between the at least one input layer and the plurality of output layers, wherein the at least one input layer is configured for taking a plurality of medical data as a plurality of inputs to the at least one input layer, wherein the at least one middle layer is configured for outputting a lower dimensional abstract vector space representation for each of the plurality of inputs by encoding the plurality of medical data to a lower dimensional abstract vector space, wherein the plurality of output layers is configured for classifying the lower dimensional abstract vector space representation to a plurality of outputs corresponding to a plurality of assessment parameters considered in the diagnosis of the pathologies, wherein each of the plurality of output layers is configured for communicating each of the plurality of outputs with at least one of the plurality of output layers, wherein each of the plurality of output layers is configured for adjusting each of the plurality of outputs based on the at least one of the plurality of outputs of at least one of the plurality of output layers, wherein the analyzing of the at least one medical data comprises inputting the at least one medical data to the at least one machine learning model;

obtaining one or more outputs corresponding to one or more assessment parameters from the at least one machine learning model for the diagnosis of one or more pathologies based on the analyzing of the at least one medical data; and generating at least one result based on the one or more outputs; and a system memory communicatively coupled with the processing unit, wherein the system memory is configured for storing the at least one result and the at least one machine learning model.

11. The system of claim 10, wherein the at least one device comprises at least one medical imaging unit, wherein the at least one medical imaging unit is associated with at least one ultrasound imaging modality, wherein the at least one medical imaging unit is configured for generating the at least one medical data associated with the at least one user by imaging at least one portion of at least one body part of the at least one user, wherein the imaging comprises ultrasound imaging of the at least one portion of the at least one body part of the at least one user, wherein the at least one medical imaging unit comprises at least one transducer, wherein the at least one transducer generates and transmits ultrasound waves to the at least one portion of the at least one body part and receives echos of the ultrasound waves from the at least one portion of the at least one body part for the generating of the at least one medical data.

12. The system of claim 10, wherein the at least one medical data further comprises at least one echocardiography data corresponding to at least one study, wherein the analyzing of the at least one medical data further comprises analyzing the at least one echocardiography data using the at least one machine learning model, wherein the one or more outputs comprises one or more predictions of a presence of one or more conditions, one or more estimations of one or more measurements, one or more visualizations of the one or more measurements, and one or more conclusions of the diagnosis, wherein the obtaining of the one or more outputs comprises obtaining the one or more predictions of the presence of the one or more conditions, the one or more estimations of the one or more measurements, the one or more visualizations of the one or more measurements, and the one or more conclusions of the diagnosis from the at least one machine learning model, wherein the at least one result comprises an echocardiography report, wherein the generating of the at least one result comprises generating the echocardiography report by combining the one or more predictions of the presence of the one or more conditions, the one or more estimations of the one or more measurements, the one or more visualizations of the one or more measurements, and the one or more conclusions of the diagnosis.

13. The system of claim 10, wherein the at least one medical data further comprises at least one B mode image, wherein the analyzing of the at least one medical data further comprises analyzing the at least one B mode image using the at least one machine learning model, wherein the one or more outputs comprises one or more estimations of one or more Doppler echocardiographic measurements and one or more predictions of one or more conditions, wherein the obtaining of the one or more outputs comprises obtaining the one or more estimations of the one or more Doppler echocardiographic measurements and the one or more predictions of the one or more conditions from the at least one machine learning model, wherein the generating of the at least one result is further based on the one or more estimations of the one or more Doppler echocardiographic measurements and the one or more predictions of the one or more conditions.

14. The system of claim 10, wherein the processing unit is further configured for:

identifying a plurality of historical studies from at least one data source based on a time criterion, wherein each of the plurality of historical studies comprises at least one historical medical data and a historical result corresponding to the at least one historical medical data;

analyzing the plurality of studies using the at least one machine learning model;

generating a new result for each of the plurality of studies;

identifying at least one historical study from the plurality of historical studies based on at least one flagging criterion, wherein the new result of each of the at least one historical study disagrees with the historical result of each of the at least one historical study; and generating at least one warning based on the identifying of the at least one historical study, wherein the at least one warning indicates a misdiagnosis associated with the at least one historical study, wherein the communication connection is further configured for:

receiving the at least one flagging criterion for flagging at least one of the plurality of studies from the at least one device; and transmitting the at least one warning to the at least one device.

15. The system of claim 10, wherein the communication connection is further configured for:

transmitting the at least one result to at least one clinician device associated with at least one clinician; and receiving at least one correction on the at least one result from the at least one clinician device, wherein the processing unit is further configured for:

updating the at least one result based on the at least one correction;

generating an updated result based on the updating; and retraining the at least one machine learning model based on the updated result, wherein the system memory is further configured for storing the updated result.

16. The system of claim 10, wherein the communication connection is further configured for receiving at least one additional medical data associated with the at least one user from the at least one device, wherein the at least one medical data is associated with at least one modality and the at least one additional medical data is associated with at least one additional modality, wherein the processing unit is further configured for analyzing the at least one additional medical data using the at least one machine learning model, wherein the at least one machine learning model further comprises at least one additional artificial neural network, wherein the at least one artificial neural network is trained using a set of training medical data associated with the at least one modality and the at least one additional artificial neural network is trained using a set of additional training medical data associated with the at least one additional modality, wherein the set of additional training medical data corresponds to the set of training medical data, wherein the at least one artificial neural network and the at least one additional artificial neural network are jointly trained with a cross modality artificial neural network of the at least one machine learning model using a loss function created using outputs from the cross modality artificial neural network, the at least one artificial neural network, and the at least one additional artificial neural network, wherein the obtaining of the one or more outputs is further based on the analyzing of the at least one additional medical data.

17. The system of claim 10, wherein the communication connection is further configured for:

receiving at least one user input from at least one input device; and transmitting at least one response to at least one output device, wherein the processing unit is further configured for:

processing the at least one result and the at least one user input using a conversation al model; and generating the at least one response corresponding to the at least one user input based on the processing, wherein the system memory is further configured for storing the at least one user input and the at least one response.

18. The system of claim 10, wherein the at least one medical data further comprises a freeform text corresponding to a note, wherein the at least one artificial neural network comprises at least one additional output layer, wherein the at least one additional output layer is configured for predicting text tokens by decoding the lower dimensional abstract vector space representation, wherein the obtaining of the one or more outputs further comprises obtaining at least one text token corresponding to at least one additional assessment parameter for the diagnosis of the one or more pathologies, wherein the generating of the at least one result is further based on the at least one text token.

19. A device for facilitating a diagnosis of pathologies using at least one machine learning model, the device comprising:

at least one medical imaging unit configured for generating at least one medical data associated with at least one user by imaging at least one portion of at least one body part of the at least one user, wherein the at least one medical imaging unit is associated with at least one ultrasound imaging modality, wherein the imaging comprises ultrasound imaging of the at least one portion of the at least one body part of the at least one user, wherein the at least one medical imaging unit comprises at least one transducer, wherein the at least one transducer generates and transmits ultrasound waves to the at least one portion of the at least one body part and receives echos of the ultrasound waves from the at least one portion of the at least one body part for the generating of the at least one medical data;

a processing unit communicatively coupled with the at least one medical imaging unit, wherein the processing unit is configured for:

identifying a plurality of clinician-annotated echocardiography reports and a plurality of echocardiography data associated with the plurality of clinician-annotated echocardiography reports from at least one data source based on at least one indication corresponding to at least one condition;

extracting at least one category from the plurality of clinician-annotated echocardiography reports using at least one natural language processing model;

training one or more machine learning models using the at least one category and the plurality of echocardiography data;

selecting the at least one machine learning model from the one or more machine learning models based on the at least one medical data;

analyzing the at least one medical data using the at least one machine learning model, wherein the analyzing of the at least one medical data using the at least one machine learning model is further based on the selecting, wherein the at least one machine learning model comprises at least one artificial neural network comprising a plurality of layers, wherein the plurality of layers comprises at least one input layer, a plurality of output layers, and at least one middle layer between the at least one input layer and the plurality of output layers, wherein the at least one input layer is configured for taking a plurality of medical data as a plurality of inputs to the at least one input layer, wherein the at least one middle layer is configured for outputting a lower dimensional abstract vector space representation for each of the plurality of inputs by encoding the plurality of medical data to a lower dimensional abstract vector space, wherein the plurality of output layers is configured for classifying the lower dimensional abstract vector space representation to a plurality of outputs corresponding to a plurality of assessment parameters considered in the diagnosis of the pathologies, wherein each of the plurality of output layers is configured for communicating each of the plurality of outputs with at least one of the plurality of output layers, wherein each of the plurality of output layers is configured for adjusting each of the plurality of outputs based on the at least one of the plurality of outputs of at least one of the plurality of output layers, wherein the analyzing of the at least one medical data comprises inputting the at least one medical data to the at least one machine learning model;

obtaining one or more outputs corresponding to one or more assessment parameters from the at least one machine learning model for the diagnosis of one or more pathologies based on the analyzing of the at least one medical data; and generating at least one result based on the one or more outputs; and a system memory communicatively coupled with the processing unit, wherein the system memory is configured for storing the at least one result and the at least one machine learning model.

20. The device of claim 19, wherein the at least one medical data further comprises at least one B mode image, wherein the analyzing of the at least one medical data further comprises analyzing the at least one B mode image using the at least one machine learning model, wherein the one or more outputs comprises one or more estimations of one or more Doppler echocardiographic measurements and one or more predictions of one or more conditions, wherein the obtaining of the one or more outputs comprises obtaining the one or more estimations of the one or more Doppler echocardiographic measurements and the one or more predictions of the one or more conditions from the at least one machine learning model, wherein the generating of the at least one result is further based on the one or more estimations of the one or more Doppler echocardiographic measurements and the one or more predictions of the one or more conditions.

* * * * *